US012378450B2

(12) United States Patent
Furukawa et al.

(10) Patent No.: US 12,378,450 B2
(45) Date of Patent: Aug. 5, 2025

(54) ADHESIVE FOR ENDOSCOPE AND CURED PRODUCT THEREOF, AND ENDOSCOPE AND METHOD FOR PRODUCING THE SAME

(71) Applicant: FUJIFILM Corporation, Tokyo (JP)

(72) Inventors: Kazushi Furukawa, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 136 days.

(21) Appl. No.: 18/169,330

(22) Filed: Feb. 15, 2023

(65) Prior Publication Data

US 2023/0203353 A1 Jun. 29, 2023

Related U.S. Application Data

(63) Continuation of application No. PCT/JP2021/032923, filed on Sep. 8, 2021.

(30) Foreign Application Priority Data

Sep. 29, 2020 (JP) ................................ 2020-163597

(51) Int. Cl.
*C09J 163/00* (2006.01)
*A61B 1/00* (2006.01)
*C09J 11/06* (2006.01)

(52) U.S. Cl.
CPC ........... *C09J 163/00* (2013.01); *A61B 1/0011* (2013.01); *A61B 1/00128* (2013.01); *C09J 11/06* (2013.01)

(58) Field of Classification Search
USPC ........................................................ 528/86
See application file for complete search history.

(56) References Cited

U.S. PATENT DOCUMENTS

2008/0114205 A1 5/2008 Kagawa et al.
2011/0245612 A1* 10/2011 Nakamura ........... A61B 1/0055 427/2.12
2019/0082937 A1* 3/2019 Hayashi ................. A61B 1/005
2020/0107697 A1 4/2020 Furukawa et al.
2020/0187755 A1 6/2020 Furukawa et al.
2021/0380834 A1 12/2021 Nakai et al.

FOREIGN PATENT DOCUMENTS

JP 2001-115126 A 4/2001
JP 2002-097442 A 4/2002
JP 2006-218102 A 8/2006
JP 2007-161811 A 6/2007
JP 2009-256630 A 11/2009
JP 2012-41421 A 3/2012
JP 2014-173007 A 9/2014
JP 2018-95765 A 6/2018
JP 2019-041872 A 3/2019
JP 2019-41874 A 3/2019
WO 2019/044755 A1 3/2019
WO 2020/175278 A1 9/2020

OTHER PUBLICATIONS

Japanese Office Action dated Oct. 3, 2023 in Japanese Application No. 2022-553738.
International Search Report dated Nov. 22, 2021 in Application No. PCT/JP2021/032923.
Written Opinion dated Nov. 22, 2021 in Application No. PCT/JP2021/032923.
International Preliminary Report on Patentability dated Mar. 28, 2023 with a Translation of the Written Opinion of the International Searching Authority in Application No. PCT/JP2021/032923.
Communication issued Nov. 28, 2024 in Chinese Application No. 202180050426.6.

* cited by examiner

*Primary Examiner* — Terressa Boykin
(74) *Attorney, Agent, or Firm* — Sughrue Mion, PLLC

(57) ABSTRACT

An object of the present invention to provide an adhesive for an endoscope and a cured product of the adhesive, and an endoscope and a method for producing the endoscope. The adhesive is able to maintain sufficient adhesive strength even when exposed to high temperature for a long time in a state of being used for fixation of a member or subjected to powerful sterilization treatment with ozone water or the like and is suitable for use in fixing a member constituting the endoscope. The adhesive for an endoscope includes an epoxy resin, an epoxy resin curing component, and a radical scavenger.

8 Claims, 3 Drawing Sheets

ADHESIVE FOR ENDOSCOPE AND CURED PRODUCT THEREOF, AND ENDOSCOPE AND METHOD FOR PRODUCING THE SAME

CROSS-REFERENCE TO RELATED APPLICATIONS

This application is a Continuation of PCT International Application No. PCT/JP2021/032923 filed on Sep. 8, 2021, which claims priority under 35 U.S.C. § 119 (a) to Japanese Patent Application No. 2020-163597 filed in Japan on Sep. 29, 2020. Each of the above applications is hereby expressly incorporated by reference, in its entirety, into the present application.

BACKGROUND OF THE INVENTION

1. Field of the Invention

The present invention relates to an adhesive for an endoscope and a cured product of the adhesive, and an endoscope and a method for producing the endoscope.

2. Description of the Related Art

Endoscopes for examining body cavities, the digestive tract, the esophagus, and other parts of a human body are repeatedly used. Thus, a flexible tube constituting an insertion section of an endoscope is washed and disinfected with a chemical after each use. In particular, when an endoscope is inserted into a highly susceptible region, such as a bronchus, cleanliness at the level of sterilization higher than disinfection is required. Accordingly, endoscopes are required to have high durability sufficient to withstand repeated disinfection or sterilization treatment.

The insertion section of an endoscope is inserted into the body through the oral cavity or nasal cavity. To alleviate foreign body sensation and pain in patients during the insertion, the insertion section of an endoscope desirably has a smaller diameter. Thus, instead of bulky members such as screws, adhesives are mainly used to bond members constituting the insertion section.

Among the adhesives, epoxy adhesives are used to bond constituent members of endoscopes because they have high workability and cured products thereof are excellent in adhesiveness, heat resistance, moisture resistance, and other properties. Since an endoscope is repeatedly used over a long period of time, it is required that the state in which an endoscope member is fixed with an adhesive can be sufficiently maintained even if the endoscope is repeatedly used over a long period of time. That is, durability that allows the fixed state to be sufficiently maintained if the endoscope is immersed in an antiseptic solution or subjected to sterilization treatment is required.

For example, JP2019-41872A discloses a two-component adhesive for an endoscope, the adhesive being composed of a base resin including at least one epoxy resin selected from the group consisting of bisphenol A epoxy resins, bisphenol F epoxy resins, and phenol novolac epoxy resins and a curing agent including specific amounts of a compound that promotes curing and a particular polythiol compound. JP2019-41872A states that this adhesive has, in a state of being used for fixation of an endoscope member (a state of being a cured product), high resistance to an aqueous peracetic acid solution. WO2019/044755A discloses a two-component adhesive for an endoscope, the adhesive being composed of a base resin including at least one epoxy resin selected from the group consisting of bisphenol A epoxy resins, bisphenol F epoxy resins, and phenol novolac epoxy resins and a curing agent including a specific amount of tertiary amine compound. WO2019/044755A states that this adhesive has, in a state of being a cured product, high hydrogen peroxide plasma resistance.

SUMMARY OF THE INVENTION

Sterilization treatment using ozone water obtained by dissolving a trace amount of ozone (O3) in water has recently been performed as sterilization treatment of an endoscope. However, such ozone water generates strong active species such as hydroxy radicals, whose oxidizing power is stronger than that of hydrogen peroxide gas.

Studies by the present inventors have shown that when an endoscope is exposed to heat generated from, for example, a light source of illumination built in the endoscope for a long time during use, a cured product of an epoxy adhesive is softened to take in oxygen, and radicals derived from the oxygen deteriorate the cured product, so that the state of an endoscope member fixed with the adhesive cannot be sufficiently maintained. Therefore, an adhesive for an endoscope is required to be highly heat resistant (less easily deteriorated if heated for a long time) in a state of being used for fixation of an endoscope member.

An object of the present invention to provide an adhesive for an endoscope and a cured product of the adhesive. The adhesive is able to maintain sufficient adhesive strength even when exposed to high temperature for a long time in a state of being used for fixation of a member or subjected to powerful sterilization treatment with ozone water or the like and is suitable for use in fixing a member constituting the endoscope. Another object of the present invention is to provide an endoscope that has the cured product as a member for fixing a member constituting the endoscope and that is less likely to suffer performance degradation even if used for a long time in a state of being heated at a high temperature around or higher than the glass transition temperature or subjected to powerful sterilization treatment with ozone water or the like. Still another object of the present invention is to provide a method for producing the endoscope by using the adhesive for an endoscope.

In view of the foregoing problems, the present inventors have conducted intensive studies and found that when a specific curing agent is used as a curing component to be combined with a base epoxy resin in an epoxy adhesive, and a compound having a specific structure and radical scavenging ability is further used in the epoxy adhesive, the fixed state of members joined using the adhesive can be sufficiently maintained if subjected to powerful sterilization treatment with ozone water or the like or heated for a long time. The present invention has been completed by further conducting studies based on these findings.

The above objects have been achieved by the following means.

<1>

An adhesive for an endoscope includes components (A) to (C) below.

Component (A): an epoxy resin

Component (B): an epoxy resin curing component

Component (C): a radical scavenger

The component (A) includes at least one of a bisphenol A epoxy resin, a bisphenol F epoxy resin, or a phenol novolac epoxy resin, the component (B) includes at least one of a phosphorus-containing compound, a polythiol compound, a dicyandiamide compound, a phenol compound, a polyamine compound having an unsubstituted amino group, an acid anhydride compound, or an imidazole compound, and the component (C) includes at least one of components (C-1) to (C-7) below. Component (C-1): a compound represented by general formula (C-1) below Component (C-2): a compound represented by general formula (C-2) below Component (C-3): a compound represented by formula (C-3) below Component (C-4): a compound represented by general formula (C-4) below Component (C-5): a compound represented by general formula (C-5) below Component (C-6): a compound having a structure represented by general formula (C-6) below Component (C-7): a compound having a structure represented by general formula (C-7) below general formula (C-1)

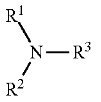

In the formula, $R^1$ and $R^2$ each represent a hydrogen atom, an aliphatic group, an acyl group, an aliphatic oxycarbonyl group, an aromatic oxycarbonyl group, an aliphatic sulfonyl group, or an aromatic sulfonyl group, and $R^3$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group. $R^1$ and $R^2$, $R^2$ and $R^3$, or $R^1$ and $R^3$ may be bonded to each other to form a five- to seven-membered ring but do not form a piperidine skeleton. $R^1$ and $R^2$ are not simultaneously hydrogen atoms and have a total of 7 or more carbon atoms. $R^1$, $R^2$ and $R^3$ include no unsubstituted amino groups.

general formula (C-2)

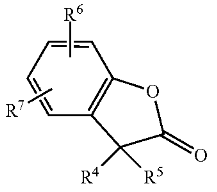

In the formula, $R^4$ to $R^7$ each represent a hydrogen atom, an alkyl group having 1 to 20 carbon atoms, or an aryl group having 6 to 15 carbon atoms.

formula (C-3)

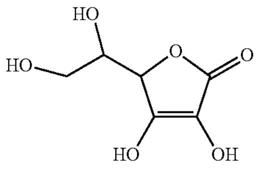

general formula (C-4)

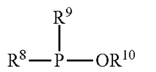

In the formula, $R^8$ and $R^9$ each represent an alkyl group, an aryl group, an alkoxy group, an aryloxy group, or a halogen atom, $R^{10}$ represents an alkyl group or an aryl group. At least two of the $R^8$, $R^9$ and $R^{10}$ may be linked to each other via a divalent or higher valent group or a single bond.

$R^{11}—S—R^{12}$ general formula (C-5)

In the formula, $R^{11}$ and $R^{12}$ each represent an alkyl group.

general formula (C-6)

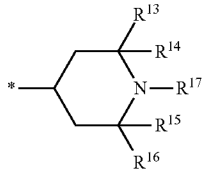

In the formula, $R^{13}$ to $R^{16}$ each represent a hydrogen atom or an alkyl group having 1 to 12 carbon atoms. $R^{17}$ represents a hydrogen atom, an alkyl group having 1 to 18 carbon atoms or $OR^{18}$. $R^{18}$ represents a hydrogen atom or an alkyl group having 1 to 20 carbon atoms. * represents a bonding site. $R^{13}$ to $R^{16}$ are not simultaneously hydrogen atoms.

general formula (C-7)

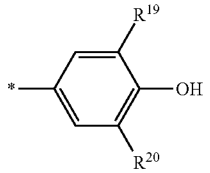

In the formula, $R^{19}$ and $R^{20}$ each represent a hydrogen atom, an alkyl group having 1 to 12 carbon atoms, or an aralkyl group having 7 to 36 carbon atoms. * represents a bonding site.

<2>

In the adhesive for an endoscope according to <1>, the component (C) includes at least one of the component (C-6) or the component (C-7).

<3>

In the adhesive for an endoscope according to <1> or <2>, the component (C) includes the component (C-6).

<4>

In the adhesive for an endoscope according to any one of <1> to <3>, the component (C-6) includes at least one of a component (C-6-1) below or a component (C-6-2) below. Component (C-6-1): a compound represented by general formula (C-6-1) below Component (C-6-2): a compound having a constituent represented by general formula (C-6-2) below general formula (C-6-1)

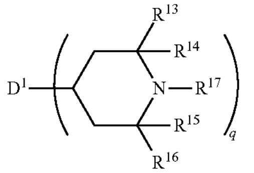

-continued general formula (C-6-2)

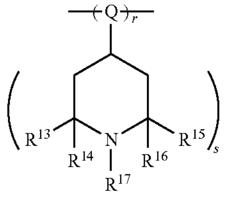

In the formula, $R^{13}$ to $R^{17}$ respectively have the same definitions as $R^{13}$ to $R^{17}$ in general formula (C-6). q represents an integer of 2 or greater, and $D^1$ represents a q-valent linking group. r represents an integer. Q represents an (s+2)-valent linking group. s represents 1 or 2.

<5>

In the adhesive for an endoscope according to any one of <1> to <4>, the component (C-7) includes at least one of a component (C-7-1) below or a component (C-7-2) below. Component (C-7-1): a compound represented by general formula (C-7-1) below Component (C-7-2): a compound represented by general formula (C-7-2) below general formula (C-7-1)

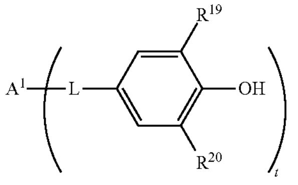

general formula (C-7-2)

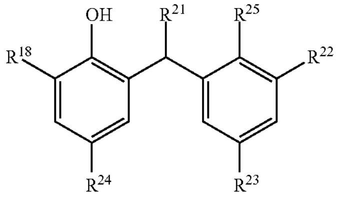

In the formula, $R^{19}$ and $R^{20}$ respectively have the same definitions as $R^{19}$ and $R^{20}$ in general formula (C-7). L represents a single bond or a divalent linking group. t represents an integer of 2 to 4, and $A^1$ represents a divalent to tetravalent linking group. $R^{21}$ to $R^{24}$ each have the same definition as $R^{19}$. $R^{25}$ represents a reactive organic substituent.

<6>

A cured product is obtained by curing the adhesive for an endoscope according to any one of <1> to <5>.

<7>

An endoscope includes a member fixed with the cured product according to <6>.

<8>

A method for producing an endoscope includes fixing a member by using the adhesive for an endoscope according to any one of <1> to <5>.

In the description of the present invention, the expression "to" is meant to include the numerical values before and after "to" as the lower and upper limits.

In this specification, substituents (as well as linking groups) not explicitly stated as substituted or unsubstituted may have any substituent as long as the desired effects are produced. Examples of such a substituent include substituents T given later. This also applies to compounds not explicitly stated as substituted or unsubstituted.

In this specification, when the number of carbon atoms of a group is specified, the number of carbon atoms means the number of carbon atoms of the whole group. That is, when the group further has a substituent, the number of carbon atoms means the number of carbon atoms of the whole including the substituent.

The adhesive for an endoscope according to the present invention can maintain sufficient adhesive strength even if exposed to high temperature for a long time in a state of being used for fixation of an endoscope member or subjected to powerful sterilization treatment with ozone water or the like. The cured product according to the present invention has high heat resistance and also has high resistance to powerful sterilization treatment with ozone water or the like. In addition, the endoscope according to the present invention is less likely to suffer performance degradation even if used under high-heat conditions for a long time or subjected to sterilization treatment with ozone water or the like. Furthermore, the method for producing an endoscope according to the present invention can provide an endoscope that is less likely to suffer performance degradation even if used under high-heat conditions for a long time or subjected to sterilization treatment with ozone water or the like.

DESCRIPTION OF THE PREFERRED EMBODIMENTS

Adhesive for Endoscope

Figure 1:
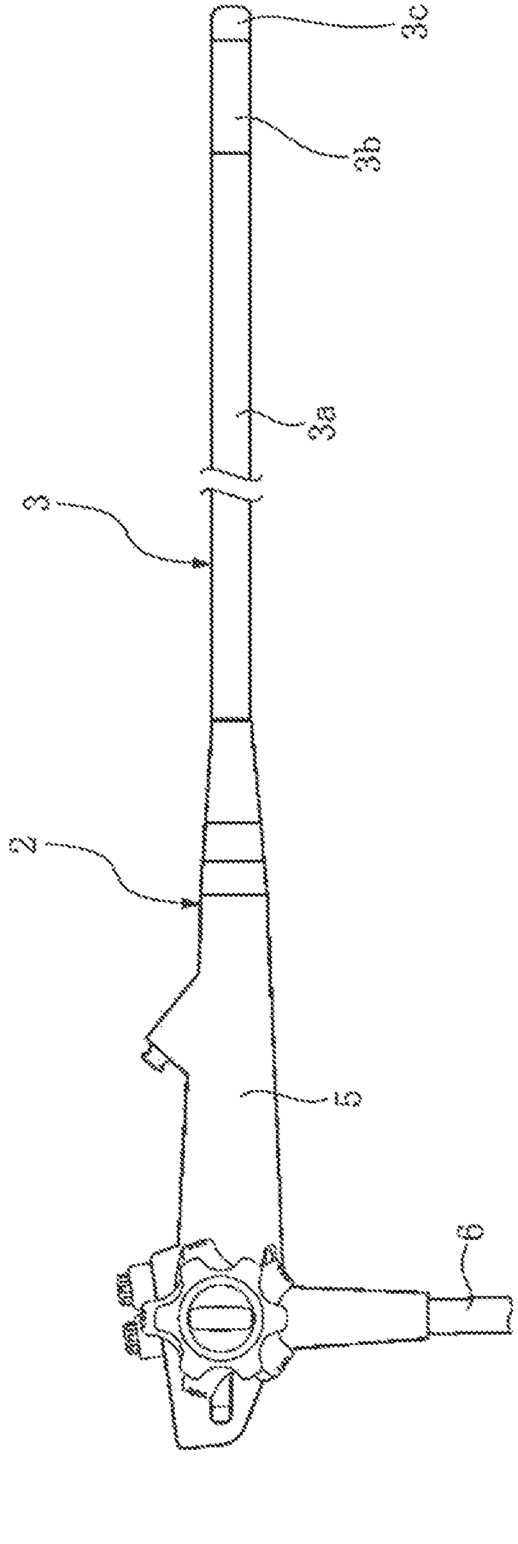
FIG. 1 is an external view illustrating a configuration of an endoscope according to an embodiment of the present invention.

An adhesive for an endoscope according to a preferred embodiment of the present invention will be described.

The adhesive for an endoscope according to the present invention (hereinafter also referred to as "the adhesive according to the present invention") includes the following components (A) to (C):

Component (A): an epoxy resin;

Component (B): an epoxy resin curing component; and

Component (C): a radical scavenger.

The component (A) is a base resin of the adhesive, and the component (B) is a curing component that reacts with the epoxy resin to cure the adhesive. The adhesive according to the present invention contains, in addition to the base resin and the curing component, a radical scavenger, that is, the component (C). The components (A) to (C) are components including specific compounds as described below.

The adhesive according to the present invention may be in any form as long as the above components are included. For example, the adhesive for an endoscope according to the present invention may contain a mixture of the components (A) to (C) (one-component type) or may include the components (A) to (C) with one of the components (A) to (C) being separated from the other components (two-component type). Alternatively, the adhesive for an endoscope according to the present invention may include the components (A) to (C) with the components (A) to (C) being separated from each other (three-component type). Any of these types are included in the adhesive according to the present invention.

When the contents of the components in the adhesive are described in this specification or the contents of the components in the adhesive are specified in the present invention, it is meant, in the cases of forms such as the two-component type and the three-component type, that the components (A) to (C) are mixed together at the point of use such that each component in the mixture satisfies the desired content described below. That is, the contents of the components (A) to (C) need not satisfy the contents described in this specification in a state where the components are separated. It means that in the cases of forms such as the two-component type and the three-component type, the contents described in this specification are satisfied when the components (A) to (C) are mixed together at the point of use.

When the adhesive for an endoscope according to the present invention is of one-component type, or when the adhesive is of two-component type or other type in which components that can react with each other are mixed together (e.g., an epoxy resin and a curing agent therefor are mixed together), the adhesive is preferably stored at a low temperature at which practically no reaction occurs, in order to keep the components stably maintained with no reaction occurring or with reaction sufficiently inhibited between the components. For example, the adhesive can be stored at −20° C. or lower, and is stored preferably at −30° C. or lower, more preferably at −40° C. or lower, still more preferably at −50° C. or lower. If necessary, the adhesive can be stored in darkness.

The adhesive according to the present invention can include, for example, a solvent, a plasticizer, an adhesion improver (e.g., a silane coupling agent), a surfactant, a colorant (e.g., a pigment or a dye), a weathering agent, an antioxidant, a heat stabilizer, a lubricant, an antistatic agent, a whitener, a release agent, a conductive agent, a viscosity regulator, a filler (e.g., silica or calcium carbonate), a thixotropy-imparting agent, a diluent, and a flame retardant, as long as the advantageous effects of the present invention are not impaired.

A cured product obtained by curing the adhesive according to the present invention can maintain sufficient adhesive strength even if exposed to high temperature for a long time or subjected to powerful sterilization treatment with ozone water or the like. Although the reason for this is not clear, it can be attributed to the combined effect of the following and other factors: the component (C) efficiently scavenges radicals trapped in the cured product and radicals generated upon the sterilization treatment to effectively inhibit the reaction of the radicals, in other words, the component (C) is uniformly dispersed in the cured product obtained by curing the component (A) with a specific curing component (the component (B)) and efficiently scavenges radicals.

The adhesive according to the present invention is suitable for fixation of various members (endoscope-constituting members) constituting an endoscope. That is, the adhesive according to the present invention is suitably used to bond (join) an endoscope-constituting member to another constituent member of the endoscope to fix them. The adhesive used to fix the endoscope-constituting member becomes a cured product and constitutes an adhesive joint of the endoscope.

The member fixed using the adhesive according to the present invention is not particularly limited, and preferred examples include metal members, glass members, and resin members. The "fixing" of an endoscope-constituting member is performed by bonding the endoscope-constituting member to another member (support member) constituting the endoscope. The support member may be a tube wall or the like of the endoscope or an immovable member fixed to the tube wall or the like, or may be a member whose relative position in the endoscope can be moved like a tube. In the present invention, the term "fixing" is meant to include filling, that is, sealing, a space between an endoscope-constituting member and a support member to be incorporated with the endoscope-constituting member with a cured product of an adhesive.

The components constituting the adhesive according to the present invention will be described below.

Component (A)

The adhesive according to the present invention includes an epoxy resin, and the epoxy resin includes at least one of a bisphenol A epoxy resin, a bisphenol F epoxy resin, or a phenol novolac epoxy resin. The adhesive according to the present invention may include one or more epoxy resins selected from the group consisting of bisphenol A epoxy resins, bisphenol F epoxy resins, and phenol novolac epoxy resins.

The proportion of the total amount of bisphenol A epoxy resin, bisphenol F epoxy resin, and phenol novolac epoxy resin relative to the total amount of epoxy resin included in the adhesive according to the present invention is preferably 70 mass % or more, preferably 80 mass % or more, more preferably 90 mass % or more. More preferably, the epoxy resin included in the adhesive according to the present invention is at least one of a bisphenol A epoxy resin, a bisphenol F epoxy resin, or a phenol novolac epoxy resin.

The epoxy equivalent of the epoxy resin included in the adhesive according to the present invention is preferably 10 to 1,000, more preferably 50 to 500, still more preferably 80 to 400, particularly preferably 100 to 300. The epoxy resin included in the adhesive according to the present invention typically has two or more epoxy groups in one molecule.

The epoxy equivalent is a value obtained by dividing the mass-average molecular weight of an epoxy compound by the number of moles of epoxy groups of the epoxy compound.

The bisphenol A epoxy resin that can be used in the adhesive according to the present invention is not particularly limited, and a wide range of bisphenol A epoxy resins commonly used as base resins of epoxy adhesives can be used. Preferred specific examples include bisphenol A diglycidyl ethers (jER825, jER828, and jER834 (trade names) manufactured by Mitsubishi Chemical Corporation) and bisphenol A propoxylate diglycidyl ethers (manufactured by Sigma-Aldrich).

The bisphenol F epoxy resin that can be used in the adhesive according to the present invention is not particularly limited, and a wide range of bisphenol F epoxy resins commonly used as base resins of epoxy adhesives can be used. Preferred specific examples include bisphenol F diglycidyl ethers (trade name: EPICLON 830, manufactured by DIC Corporation) and 4,4'-methylenebis(N,N-diglycidylaniline).

The phenol novolac epoxy resin that can be used in the adhesive according to the present invention is not particularly limited, and a wide range of phenol novolac epoxy resins commonly used as base resins of epoxy adhesives can be used. Such a phenol novolac epoxy resin is marketed, for example, by Sigma-Aldrich under the product number 406775.

The content of the epoxy resin included in the adhesive according to the present invention is preferably 5 mass % or more, more preferably 10 mass % or more, more preferably 20 mass % or more, more preferably 30 mass % or more, more preferably 40 mass % or more, still more preferably 50 mass % or more. The content of the epoxy resin is preferably 99 mass % or less, more preferably 98 mass % or less, more preferably 97 mass % or less, still more preferably 96 mass % or less.

Component (B)

The adhesive according to the present invention includes, as the component (B), at least one of a phosphorus-containing compound, a polythiol compound, a dicyandiamide compound, a phenol compound, a polyamine compound having an unsubstituted amino group (—$NH_2$), an acid anhydride, or an imidazole compound. In the adhesive according to the present invention, the phosphorus-containing compound, the polythiol compound, the dicyandiamide compound, the phenol compound, the polyether polyamine compound, the acid anhydride compound, and the imidazole compound may be used alone or in combination of two or more.

From the viewpoint of further improving the sterilization resistance, the adhesive according to the present invention preferably includes a polyether polyamine compound as the component (B).

(1) Phosphorus-Containing Compound

As the phosphorus-containing compound used in the present invention, a wide range of phosphorus-containing compounds commonly used as curing accelerators for epoxy resins can be used. However, a component (C-4), which will be described later, is not included in the phosphorus-containing compound. The phosphorus-containing compound is, for example, a tertiary phosphine compound or tetra-substituted phosphonium tetra-substituted borate.

The tertiary phosphine compound is, for example, a phosphine compound in which a total of three alkyl and aryl groups are bonded to a phosphorus atom. The alkyl group may be linear, branched, or cyclic, and is preferably an alkyl group having 1 to 20 carbon atoms, more preferably an alkyl group having 1 to 10 carbon atoms, still more preferably an alkyl group having 1 to 5 carbon atoms. Specific examples of the alkyl group include methyl, ethyl, propyl, butyl, t-butyl, and cyclohexyl. The number of carbon atoms of the aryl group is preferably 6 to 20, more preferably 6 to 10. Specific examples of the aryl group include phenyl and naphthyl, and phenyl is preferred. The aryl group may have a substituent, and specific examples of the substituent include the above alkyl groups.

The phosphine compound in which a total of three alkyl and aryl groups are bonded to a phosphorus atom is preferably a triarylphosphine, a trialkylphosphine, or a monoalkyldiarylphosphine.

Specific examples of the triarylphosphine include triphenylphosphine, tris(4-methylphenyl)phosphine, tris(4-ethylphenyl)phosphine, tris(4-propylphenyl)phosphine, tris(4-butylphenyl)phosphine, tris(2,4-dimethylphenyl)phosphine, and tris(2,4,6-trimethylphenyl)phosphine.

Specific examples of the trialkylphosphine include tributylphosphine, trioctylphosphine, tricyclohexylphosphine, and triisobutylphosphine.

Specific examples of the monoalkyldiarylphosphine include methyldiphenylphosphine, ethyldiphenylphosphine, hexyldiphenylphosphine, and cyclohexyldiphenylphosphine.

The tetra-substituted phosphonium tetra-substituted borate is, for example, a tetraarylphosphonium tetraarylborate or a tetraalkylphosphonium tetraalkylborate. The aryl group of the tetraarylphosphonium tetraarylborate and the alkyl group of the tetraalkylphosphonium tetraalkylborate may be alkyl and aryl groups that can be used in the phosphine compound in which a total of three alkyl and aryl groups are bonded to a phosphorus atom.

Specific examples of the tetraarylphosphonium tetraarylborate include tetraphenylphosphonium tetraphenylborate, tetraphenylphosphonium tetra-p-tolylborate, and p-tolyltriphenylphosphonium tetra-p-tolylborate.

Specific examples of the tetraalkylphosphonium tetraalkylborate include tetrabutylphosphonium tetrabutylborate, tri-tert-butylmethylphosphonium tetrabutylborate, and di-tert-butyldimethylphosphonium tetrabutylborate.

In the adhesive according to the present invention, the triarylphosphine is preferred, and in particular, triphenylphosphine and tris(4-methylphenyl)phosphine are preferred.

(2) Polythiol Compound

As the polythiol compound used in the present invention, a wide range of polythiol compounds commonly used as curing accelerators for epoxy resins can be used. For example, a compound having at least two partial structures represented by general formula (S1) below or at least two partial structures represented by general formula (S2) below can be used. A polythiol compound having a structure with 3 to 10 (preferably 3 to 6) partial structures represented by general formula (S1) below or 3 to 10 (preferably 3 to 6) partial structures represented by general formula (S2) below advantageously provides a cured product with an increased crosslink density and further improved sterilization resistance. A polythiol compound having a structure with two partial structures represented by general formula (S1) below or two partial structures represented by general formula (S2) below advantageously provides a relatively flexible cured product.

general formula (S1)

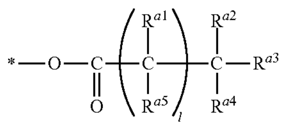

general formula (S2)

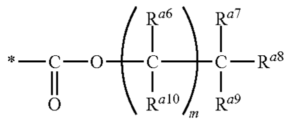

In general formula (S1), one of $R^{a1}$ to $R^{a5}$ represents a sulfanyl group (thiol group), the others each independently represent a hydrogen atom, an alkyl group having 1 to 10 carbon atoms, or an aryl group having 6 to 14 carbon atoms, and 1 represents an integer of 0 to 2. When 1 is 2, two $R^{a1}$'s may be the same or different, and two $R^{a5}$'s may be the same or different. * represents a bonding site in the polythiol compound.

In general formula (S2), one of $R^{a6}$ to $R^{a10}$ represents a sulfanyl group, the others each independently represent a hydrogen atom, an alkyl group having 1 to 10 carbon atoms, or an aryl group having 6 to 14 carbon atoms, and m represents an integer of 0 to 2. When m is 2, two $R^{a6}$'s may be the same or different, and two $R^{a10}$'s may be the same or different. * represents a bonding site in the polythiol compound.

The alkyl group having 1 to 10 carbon atoms may be linear or branched, and examples include methyl, ethyl, propyl, i-propyl, butyl, i-butyl, t-butyl, hexyl, and octyl. Of these, methyl and ethyl are preferred.

Specific examples of the aryl group having 6 to 14 carbon atoms include phenyl and naphthyl.

1 is preferably 0 or 1.

m is preferably 0 or 1.

The partial structure represented by general formula (S1) above is preferably a partial structure represented by general formula (S3) below.

general formula (S3)

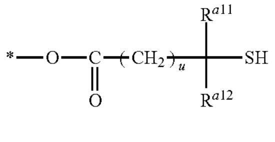

In general formula (S3), $R^{a11}$ and $R^{a12}$ each independently represent a hydrogen atom or an alkyl group having 1 to 10 carbon atoms, and u represents an integer of 0 to 2. * represents a bonding site in the polythiol compound.

At least one of $R^{a11}$ or $R^{a12}$ preferably represents an alkyl group having 1 to 10 carbon atoms.

The alkyl groups having 1 to 10 carbon atoms represented by $R^{a11}$ and $R^{a12}$ have the same definitions as the alkyl groups that can be employed as $R^{a1}$ in general formula (S1), and preferred ranges are also the same.

u is preferably 0 or 1, more preferably 1.

The polythiol compound is preferably an ester of a compound represented by general formula (S4) below and a polyfunctional alcohol.

general formula (S4)

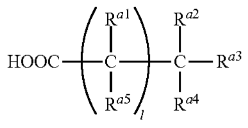

In general formula (S4), $R^{a1}$ to $R^{a5}$ and 1 respectively have the same definitions as $R^{a1}$ to $R^{a5}$ and 1 in general formula (S1) above, and preferred ranges are also the same.

The compound represented by general formula (S4) is preferably a compound represented by general formula (S5) below.

general formula (S5)

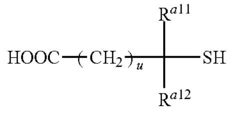

In general formula (S5), $R^{a11}$, $R^{a12}$, and u respectively have the same definitions as $R^{a11}$, $R^{a12}$, and u in general formula (S3) above, and preferred ranges are also the same.

Specific examples of the compound represented by general formula (S4) above include 2-mercaptopropionic acid, 3-mercaptopropionic acid, 3-mercaptobutanoic acid, 2-mercaptoisobutanoic acid, 3-mercapto-3-phenylpropionic acid, 3-mercaptoisobutyric acid, 2-mercapto-3-methylbutyric acid, 3-mercapto-3-methylbutyric acid, 3-mercaptovaleric acid, and 3-mercapto-4-methylvaleric acid.

The polyfunctional alcohol is preferably a bifunctional to decafunctional alcohol (polyol having 2 to 10 hydroxy groups), more preferably a bifunctional to octafunctional alcohol, particularly preferably a bifunctional to hexafunctional alcohol.

Specific examples of the polyfunctional alcohol include alkylene glycols (the number of carbon atoms of alkylene groups is preferably 2 to 10, and the alkylene groups may be linear or branched), diethylene glycol, glycerol, dipropylene glycol, trimethylolpropane, pentaerythritol, and dipentaerythritol.

Examples of the alkylene glycols include ethylene glycol, trimethylene glycol, 1,2-propane glycol, 1,2-butanediol, 1,3-butanediol, 2,3-butanediol, and tetramethylene glycol.

Preferred polyfunctional alcohols are alkylene glycols whose alkylene main chain has two carbon atoms, such as ethylene glycol, 1,2-propane glycol, and 1,2-butanediol, trimethylolpropane, and pentaerythritol.

Specific examples of polythiol compounds that can be used in the present invention will be given below, but the present invention is not limited to them.

Specific examples include bis(1-mercaptoethyl) phthalate, bis(2-mercaptopropyl) phthalate, bis(3-mercaptobutyl) phthalate, bis(3-mercaptoisobutyl) phthalate, ethylene glycol bis(3-mercaptopropionate), ethylene glycol bis(3-mercaptobutyrate), propylene glycol bis(3-mercaptobutyrate), diethylene glycol bis(3-mercaptobutyrate), tetraethylene glycol bis(3-mercaptopropionate), butanediol bis(3-mercaptobutyrate), octanediol bis(3-mercaptobutyrate), trimethylolpropane tris(3-mercaptobutyrate), trimethylolpropane tris (3-mercaptopropionate), dipentaerythritol hexakis (3-mercaptopropionate), pentaerythritol tetrakis(3-mercaptopropionate), pentaerythritol tetrakis(3-mercaptobutyrate), dipentaerythritol hexakis (3-mercaptobutyrate), ethylene glycol bis(2-mercaptopropionate), propylene glycol bis(2-mercaptopropionate), diethylene glycol bis(2-mercaptopropionate), butanediol bis(2-mercaptopropionate), octanediol bis(2-mercaptopropionate), trimethylolpropane tris(2-mercaptopropionate), pentaerythritol tetrakis(2-mercaptopropionate), dipentaerythritol hexakis (2-mercaptopropionate), ethylene glycol bis(3-mercaptoisobutyrate), propylene glycol bis(3-mercaptoisobutyrate), diethylene glycol bis(3-mercaptoisobutyrate), butanediol bis(3-mercaptoisobutyrate), octanediol bis(3-mercaptoisobutyrate), trimethylolpropane tris(3-mercaptoisobutyrate), pentaerythritol tetrakis(3-mercaptoisobutyrate), dipentaerythritol hexakis (3-mercaptoisobutyrate), ethylene glycol bis(2-mercaptoisobutyrate), propylene glycol bis(2-mercaptoisobutyrate), diethylene glycol bis(2-mercaptoisobutyrate), butanediol bis(2-mercaptoisobutyrate), octanediol bis(2-mercaptoisobutyrate), trimethylolpropane tris(2-mercaptoisobutyrate), pentaerythritol tetrakis(2-mercaptoisobutyrate), dipentaerythritol hexakis (2-mercaptoisobutyrate), ethylene glycol bis(4-mercaptovalerate), propylene glycol bis(4-mercaptoisovalerate), diethylene glycol bis(4-mercaptovalerate), butanediol bis(4-mercaptovalerate), octanediol bis(4-mercaptovalerate), trimethylolpropane tris(4-mercaptovalerate), pentaerythritol tetrakis(4-mercaptovalerate), dipentaerythritol hexakis (4-mercaptovalerate), ethylene glycol bis(3-mercaptovalerate), propylene glycol bis(3-mercaptovalerate), diethylene glycol bis(3-mercaptovalerate), butanediol bis(3-mercaptovalerate), octanediol bis(3-mercaptovalerate), trimethylolpropane tris(3-mercaptovalerate), pentaerythritol tetrakis(3-mercaptovalerate), dipentaerythritol hexakis (3-mercaptovalerate), 1,4-bis(3-mercaptobutyryloxy)

butane, 1,3,5-tris(3-mercaptobutyloxyethyl)-1,3,5-triazine-2,4,6(1H,3H,5H)-trione, and tris[(3-mercaptopropionyloxy) ethyl] isocyanurate.

From the viewpoint of less odor, a desired degree of viscosity, good compatibility with the epoxy resin serving as the component (A), and handleability of a mixture obtained by mixing the component (A) and the component (B), the polythiol compound is preferably at least one of 1,4-bis(3-mercaptobutyryloxy) butane, pentaerythritol tetrakis(3-mercaptobutyrate), 1,3,5-tris(3-mercaptobutyloxyethyl)-1,3,5-triazine-2,4,6(1H,3H,5H)-trione, trimethylolpropane tris(3-mercaptobutyrate), ethylene glycol bis(3-mercaptopropionate), tetraethylene glycol bis(3-mercaptopropionate), trimethylolpropane tris(3-mercaptopropionate), pentaerythritol tetrakis(3-mercaptopropionate), dipentaerythritol hexakis (3-mercaptopropionate), or tris[(3-mercaptopropionyloxy) ethyl] isocyanurate, more preferably at least one of 1,4-bis (3-mercaptobutyryloxy) butane, pentaerythritol tetrakis(3-mercaptobutyrate), 1,3,5-tris(3-mercaptobutyloxyethyl)-1,3,5-triazine-2,4,6(1H,3H,5H)-trione, or trimethylolpropane tris(3-mercaptobutyrate).

The molecular weight of the polythiol compound is not particularly limited, but is preferably 200 to 1,000, more preferably 300 to 800, because a polythiol compound having such a molecular weight is easily mixed with and less easily separated from the epoxy resin serving as the component (A) of the adhesive according to the present invention and a mixture obtained by mixing the component (A) and the component (B) is easy to handle, for example, less likely to drip or become uneven.

In the present invention, the polythiol compound may be a commercially available product, and specific examples include 1,4-bis(3-mercaptobutyryloxy) butane (trade name: Karenz MT BD1, manufactured by Showa Denko K.K.), pentaerythritol tetrakis(3-mercaptobutyrate) (trade name: Karenz MT PE1, manufactured by Showa Denko K.K.), 1,3,5-tris(3-mercaptobutyloxyethyl)-1,3,5-triazine-2,4,6 (1H,3H,5H)-trione (trade name: Karenz MT NR1, manufactured by Showa Denko K.K.), and trimethylolpropane tris (3-mercaptobutyrate) (trade name: TPMB, manufactured by Showa Denko K.K.).

(3) Dicyandiamide Compound

The dicyandiamide compound used in the present invention is a compound that has dicyandiamide, which is widely used as a curing accelerator for epoxy resins, as a basic skeleton and exhibits cure-accelerating action. Such compounds include, in addition to dicyandiamide ($(NH_2)_2C{=}NCN$) itself, compounds having a structure in which some of the hydrogen atoms of amino groups of dicyandiamide are substituted. Examples of commercially available dicyandiamide compounds include DICY7 and DICY15 (trade names, manufactured by Mitsubishi Chemical Corporation). In the adhesive according to the present invention, commercially available products manufactured by, for example, Tokyo Chemical Industry Co., Ltd. can also be used.

(4) Phenol Compound

The phenol compound used in the present invention is a compound widely used as a curing agent for epoxy resins and having a phenolic hydroxy group. The term “phenolic hydroxy group” refers to a hydroxy group bonded to a ring-forming carbon atom of an aromatic hydrocarbon ring.

The phenol compound used in the present invention is preferably a phenol resin, and specific examples of the phenol resin include HF-1M, DL-92, MEHC-7841-4S, and MEH-7000 and manufactured by Meiwa Plastic Industries, Ltd. and TD-2131 and TD-2106 manufactured by DIC Corporation (all are trade names).

(5) Polyamine Compound Having Unsubstituted Amino Group

The polyamine compound having an unsubstituted amino group is a compound having two or more unsubstituted amino groups ($-NH_2$) in one molecule. The polyamine compound is more preferably a primary polyamine compound (polyamine compound in which all amino groups are unsubstituted amino groups). In the adhesive according to the present invention, among polyamine compounds that exhibit curing action in epoxy adhesives, a wide range of compounds having two or more unsubstituted amino groups in one molecule can be used.

The number of amino groups (preferably unsubstituted amino groups) having active hydrogen in one molecule of the polyamine compound is preferably 2 to 10, more preferably 2 to 8, still more preferably 2 to 6, further more preferably 2 to 4, particularly preferably 2 or 3. In particular, at least one selected from the group consisting of diamine compounds and triamine compounds is suitable for use.

The active hydrogen equivalent (equivalent of active hydrogen of amino groups) of the polyamine compound is preferably 10 to 2,000, more preferably 20 to 1,000, still more preferably 30 to 900, further more preferably 40 to 800, yet more preferably 60 to 700, particularly preferably 65 to 600.

The active hydrogen equivalent is a value obtained by dividing the molecular weight of the polyamine compound by the number of moles of active hydrogen of amino groups of the polyamine compound (i.e., a molecular weight of one active hydrogen of an amino group in the polyamine compound).

The molecular weight of the polyamine compound is preferably 100 to 6,000, more preferably 100 to 3,000. When the polyamine compound is a polymer (e.g., when the polyamine compound has a polyoxyalkylene group described below), the molecular weight is a number-average molecular weight.

In the present invention, the number-average molecular weight is determined by gel permeation chromatography. The measurement method is as follows. As an apparatus, HLC-8320GPC (manufactured by Tosoh Corporation) is used. As a column, TOSOH TSKgel Super AWM-H (column size: 6.0 mm×15 cm) is used. As an eluent, N-methylpyrrolidone (NMP) (containing 10 mM of LiBr) is used. The measurement is performed at a flow rate of 0.35 mL/min and 40° C. The detection is performed with a differential refractive index detector (RI). Polystyrene standards are used to determine the molecular weight.

The polyamine compound preferably has a form in which two or more amino groups are bonded to each other through a group selected from the group consisting of aliphatic hydrocarbon groups, cyclic hydrocarbon groups, aromatic hydrocarbon groups, and heterocyclic groups or a combination thereof. These groups may have a heteroatom such as an oxygen atom, a nitrogen atom, or a sulfur atom (preferably an oxygen atom) in a carbon-carbon bond.

From the viewpoint of ozone water treatment resistance and heat resistance, it is also preferred that the polyamine compound do not include a heteroatom such as an oxygen atom, a nitrogen atom, or a sulfur atom (preferably an oxygen atom) in a carbon-carbon bond. In the case of the polyamine compound not including a heteroatom in a carbon-carbon bond, the group bonding the two or more amino groups to each other may be a chain aliphatic hydrocarbon group, and the chain aliphatic hydrocarbon group may be branched. The number of carbon atoms of such a chain aliphatic hydrocarbon group that may be branched is preferably 4 to 50, more preferably 4 to 12, still more preferably 6 to 12.

From the viewpoint of ozone water treatment resistance and heat resistance, the polyamine compound also preferably has, in its molecule, a chain alkylene group or an oxyalkylene structure, more preferably has a polyoxyalkylene structure.

The polyamine compound having a chain alkylene group is preferably an alkylenediamine compound. The polyamine compound having a polyoxyalkylene structure (hereinafter also referred to as the "polyether polyamine compound") is more preferably a polyoxyalkylenediamine compound or a polyoxyalkylenetriamine compound.

The chain alkylene group may be linear or branched, and the number of carbon atoms is preferably 1 to 20, more preferably 5 to 12. Specific examples of the alkylene group include methylene, ethylene, hexamethylene, 2,4,4-trimethylhexamethylene, 2-methylpentamethylene, and dodecamethylene.

The alkylene group of the oxyalkylene structure may be a linear alkylene group or a branched alkylene group. In the alkylene group of the oxyalkylene structure, the number of carbon atoms is preferably 1 to 10, more preferably 2 to 6, still more preferably 2 to 4.

The oxyalkylene structure is more preferably an oxyethylene group or an oxypropylene group.

When the polyamine compound serving as the component (B) has a polyoxyalkylene structure, a plurality of oxyalkylene groups constituting the polyoxyalkylene structure may be the same or different. The average number of repetitions of the oxyalkylene groups of the polyoxyalkylene structure is preferably 2 to 1,000, more preferably 3 to 500. The average number of repetitions is also preferably 2 to 100, also preferably 2 to 50, also preferably 2 to 35, also preferably 2 to 25. The polyamine compound serving as the component (B) may have a plurality of polyoxyalkylene structures.

From the viewpoint of ozone water treatment resistance and heat resistance, the polyamine compound also preferably has, in its molecule, a polyamide bond (—NH—CO—).

The polyamine compound having a polyamide bond (hereinafter also referred to as the "polyamide polyamine compound") is preferably a polyamide diamine compound.

The average number of amide bonds in one molecule of the polyamide polyamine compound is preferably 2 to 50, more preferably 5 to 30, still more preferably 5 to 20.

The linking group that links the plurality of amide bonds to each other is not particularly limited, and is, for example, a saturated or unsaturated aliphatic hydrocarbon group or an aromatic hydrocarbon group. When the polyamide polyamine compound has a plurality of linking groups each linking amide bonds to each other, the plurality of linking groups may be the same or different.

From the viewpoint of ozone water treatment resistance and heat resistance of the cured product obtained from the adhesive according to the present invention, the polyamine compound preferably has a polyoxyalkylene structure. When the polyamine compound is a compound having a polyoxyalkylene structure, it is presumed that even if degradation and decomposition of a crosslinked structure has occurred as a result of ozone water treatment, the cured product is less prone to internal cracking because the cured product has toughness, and the strength of the cured product is maintained. It is also presumed that even if a high temperature is applied, the flexible structure helps relax the stress at the time of thermal expansion or thermal contraction to reduce the possibility of cracking.

Specific examples of preferred polyamine compounds that can be used in the present invention are given below. The number attached to parentheses is the average number of repetitions of the repeating unit in the parentheses.

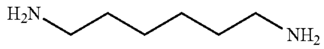

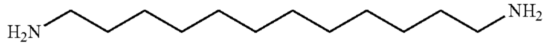

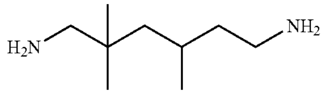

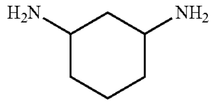

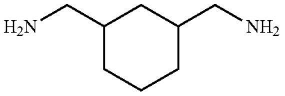

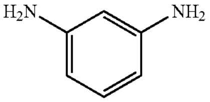

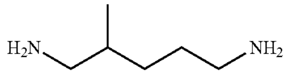

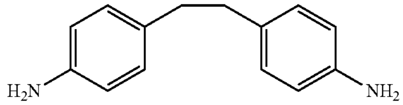

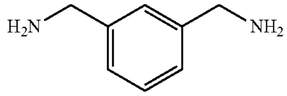

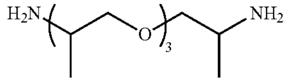

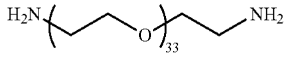

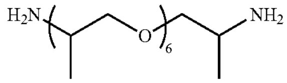

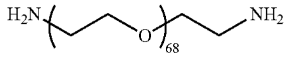

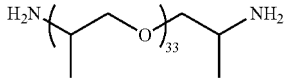

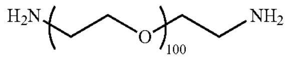

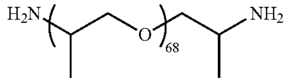

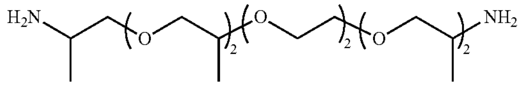

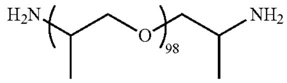

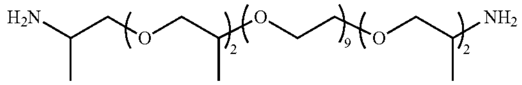

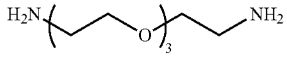

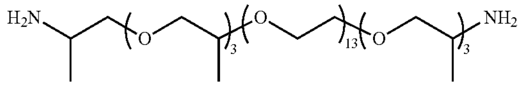

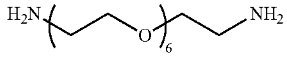

-continued
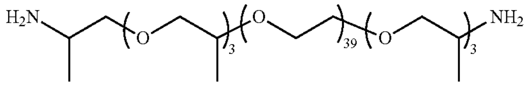
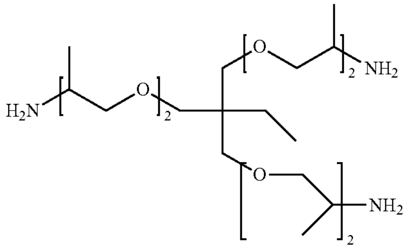
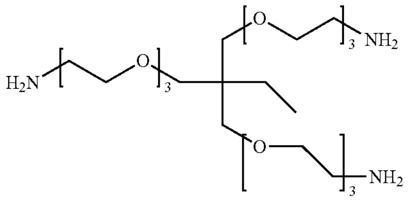
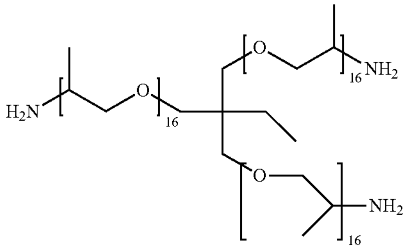
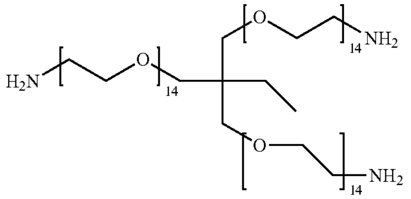
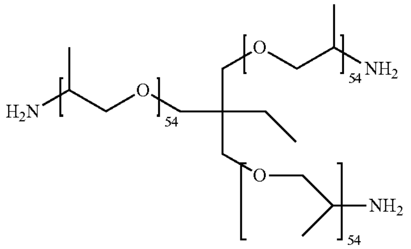
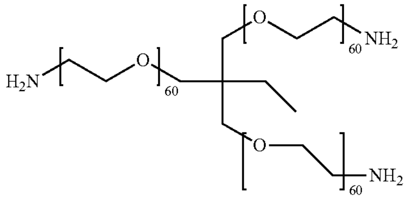
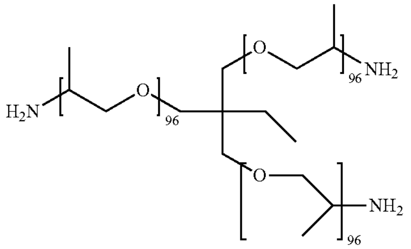
-continued
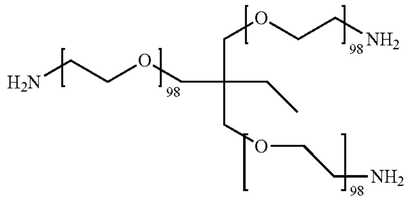
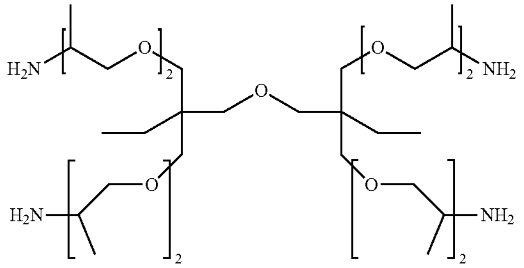
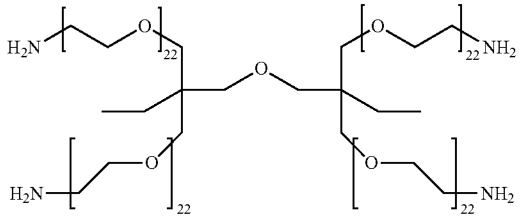
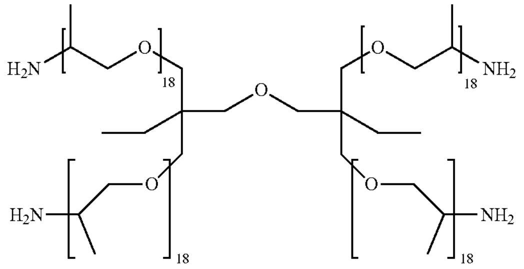
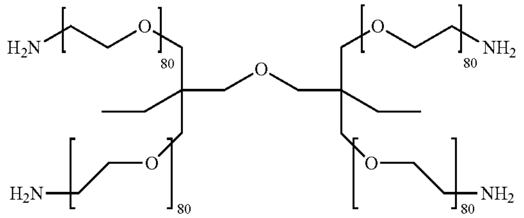
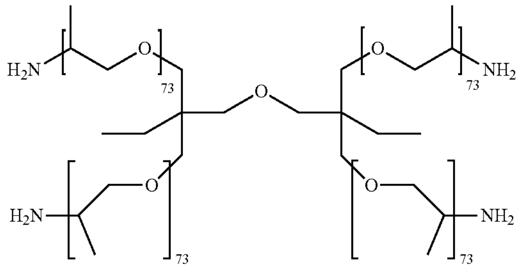
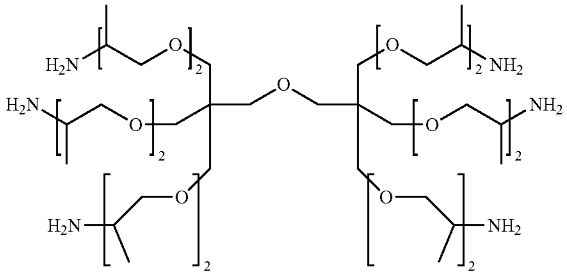

-continued
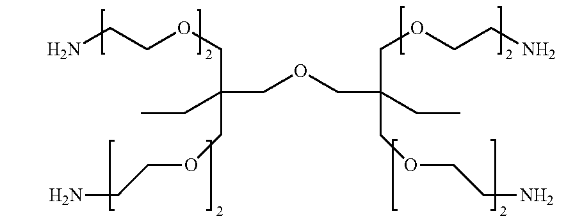
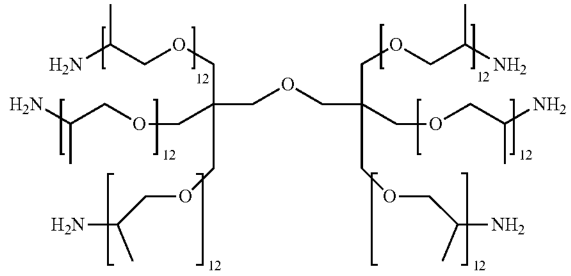
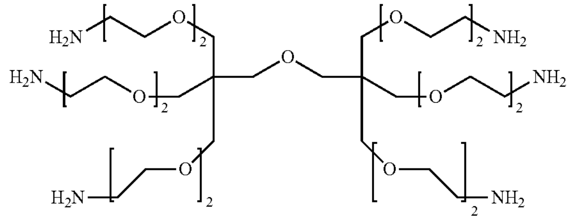
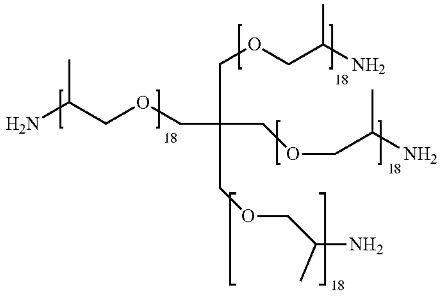
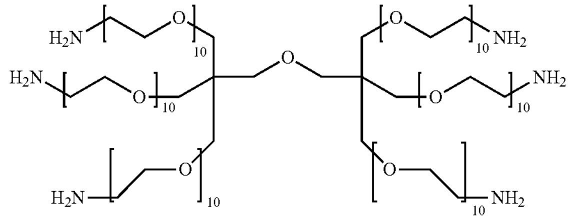
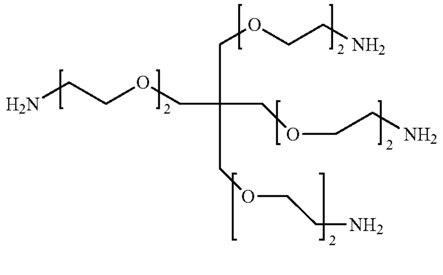
-continued
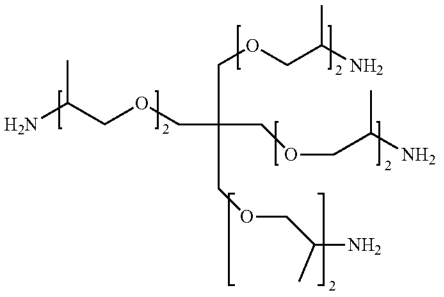
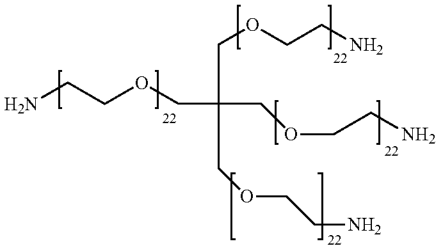
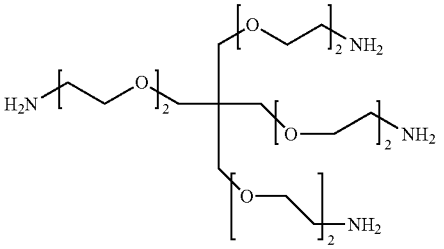
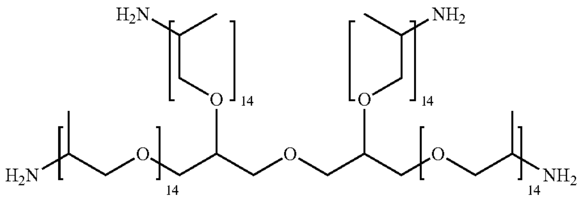
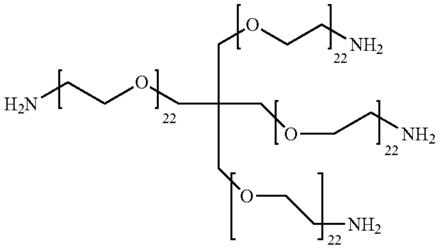
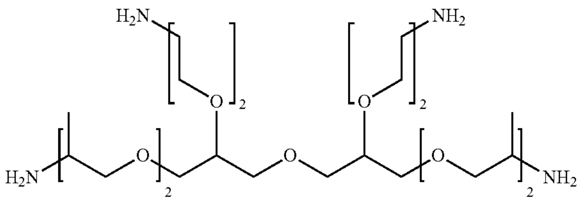
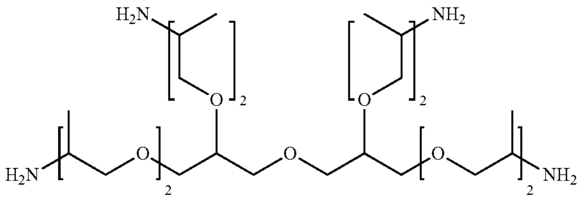

-continued

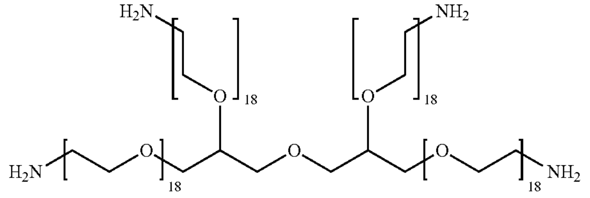

The above polyamine compounds can be synthesized by conventional methods.

Alternatively, commercially available products may be used. Examples of the commercially available products include Polyether Amine D230, Polyether Amine D400, and Polyether Amine T403 (trade names, manufactured by Mitsui Fine Chemicals, Inc.), JEFFAMIN ED-600 (trade name, manufactured by Huntsman Corporation), and HV953U (trade name, manufactured by Nagase ChemteX Corporation, polyamidoamine).

(6) Acid Anhydride Compound

In the present invention, "acid anhydride" means carboxylic anhydride.

The acid anhydride compound used in the present invention preferably includes an alicyclic dicarboxylic anhydride. The alicyclic dicarboxylic anhydride is a compound having a structure formed through dehydration condensation of carboxy groups at two adjacent carbon atoms constituting an aliphatic ring. The aliphatic ring is preferably a monocyclic five-membered ring or six-membered ring, more preferably a six-membered ring. The aliphatic ring may have one or more substituents. Among the substituents, two adjacent substituents may be linked to each other to form a ring. The ring formed through the linkage of the two substituents is preferably a monocyclic five-membered ring or six-membered ring, and it is also preferred that this ring form an acid anhydride group.

The acid anhydride compound used in the present invention may include one or more alicyclic dicarboxylic anhydrides.

The acid anhydride compound used in the present invention may include an acid anhydride compound other than the alicyclic dicarboxylic anhydrides. When the acid anhydride compound used in the present invention includes an alicyclic dicarboxylic anhydride, the proportion of the total amount of the alicyclic dicarboxylic anhydride in all acid anhydride compounds included in the acid anhydride compound used in the present invention is preferably 50 mass % or more, more preferably 70 mass % or more, still more preferably 80 mass % or more, particularly preferably 90 mass % or more. It is also preferred that every acid anhydride compound included in the acid anhydride compound used in the present invention be the alicyclic dicarboxylic anhydride.

The acid anhydride compound used in the present invention also preferably includes an acid anhydride compound represented by formula (I) below.

(I)

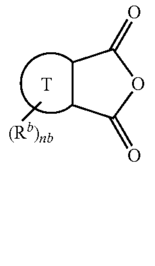

In formula (I), a ring T is a five-membered ring or a six-membered ring. The ring T may be an aliphatic ring or an aromatic ring. When the ring T is an aliphatic ring, it may be a saturated hydrocarbon ring or may have an unsaturated bond between ring-forming atoms.

$R^b$ represents an alkyl group, an alkoxy group, an acyl group, an alkoxycarbonyl group, an aryl group, or a carboxy group, and nb is an integer of 0 to 4.

The number of carbon atoms of the alkyl group represented by $R^b$ is preferably 1 to 10, more preferably 1 to 6, still more preferably 1 to 3, and further preferred is methyl or ethyl.

The number of carbon atoms of the alkoxy group represented by $R^b$ is preferably 1 to 10, more preferably 1 to 6, still more preferably 1 to 3, and further preferred is methoxy or ethoxy.

The number of carbon atoms of the acyl group represented by $R^b$ is preferably 1 to 30, more preferably 1 to 20, still more preferably 1 to 10. In the present invention, the term "acyl group" is meant to include an arylcarbonyl group.

The number of carbon atoms of the alkoxycarbonyl group represented by $R^b$ is preferably 1 to 30, more preferably 1 to 20, still more preferably 1 to 15. The alkoxy group constituting the alkoxycarbonyl group is preferably methoxy, ethoxy, or propoxy.

The number of carbon atoms of the aryl group represented by $R^b$ is preferably 6 to 20, more preferably 6 to 15, still more preferably 6 to 12, and further preferred is phenyl.

nb is preferably 0 or 1.

When nb is 2 or greater, two adjacent $R^b$'s may be linked to each other to form a fused ring together with the ring T. The ring formed through the linkage of two $R^b$'s is preferably a five-membered ring or a six-membered ring, more preferably a five-membered ring. This ring more preferably has an acid anhydride structure (—C(=O)—O—C(=O)—) formed by two ring-forming carbon atoms and a ring-forming oxygen atom sandwiched therebetween (i.e., a structure formed through dehydration condensation of two adjacent $R^b$'s that are both carboxy groups is preferred).

The acid anhydride compound represented by formula (I) has, in its molecule, preferably one to three acid anhydride structures, more preferably one or two acid anhydride structures, still more preferably one acid anhydride structure. The molecular weight of the acid anhydride compound represented by formula (I) is preferably 90 to 800, more preferably 100 to 300.

The acid anhydride compound used in the present invention may include one or more acid anhydride compounds represented by formula (I).

When the acid anhydride compound used in the present invention includes an acid anhydride compound represented by formula (I), the acid anhydride compound may include an acid anhydride compound other than the acid anhydride compound represented by formula (I). When the acid anhydride compound includes an acid anhydride compound represented by formula (I), the proportion of the total amount of the acid anhydride compound represented by formula (I) in all the acid anhydride compounds included in the acid anhydride compound used in the present invention is preferably 50 mass % or more, more preferably 70 mass % or more, still more preferably 80 mass % or more, particularly preferably 90 mass % or more. It is also preferred that every acid anhydride compound included in the acid anhydride compound used in the present invention be the acid anhydride compound represented by formula (I).

The acid anhydride compound used in the present invention also preferably includes at least one acid anhydride compound selected from the group consisting of phthalic anhydride, trimellitic anhydride, pyromellitic dianhydride, benzophenonetetracarboxylic anhydride, ethylene glycol bisanhydrotrimellitate, glycerol trisanhydrotrimellitate, maleic anhydride, tetrahydrophthalic anhydride, methyltetrahydrophthalic anhydride, methylbutenyltetrahydrophthalic anhydride, hexahydrophthalic anhydride, methylhexahydrophthalic anhydride, succinic anhydride, octenylsuccinic anhydride, dodecenylsuccinic anhydride, methylcyclohexenedicarboxylic anhydride, methylbicyclo[2.2.1]heptane-2,3-dicarboxylic anhydride, and bicyclo[2.2.1]heptane-2,3-dicarboxylic anhydride (hereinafter, these acid anhydride compounds will be collectively referred to as acid anhydrides Z). That is, the acid anhydride compound used in the present invention preferably includes at least one acid anhydride compound selected from the group consisting of the acid anhydrides Z.

The acid anhydride compound used in the present invention more preferably includes an acid anhydride compound selected from the group consisting of trimellitic anhydride, hexahydrophthalic anhydride, methylhexahydrophthalic anhydride, succinic anhydride, methylbicyclo[2.2.1]heptane-2,3-dicarboxylic anhydride, bicyclo[2.2.1]heptane-2,3-dicarboxylic anhydride, benzophenonetetracarboxylic anhydride, glycerol trisanhydrotrimellitate, and octenylsuccinic anhydride.

When the acid anhydride compound used in the present invention includes an acid anhydride compound selected from the group consisting of the acid anhydrides Z, the acid anhydride compound used in the present invention may include an acid anhydride compound other than the acid anhydrides Z as long as the advantageous effects of the present invention are not impaired. When the acid anhydride compound used in the present invention includes an acid anhydride compound selected from the group consisting of the acid anhydrides Z, the proportion of the total amount of the acid anhydride compound selected from the group consisting of the acid anhydrides Z in all the acid anhydride compounds included in the acid anhydride compound used in the present invention is preferably 50 mass % or more, more preferably 70 mass % or more, still more preferably 80 mass % or more, particularly preferably 90 mass % or more. It is also preferred that every acid anhydride compound included in the acid anhydride compound used in the present invention be the acid anhydride compound selected from the group consisting of the acid anhydrides Z.

Specific examples of acid anhydride compounds that can be used in the present invention are given below, but these examples are not intended to limit the present invention.

AH-1

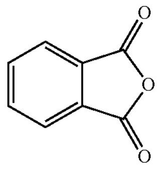

AH-2

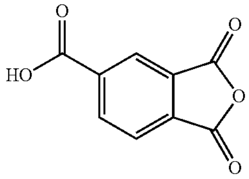

-continued

AH-3

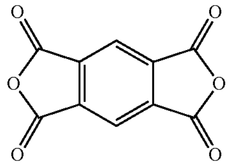

AH-4

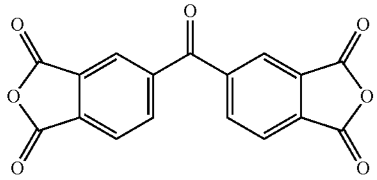

AH-5

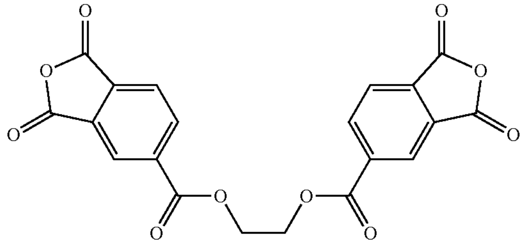

AH-6

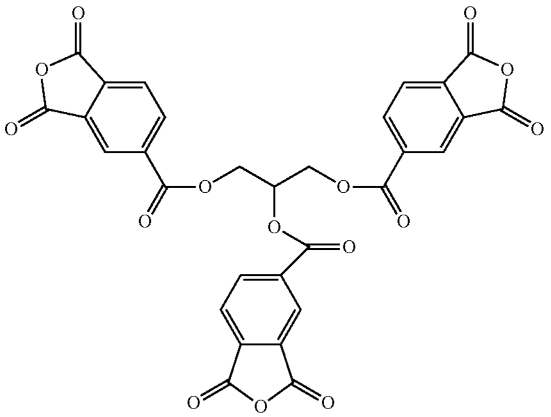

AH-7

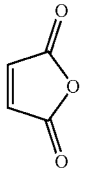

AH-8

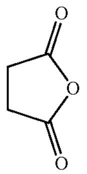

AH-9

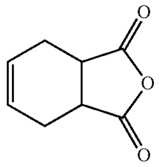

-continued

AH-10

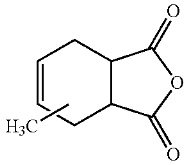

AH-11

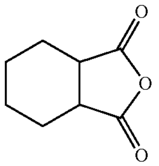

AH-12

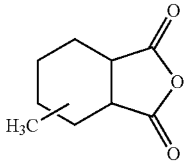

AH-13

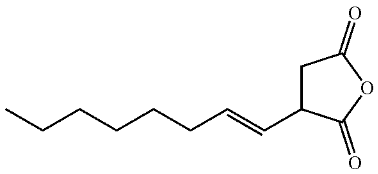

AH-14

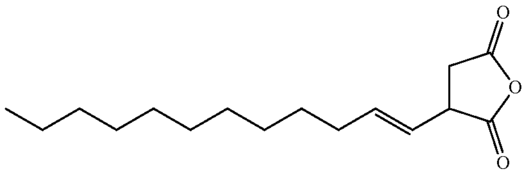

AH-15

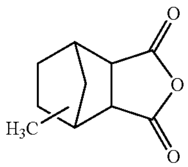

AH-16

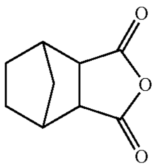

(7) Imidazole Compound

The imidazole compound used in the present invention preferably includes an imidazole compound represented by formula (II) below.

(II)

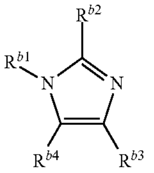

In formula (II), $R^{b1}$ represents a hydrogen atom or an alkyl group. The alkyl group represented by $R^{b1}$ may be a linear alkyl group, a branched alkyl group, or a cyclic alkyl group, and is preferably a linear alkyl group.

The alkyl group represented by $R^{b1}$ also preferably has a substituent, and examples of the substituent include a cyano group, aromatic hydrocarbon groups, and aromatic heterocyclic groups. These aromatic hydrocarbon groups and aromatic heterocyclic groups preferably have monocyclic structures. The monocyclic aromatic heterocyclic ring constituting such an aromatic heterocyclic group is preferably a five-membered ring or a six-membered ring, more preferably a triazine ring.

The number of carbon atoms of the alkyl group represented by $R^{b1}$ is preferably 1 to 20, more preferably 1 to 18, still more preferably 1 to 15, particularly preferably 1 to 12. When the alkyl group is a cyclic alkyl group, the lower limit of the number of carbon atoms is 3, preferably 4, more preferably 5.

Preferred examples of the alkyl group represented by $R^{b1}$ include a cyanoalkyl group and an aralkyl group. The cyanoalkyl group is a cyanoalkyl group having preferably 1 to 5 carbon atoms, more preferably 1 to 3 carbon atoms, and is particularly preferably cyanoethyl. The aralkyl group is an aralkyl group having preferably 7 to 20 carbon atoms, more preferably 7 to 15 carbon atoms, still more preferably 7 to 10 carbon atoms, and is particularly preferably benzyl.

$R^{b2}$, $R^{b3}$ and $R^{b4}$ represent a hydrogen atom, an alkyl group, or an aryl group.

The alkyl groups represented by $R^{b2}$, $R^{b3}$, and $R^{b4}$ may each be a linear alkyl group, a branched alkyl group, or a cyclic alkyl group, and are each preferably a linear alkyl group.

The number of carbon atoms of each of the alkyl groups represented by $R^{b2}$, $R^{b3}$, and $R^{b4}$ is preferably 1 to 20, more preferably 1 to 18, still more preferably 1 to 15, particularly preferably 1 to 12. When the alkyl group is a cyclic alkyl group, the lower limit of the number of carbon atoms is 3, preferably 4, more preferably 5.

Preferred specific examples of the alkyl groups represented by $R^{b2}$, $R^{b3}$, and $R^{b4}$ include methyl, ethyl, propyl, butyl, pentyl, hexyl, heptyl, octyl, 2-ethylhexyl, decyl, undecyl, dodecyl, heptadecyl, octadecyl, hydroxymethyl, and cyanoethyloxymethyl.

The number of carbon atoms of each of the aryl groups represented by $R^{b2}$, $R^{b3}$, and $R^{b4}$ is preferably 6 to 15, more preferably 6 to 12, and phenyl is particularly preferred.

The imidazole compound represented by formula (II) also preferably has a counterion. As used herein, "the imidazole compound represented by formula (II)" is meant to include a form in which the imidazole compound represented by formula (II) has a counterion. When the imidazole compound represented by formula (II) has a counterion, the ring-forming nitrogen atom of the compound represented by formula (II) is bonded to a hydrogen atom to be positively charged, and a counterion having a negative charge is bonded to the positive charge.

The counterion is not particularly limited, and the counterion is preferably derived from, for example, trimellitic acid, pyromellitic acid, cyanuric acid, hydrochloric acid, sulfuric acid, thiocyanic acid, or boric acid.

In the imidazole compound represented by formula (II), $R^{b1}$ is more preferably a hydrogen atom, benzyl, triazylethyl, or cyanoethyl. $R^{b2}$ is more preferably a hydrogen atom, a linear and unsubstituted alkyl group having 1 to 20 carbon atoms, or phenyl. $R^{b3}$ is more preferably a hydrogen atom, a linear and unsubstituted alkyl group having 1 to 20 carbon atoms (preferably 1 to 12 carbon atoms, more preferably 1 to 5 carbon atoms), hydroxymethyl, or cyanoethyloxymethyl. $R^{b4}$ is more preferably a hydrogen atom, hydroxymethyl, or cyanoethyloxymethyl.

The imidazole compound used in the present invention may include one or more imidazole compounds represented by formula (II).

When the imidazole compound used in the present invention includes an imidazole compound represented by formula (II), the imidazole compound used in the present invention may include an imidazole compound other than the imidazole compound represented by formula (II). When the imidazole compound used in the present invention includes an imidazole compound represented by formula (II), the proportion of the total amount of the imidazole compound represented by formula (II) in all the imidazole compounds included in the imidazole compound used in the present invention is preferably 50 mass % or more, more preferably 70 mass % or more, still more preferably 80 mass % or more, particularly preferably 90 mass % or more. It is also preferred that every imidazole compound included in the imidazole compound used in the present invention be the imidazole compound represented by formula (II).

The imidazole compound used in the present invention also preferably includes at least one imidazole compound selected from the group consisting of imidazole, 1-methylimidazole, 2-methylimidazole, 2-ethyl-4-methylimidazole, 2-undecylimidazole, 2-heptadecylimidazole, 2-phenylimidazole, 1-benzyl-2-methylimidazole, 1-cyanoethyl-2-methylimidazole, 1-cyanoethyl-2-ethyl-4-methylimidazole, 1-cyanoethyl-2-ethyl-4-undecylimidazole, 1-cyanoethyl-2-undecylimidazolium trimellitate, 2-phenyl-4,5-dihydroxymethylimidazole, 2-methylimidazolium isocyanurate, 2,4-diamino-6-[2-(2-methyl-1-imidazolyl)ethyl]-S-triazine, and 2-phenylimidazolium isocyanurate (hereinafter, these imidazole compounds are collectively referred to as imidazoles Z). That is, the imidazole compound used in the present invention preferably includes at least one imidazole compound selected from the group consisting of the imidazoles Z.

The imidazole compound used in the present invention more preferably includes an imidazole compound selected from the group consisting of imidazole, 1-methylimidazole, 2-methylimidazole, 2-heptadecylimidazole, 2-ethyl-4-methylimidazole, 1-benzyl-2-methylimidazole, 1-cyanoethyl-2-undecylimidazolium trimellitate, 2-phenylimidazolium isocyanurate, and 2,4-diamino-6-[2-(2-methyl-1-imidazolyl) ethyl]-S-triazine.

When the imidazole compound used in the present invention includes an imidazole compound selected from the group consisting of the imidazoles Z, this curing agent may include an imidazole compound other than the imidazoles Z as long as the advantageous effects of the present invention are not impaired. When the imidazole compound used in the present invention includes an imidazole compound selected from the group consisting of the imidazoles Z, the proportion of the total amount of the imidazole compound selected from the group consisting of the imidazoles Z in all the imidazole compounds included in the imidazole compound used in the present invention is preferably 50 mass % or more, more preferably 70 mass % or more, still more preferably 80 mass % or more, particularly preferably 90 mass % or more. It is also preferred that every imidazole compound included in the imidazole compound used in the present invention be the imidazole compound selected from the group consisting of the imidazoles Z.

Specific examples imidazole compounds that can be used in the present invention are given below, but these examples are not intended to limit the present invention. Among the following compounds, I-14 to I-17 each represent a form in which an imidazole compound has a counterion.

I-1

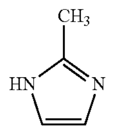

I-2

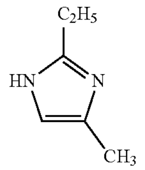

I-3

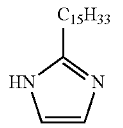

I-4

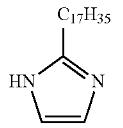

I-5

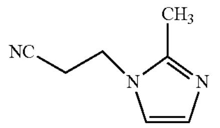

I-6

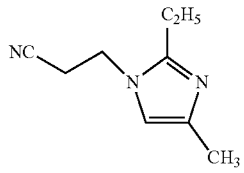

I-7

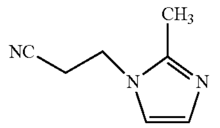

I-8

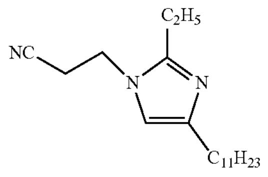

-continued

I-9

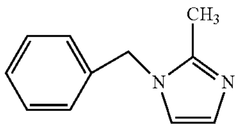

I-10

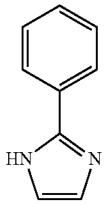

I-11

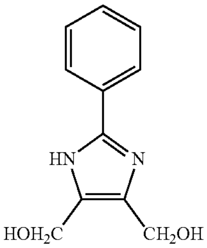

I-12

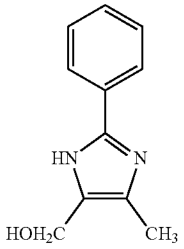

I-13

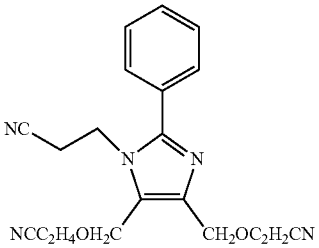

I-14

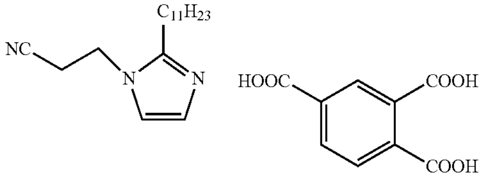

I-15

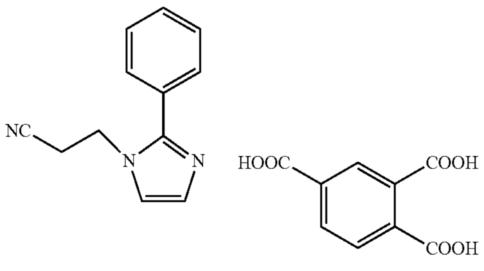

-continued

I-16

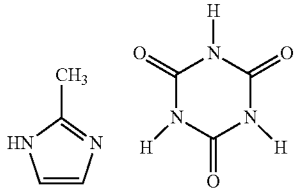

I-17

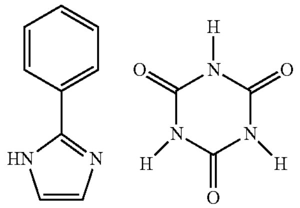

I-18

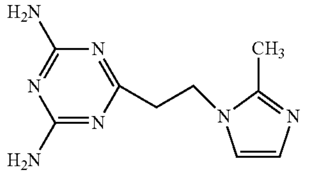

I-19

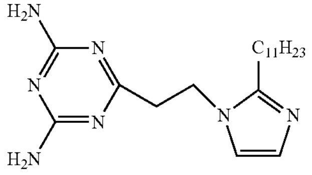

I-20

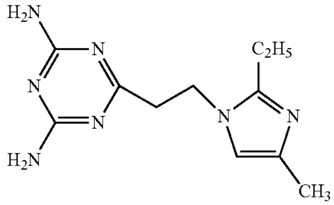

I-21

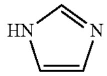

I-22

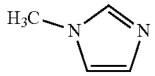

The proportion of the phosphorus-containing compound, the polythiol compound, the dicyandiamide compound, the phenol compound, the polyamine compound having an unsubstituted amino group, the acid anhydride compound, and the imidazole compound in the component (B) used in the adhesive according to the present invention is preferably 80 mass % or more, more preferably 90 mass % or more. It is also preferred that the component (B) be entirely constituted by one of the phosphorus-containing compound, the polythiol compound, the dicyandiamide compound, the phenol compound, the polyamine compound having an unsubstituted amino group, the acid anhydride compound, and the imidazole compound or a combination of two or more thereof. When the adhesive according to the present invention includes, as the component (B), an epoxy resin curing component other than the phosphorus-containing compound, the polythiol compound, the dicyandiamide compound, pound, the phenol compound, the polyamine compound having an unsubstituted amino group, the acid anhydride compound, and the imidazole compound, the curing component may be, for example, a metal salt such as a boron complex.

The content of the component (B) in the adhesive according to the present invention is not particularly limited, and can be appropriately adjusted according to, for example, the reaction between the component (A) and the component (B).

When the component (B) includes the phosphorus-containing compound, in the adhesive according to the present invention, the content of the phosphorus-containing compound is preferably 0.1 to 10 parts by mass, more preferably 0.3 to 5 parts by mass, still more preferably 0.5 to 4 parts by mass, relative to 100 parts by mass of the epoxy resin serving as the component (A).

When the component (B) includes the polythiol compound, in the adhesive according to the present invention, the content of the polythiol compound can be appropriately set in consideration of, for example, active hydrogen equivalent.

In the adhesive according to the present invention, the content of the polythiol compound is preferably 15 to 100 parts by mass, more preferably 20 to 90 parts by mass, more preferably 35 to 90 parts by mass, still more preferably 50 to 80 parts by mass, relative to 100 parts by mass of the epoxy resin serving as the component (A).

When the component (B) includes the dicyandiamide compound, in the adhesive according to the present invention, the content of the dicyandiamide compound can be appropriately set in consideration of, for example, active hydrogen equivalent.

For example, the content of the dicyandiamide compound may be 1 to 70 parts by mass relative to 100 parts by mass of the epoxy resin serving as the component (A), and is preferably 10 to 60 parts by mass, more preferably 20 to 65 parts by mass, still more preferably 30 to 50 parts by mass. The active hydrogen equivalent of the dicyandiamide compound relative to the epoxy equivalent of the epoxy resin serving as the component (A) (active hydrogen equivalent/epoxy equivalent) is preferably 0.3 to 1.0, more preferably 0.4 to 0.7.

When the component (B) includes the phenol compound, in the adhesive according to the present invention, the content of the phenol compound is preferably 3 to 60 parts by mass, more preferably 5 to 50 parts by mass, more preferably 10 to 40 parts by mass, still more preferably 15 to 35 parts by mass, relative to 100 parts by mass of the epoxy resin serving as the component (A).

When the component (B) includes the polyamine compound having an unsubstituted amino group, in the adhesive according to the present invention, the content of the polyamine compound having an unsubstituted amino group can be appropriately set in consideration of, for example, active hydrogen equivalent.

For example, the content of the polyamine compound may be 10 to 100 parts by mass relative to 100 parts by mass of the epoxy resin serving as the component (A), and is more preferably 20 to 90 parts by mass, more preferably 20 to 80 parts by mass, still more preferably 20 to 70 parts by mass. The active hydrogen equivalent of the polyether polyamine compound relative to the epoxy equivalent of the epoxy resin serving as the component (A) (active hydrogen equivalent/epoxy equivalent) is preferably 0.1 to 1.5, more preferably 0.3 to 1.0, still more preferably 0.5 to 1.0.

When the component (B) includes the acid anhydride compound, in the adhesive according to the present invention, the content of the acid anhydride compound is preferably 50 to 200 parts by mass, more preferably 60 to 150 parts by mass, still more preferably 80 to 120 parts by mass, relative to 100 parts by mass of the epoxy resin serving as the component (A).

When the component (B) includes the imidazole compound, in the adhesive according to the present invention, the content of the imidazole compound is preferably 1 to 20 parts by mass, more preferably 3 to 15 parts by mass, still more preferably 5 to 10 parts by mass, relative to 100 parts by mass of the epoxy resin serving as the component (A).

In this specification, when the amount of the imidazole compound relative to the epoxy resin is described, the amount of the imidazole compound means, in the case where the imidazole compound has a counterion, the amount of a portion excluding the counterion.

Component (C)

The adhesive according to the present invention includes a radical scavenger, and the radical scavenger includes at least one of components (C-1) to (C-7) described later. The adhesive according to the present invention may include one or two or more radical scavengers selected from the group consisting of the components (C-1) to (C-7).

The proportion of the total amount of the components (C-1) to (C-7) in the total amount of the radical scavenger included in the adhesive according to the present invention is preferably 70 mass % or more, preferably 80 mass % or more, more preferably 90 mass % or more. Still more preferably, the radical scavenger included in the adhesive according to the present invention is at least one of the components (C-1) to (C-7).

In the present invention, from the viewpoint of heat resistance and sterilization resistance of an adhesive cured product, the radical scavenger preferably includes at least one of the component (C-6) or the component (C-7), more preferably includes the component (C-6). The component (C-6) can catalytically trap radicals and thus exhibits a radical trapping ability over a long period of time. The component (C-7) is preferred because it is highly reactive with radicals and can rapidly trap the radicals to suppress deterioration of the adhesive cured product.

Hereinafter, the components (C-1) to (C-7) will be specifically described.

The component (C-1) is a compound represented by general formula (C-1) below.

general formula (C-1)

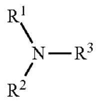

In general formula (C-1), $R^1$ and $R^2$ each represent a hydrogen atom, an aliphatic group, an acyl group, an aliphatic oxycarbonyl group, an aromatic oxycarbonyl group, an aliphatic sulfonyl group, or an aromatic sulfonyl group. $R^3$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group. $R^1$ and $R^2$, $R^2$ and $R^3$, or $R^1$ and $R^3$ may be bonded to each other to form a five- to seven-membered ring but do not form a piperidine skeleton.

In general formula (C-1), $R^1$ and $R^2$ are not simultaneously hydrogen atoms and have a total of 7 or more carbon atoms. $R^1$, $R^2$ and $R^3$ include no unsubstituted amino groups.

The aliphatic groups in general formula (C-1) (including aliphatic groups constituting part of the substituents in general formula (C-1)) mean alkyl, alkenyl, and alkynyl groups. The alkyl, alkenyl, and alkynyl groups may be linear, branched, or cyclic.

The number of carbon atoms of the alkyl groups is preferably 1 to 20, more preferably 1 to 18. However, when the alkyl groups are branched or cyclic, the lower limit of the number of carbon atoms is 3. This also applies to the alkenyl and alkynyl groups.

The number of carbon atoms of the alkenyl groups is preferably 2 to 20, more preferably 2 to 18.

The number of carbon atoms of the alkynyl groups is preferably 2 to 20, more preferably 2 to 18. The aliphatic groups may be substituted with at least one of the following substituents T. When the aliphatic groups are cyclic, they may have alkyl, alkenyl, and alkynyl groups of the following substituents T.

Substituents T

Halogen Atoms

Fluorine, Chlorine, Bromine, and Iodine Atoms

Alkyl Groups [Linear, Branched, or Cyclic Substituted or Unsubstituted Alkyl Groups]

Linear or branched alkyl groups (preferably substituted or unsubstituted alkyl groups having 1 to 30 carbon atoms, e.g., methyl, ethyl, propyl, isopropyl, t-butyl, octyl, eicosyl, 2-chloroethyl, 2-cyanoethyl, and 2-ethylhexyl)

Cycloalkyl groups (preferably substituted or unsubstituted cycloalkyl groups having 3 to 30 carbon atoms, e.g., cyclohexyl, cyclopentyl, and 4-dodecylcyclohexyl)

Bicycloalkyl groups (preferably substituted or unsubstituted bicycloalkyl groups having 5 to 30 carbon atoms, i.e., monovalent groups derived by removing one hydrogen atom from bicycloalkanes having 5 to 30 carbon atoms, e.g., bicyclo[1.2.2] heptan-2-yl and bicyclo[2.2.2] octan-3-yl)

In the present invention, cyclic alkyl groups encompass, in addition to the above cycloalkyl groups and bicycloalkyl groups (bicyclic groups), polycycloalkyl groups such as tricycloalkyl, tetracycloalkyl, and pentacycloalkyl.

Preferred examples of alkyl groups constituting substituents described below (e.g., alkyl groups of alkylthio groups) include the alkyl groups of the substituents T.

Alkenyl Groups [Linear, Branched, or Cyclic Substituted or Unsubstituted Alkenyl Groups]

Linear or branched alkenyl groups (preferably substituted or unsubstituted alkenyl groups (having 2 to 30 carbon atoms), e.g., vinyl, allyl, prenyl, geranyl, and oleyl)

Cycloalkenyl groups (preferably substituted or unsubstituted cycloalkenyl groups having 3 to 30 carbon atoms, i.e., monovalent groups derived by removing one hydrogen atom of cycloalkenes having 3 to 30 carbon atoms, e.g., 2-cyclopenten-1-yl and 2-cyclohexen-1-yl)

Bicycloalkenyl groups (substituted or unsubstituted bicycloalkenyl groups, preferably, substituted or unsubstituted bicycloalkenyl groups having 5 to 30 carbon atoms, i.e., monovalent groups derived by removing one hydrogen atom from bicycloalkenes having one double bond, e.g., bicyclo[2.2.1]hept-2-en-1-yl and bicyclo[2.2.2]oct-2-en-4-yl)

Alkynyl Groups [Linear, Branched, or Cyclic Substituted or Unsubstituted Alkynyl Groups]

Preferably, substituted or unsubstituted alkynyl groups having 2 to 30 carbon atoms, e.g., ethynyl, propargyl, and trimethylsilylethynyl Aryl Groups Preferably, substituted or unsubstituted aryl groups having 6 to 40 carbon atoms (more preferably 6 to 30 carbon atoms, particularly preferably 6 to 20 carbon atoms), e.g., phenyl, p-tolyl, naphthyl, m-chlorophenyl, o-hexadecanoylaminophenyl (more preferably, phenyl and naphthyl, particularly preferably, phenyl). The substituted aryl groups may be fused with aliphatic rings, other aromatic rings, or heterocyclic rings.

Heterocyclic Groups

Preferably, monovalent groups derived by removing one hydrogen atom from five- or six-membered, substituted or unsubstituted heterocyclic compounds (including aromatic heterocyclic compounds and non-aromatic heterocyclic compounds), more preferably, five- or six-membered, substituted or unsubstituted aromatic heterocyclic groups having 3 to 30 carbon atoms, e.g., 2-furyl, 2-thienyl, 2-pyrimidinyl, and 2-benzothiazolyl Cyano Group Hydroxy Group Nitro Group Carboxy Group Alkoxy Groups Preferably, substituted or unsubstituted alkoxy groups having 1 to 30 carbon atoms, e.g., methoxy, ethoxy, isopropoxy, t-butoxy, octyloxy, and 2-methoxyethoxy Aryloxy Groups Preferably, substituted or unsubstituted aryloxy groups having 6 to 30 carbon atoms, e.g., phenoxy, 2-methylphenoxy, 4-t-butylphenoxy, 3-nitrophenoxy, 2-tetradecanoylaminophenoxy, and p-methoxyphenoxy Silyloxy Groups Preferably, substituted or unsubstituted silyloxy groups having 3 to 20 carbon atoms, e.g., trimethylsilyloxy and t-butyldimethylsilyloxy Heterocyclic Oxy Groups Preferably, substituted or unsubstituted heterocyclic oxy groups having 2 to 30 carbon atoms, 1-phenyltetrazole-5-oxy and 2-tetrahydropyranyloxy Acyloxy Groups Preferably, a formyloxy group, substituted or unsubstituted alkylcarbonyloxy groups having 2 to 30 carbon atoms, and substituted or unsubstituted arylcarbonyloxy groups having 6 to 30 carbon atoms, e.g., formyloxy, acetyloxy, pivaloyloxy, stearoyloxy, benzoyloxy, and p-methoxyphenylcarbonyloxy Substituted Carbamoyloxy Groups Preferably, substituted carbamoyloxy groups having 1 to 30 carbon atoms (preferably 2 to 30 carbon atoms), e.g., N,N-dimethylcarbamoyloxy, N,N-diethylcarbamoyloxy, morpholinocarbonyloxy, N,N-dioctylaminocarbonyloxy, and N-octylcarbamoyloxy Alkoxycarbonyloxy Groups Preferably, substituted or unsubstituted alkoxycarbonyloxy groups having 2 to 30 carbon atoms, e.g., methoxycarbonyloxy, ethoxycarbonyloxy, t-butoxycarbonyloxy, and octyloxycarbonyloxy Aryloxycarbonyloxy Groups Preferably, substituted or unsubstituted aryloxycarbonyloxy groups having 7 to 30 carbon atoms, e.g., phenoxycarbonyloxy, p-methoxyphenoxycarbonyloxy, p-hexadecyloxyphenoxycarbonyloxy Amino Groups Preferably, substituted or unsubstituted alkylamino groups having 1 to 30 carbon atoms and substituted or unsubstituted anilino groups having 6 to 30 carbon atoms (specific examples of substituents of substituted amino groups and substituted anilino groups include aliphatic groups, aryl groups, acyl groups, aliphatic sulfonyl groups, and aromatic sulfonyl groups), e.g., methylamino, dimethylamino, anilino, N-methyl-anilino, and diphenylamino Acylamino Groups Preferably, a formylamino group, substituted or unsubstituted alkylcarbonylamino groups having 2 to 30 carbon atoms, and substituted or unsubstituted arylcarbonylamino groups having 6 to 30 carbon atoms, e.g., formylamino, acetylamino, pivaloylamino, lauroylamino, benzoylamino, and 3,4,5-trioctyloxyphenylcarbonylamino Substituted Aminocarbonylamino Groups (Monosubstituted or Disubstituted Amino-Carbonyl-Amino Groups)

Preferably, substituted aminocarbonylamino groups having 1 to 30 carbon atoms, e.g., N,N-dimethylaminocarbonylamino, N,N-diethylaminocarbonylamino, and morpholinocarbonylamino Alkoxycarbonylamino Groups Preferably, substituted or unsubstituted alkoxycarbonylamino groups having 2 to 30 carbon atoms, e.g., methoxycarbonylamino, ethoxycarbonylamino, t-butoxycarbonylamino, octadecyloxycarbonylamino, and N-methyl-methoxycarbonylamino Aryloxycarbonylamino Groups Preferably, substituted or unsubstituted aryloxycarbonylamino groups having 7 to 30 carbon atoms, e.g., phenoxycarbonylamino, p-chlorophenoxycarbonylamino, and m-octyloxyphenoxycarbonylamino Substituted Sulfamoylamino Groups (Substituted Sulfamoyl-Amino Groups)

Preferably, substituted sulfamoylamino groups having 0 to 30 carbon atoms (preferably 1 to 30 carbon atoms), e.g., N,N-dimethylaminosulfonylamino and N-octylaminosulfonylamino Alkylsulfonylamino and Arylsulfonylamino Groups Preferably, substituted or unsubstituted alkylsulfonylamino groups having 1 to 30 carbon atoms and substituted or unsubstituted arylsulfonylamino groups having 6 to 30 carbon atoms, e.g., methylsulfonylamino, butylsulfonylamino, phenylsulfonylamino, 2,3,5-trichlorophenylsulfonylamino, and p-methylphenylsulfonylamino Sulfanyl Group Alkylthio Groups Preferably, substituted or unsubstituted alkylthio groups having 1 to 30 carbon atoms, e.g., methylthio, ethylthio, hexadecylthio, and octylthio Arylthio Groups Preferably, substituted or unsubstituted arylthio groups having 6 to 30 carbon atoms, e.g., phenylthio, p-chlorophenylthio, m-methoxyphenylthio, and p-methoxyphenylthio Heterocyclic Thio Groups Preferably, substituted or unsubstituted heterocyclic thio groups having 2 to 30 carbon atoms, e.g., 2-benzothiazolylthio and 1-phenyltetrazol-5-ylthio Sulfamoyl Groups Preferably, substituted sulfamoyl groups having 0 to 30 carbon atoms (preferably 1 to 30 carbon atoms), e.g., N-ethylsulfamoyl, N-(3-dodecyloxypropyl) sulfamoyl, N,N-dimethylsulfamoyl, N-acetylsulfamoyl, N-benzoylsulfamoyl, and N—(N'-phenylcarbamoyl) sulfamoyl Sulfo Group Alkylsulfinyl and Arylsulfinyl Groups Preferably, substituted or unsubstituted alkylsulfinyl groups having 1 to 30 carbon atoms and substituted or unsubstituted arylsulfinyl groups having 6 to 30 carbon atoms, e.g., methylsulfinyl, ethylsulfinyl, phenylsulfinyl, and p-methylphenylsulfinyl Alkylsulfonyl and Arylsulfonyl Groups Preferably, substituted or unsubstituted alkylsulfonyl groups having 1 to 30 carbon atoms and substituted or unsubstituted arylsulfonyl groups having 6 to 30 carbon atoms, e.g., methylsulfonyl, ethylsulfonyl, butylsulfonyl, phenylsulfonyl, and p-methylphenylsulfonyl Acyl Groups Preferably, a formyl group, substituted or unsubstituted alkylcarbonyl groups having 2 to 30 carbon atoms, substituted or unsubstituted arylcarbonyl groups having 7 to 30 carbon atoms, and substituted or unsubstituted heterocyclic carbonyl groups having 4 to 30 carbon atoms (in each of the heterocyclic carbonyl groups, any of the carbon atoms of the heterocyclic ring is bonded to the carbon atom of the carbonyl group), e.g., acetyl, pivaloyl, 2-chloroacetyl, stearoyl, benzoyl, p-octyloxyphenylcarbonyl, 2-pyridylcarbonyl, 2-furylcarbonyl, and (meth)acryloyl Aryloxycarbonyl Groups Preferably, substituted or unsubstituted aryloxycarbonyl groups having 7 to 30 carbon atoms, e.g., phenoxycarbonyl, o-chlorophenoxycarbonyl, m-nitrophenoxycarbonyl, and p-t-butylphenoxycarbonyl Alkoxycarbonyl Groups Preferably, substituted or unsubstituted alkoxycarbonyl groups having 2 to 30 carbon atoms, e.g., methoxycarbonyl, ethoxycarbonyl, t-butoxycarbonyl, hexadecyloxycarbonyl, and octadecyloxycarbonyl Carbamoyl Groups Preferably, substituted carbamoyl groups having 1 to 30 carbon atoms (preferably 2 to 30 carbon atoms), e.g., N-methylcarbamoyl, N,N-dimethylcarbamoyl, N,N-dioctylcarbamoyl, and N-(methylsulfonyl) carbamoyl Arylazo and Heterocyclic Azo Groups Preferably, substituted or unsubstituted arylazo groups having 6 to 30 carbon atoms and substituted or unsubstituted heterocyclic azo groups having 3 to 30 carbon atoms, e.g., phenylazo, p-chlorophenylazo, and 5-ethylthio-1,3,4-thiadiazol-2-ylazo Imide Groups Preferably, N-succinimide and N-phthalimide Phosphino Groups Preferably, substituted or unsubstituted phosphino groups having 2 to 30 carbon atoms, e.g., dimethylphosphino, diphenylphosphino, and methylphenoxyphosphino Phosphinyl Groups Preferably, a phosphinyl group and substituted or unsubstituted phosphinyl groups having 2 to 30 carbon atoms, e.g., phosphinyl, dioctyloxyphosphinyl, and diethoxyphosphinyl Phosphinyloxy Groups Preferably, substituted or unsubstituted phosphinyloxy groups having 2 to 30 carbon atoms, e.g., diphenoxyphosphinyloxy and dioctyloxyphosphinyloxy Phosphinylamino Groups Preferably, substituted or unsubstituted phosphinylamino groups having 2 to 30 carbon atoms, e.g., dimethoxyphosphinylamino and dimethylaminophosphinylamino Silyl Groups Preferably, substituted or unsubstituted silyl groups having 3 to 30 carbon atoms, e.g., trimethylsilyl, t-butyldimethylsilyl, and phenyldimethylsilyl Of the above substituents T, for those having a hydrogen atom, the hydrogen atom may further be substituted with any of the above groups. Examples of such substituents include alkylcarbonylaminosulfonyl groups, arylcarbonylaminosulfonyl groups, alkylsulfonylaminocarbonyl groups, and arylsulfonylaminocarbonyl groups. Examples thereof include methylsulfonylaminocarbonyl, p-methylphenylsulfonylaminocarbonyl, acetylaminosulfonyl, and benzoylaminosulfonyl groups.

Specific examples of the acyl group in general formula (C-1) include the acyl groups of the substituents T.

Specific examples of the aliphatic oxycarbonyl group in general formula (C-1) include the alkoxycarbonyl groups of the substituents T.

Specific examples of the aromatic oxycarbonyl group in general formula (C-1) include the aryloxycarbonyl groups of the substituents T.

Specific examples of the aliphatic sulfonyl group in general formula (C-1) include the alkylsulfonyl groups of the substituents T.

Specific examples of the aromatic sulfonyl group in general formula (C-1) include the arylsulfonyl groups of the substituents T.

Specific examples of the aliphatic oxy group in general formula (C-1) include the alkoxy groups of the substituents T.

Specific examples of the aromatic oxy group in general formula (C-1) include the aryloxy groups of the substituents T.

Specific examples of the aliphatic thio group in general formula (C-1) include the alkylthio groups of the substituents T.

Specific examples of the aromatic thio group in general formula (C-1) include the arylthio groups of the substituents T.

Specific examples of the acyloxy group in general formula (C-1) include the acyloxy groups of the substituents T.

Specific examples of the aliphatic oxycarbonyloxy group in general formula (C-1) include the alkoxycarbonyloxy groups of the substituents T.

Specific examples of the aromatic oxycarbonyloxy group in general formula (C-1) include the aryloxycarbonyloxy groups of the substituents T.

Specific examples of the substituted amino group in general formula (C-1) include the substituted amino groups of the substituents T.

The heterocyclic group in general formula (C-1) preferably includes a five-membered or six-membered, saturated or unsaturated heterocyclic ring. The heterocyclic ring may be fused with an aliphatic ring, an aromatic ring, or another heterocyclic ring. Examples of heteroatoms of the heterocyclic ring include B, N, O, S, Se, and Te. Preferred heteroatoms are N, O, and S. The heterocyclic ring preferably has a free valance (monovalence) on its carbon atom (the heterocyclic group is bonded through the carbon atom). The number of carbon atoms of the heterocyclic group is preferably 1 to 40, more preferably 1 to 30, still more preferably 1 to 20. Examples of saturated heterocyclic rings include a pyrazolidine ring, a pyrrolidine ring, a morpholine ring, a 2-bora-1,3-dioxolane ring, and a 1,3-thiazolidine ring (a piperidine ring is excluded). Examples of unsaturated heterocyclic rings include an imidazole ring, a thiazole ring, a benzothiazole ring, a benzoxazole ring, a benzotriazole ring, benzoselenazole ring, a pyridine ring, a pyrimidine ring, and a quinoline ring. The heterocyclic group may have a substituent. Examples of the substituent include the above substituents T.

In general formula (C-1), the total number of carbon atoms of $R^1$ and $R^2$ is 7 or more, preferably 7 to 70, more preferably 7 to 40.

The compound represented by general formula (C-1) for use in the present invention includes compounds represented by, for example, general formula (I) in JP1994-97332B (JP-H6-97332B), general formula (I) in JP1994-97334B (JP-H6-97334B), general formula (I) JP1990-148037A (JP-H2-148037A), general formula (I) in JP1990-150841A (JP-H2-150841A), general formula (I) in JP1990-181145A (JP-H2-181145A), general formula (I) JP1991-266836A (JP-H3-266836A), general formula (IV) in JP1992-350854A (JP-H4-350854A), and general formula (I) JP1993-61166A (JP-H5-61166A).

The compound represented by general formula (C-1) is preferably a compound represented by general formula (C-1a) or (C-1b) below.

general formula (C-1a)

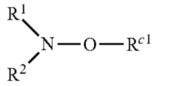

general formula (C-1b)

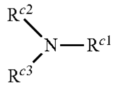

In general formula (C-1a), $R^1$ and $R^2$ respectively have the same definitions as $R^1$ and $R^2$ in formula (C-1). $R^{c1}$ has the same definition as $R^1$ In general formula (C-1b), $R^{c2}$ to $R^{c4}$ each represent an aliphatic group or an acyl group.

Specific examples of the compound represented by general formula (C-1) are given below, but these examples are not intended to limit the present invention.

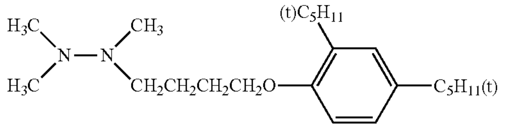

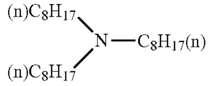

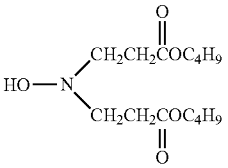

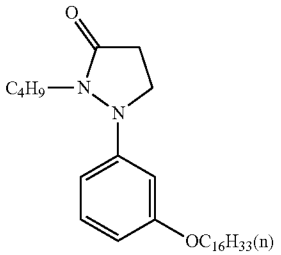

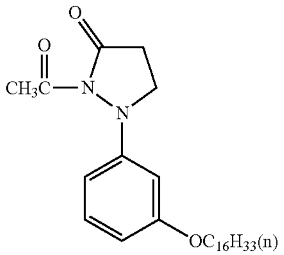

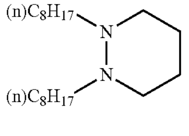

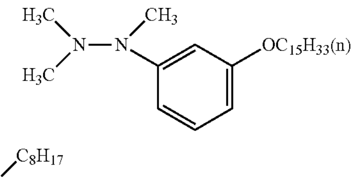

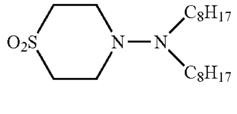

-continued

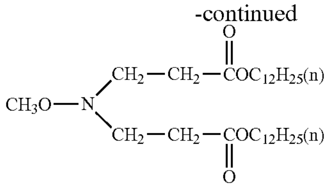

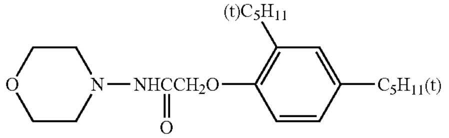

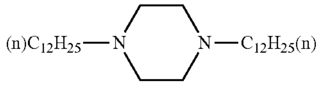

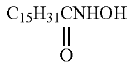

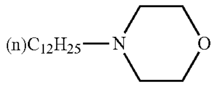

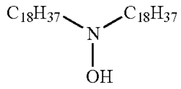

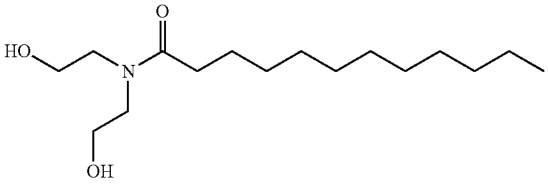

The component (C-2) is a compound represented by general formula (C-2) below.

general formula (C-2)

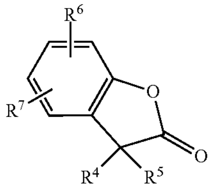

In general formula (C-2), $R^4$ to $R^7$ each represent a hydrogen atom, an alkyl group having 1 to 20 carbon atoms, an aralkyl group having 7 to 20 carbon atoms, or an aryl group having 6 to 15 carbon atoms. The substituents represented by $R^4$ to $R^7$ may each have at least one of the substituents T.

In general formula (C-2), the alkyl group having 1 to 20 carbon atoms may be a linear or branched alkyl group. Examples include methyl, ethyl, propyl, isopropyl, butyl, isobutyl, pentyl, 2-ethylbutyl, hexyl, heptyl, octyl, 2-ethylhexyl, nonyl, decyl, dodecyl, tetradecyl, octadecyl, eicosyl, benzyl, 2,6-di-t-butyl-4-methylbenzyl, phenethyl, phenylpropyl, naphthylmethyl, and 2-phenylisopropyl. When the alkyl group has a substituent, the above number of carbon atoms includes the number of carbon atoms of the substituent.

In general formula (C-2), the aryl group having 6 to 15 carbon atoms may be, for example, phenyl, tolyl, or naphthyl. When the aryl group has a substituent, the above number of carbon atoms includes the number of carbon atoms of the substituent.

In general formula (C-2), $R^4$ and $R^5$ is preferably a combination of a hydrogen atom and an aryl group having 7 to 20 carbon atoms. In particular, preferred is a combination of a hydrogen atom and an aryl group having 8 to 20 carbon atoms, more preferred is a combination of a hydrogen atom and an aryl group having 8 to 18 carbon atoms, and particularly preferred is a combination of a hydrogen atom and 3,4-dimethylphenyl.

In general formula (C-2), $R^6$ and $R^7$ are each preferably, of the above, an alkyl group having 1 to 20 carbon atoms, more preferably an alkyl group having 2 to 20 carbon atoms, still more preferably an alkyl group having 3 to 20 carbon atoms, particularly preferably t-butyl.

Specific examples of the compound represented by general formula (C-2) include the following compounds. However, these examples are not intended to limit the present invention.

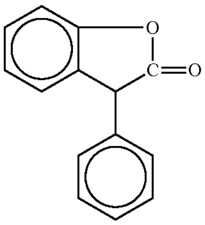

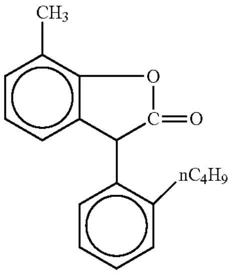

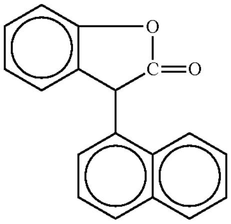

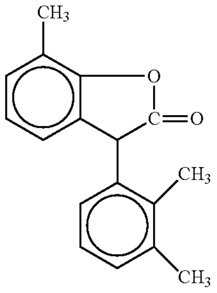

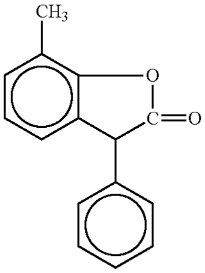

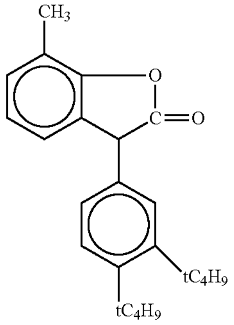

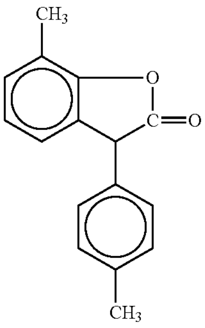

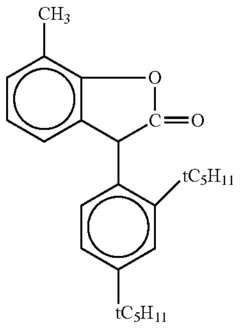

-continued
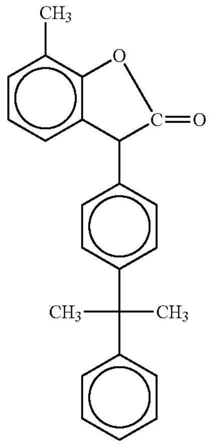
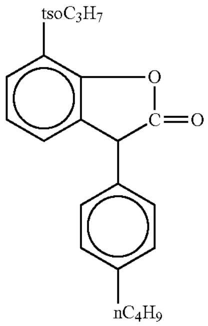
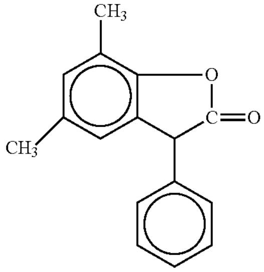
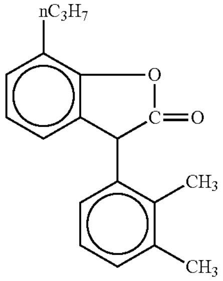
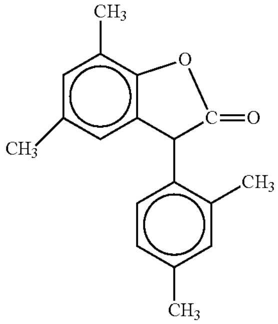
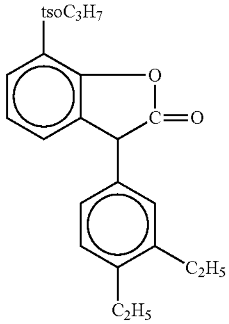
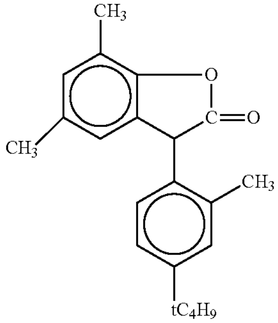
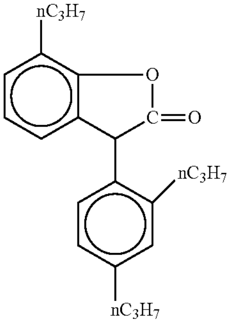
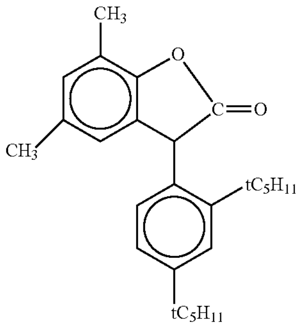
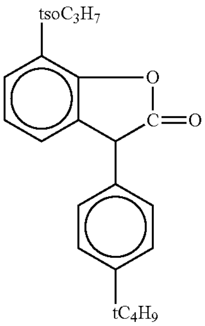
-continued
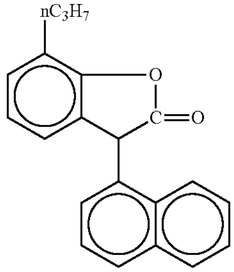
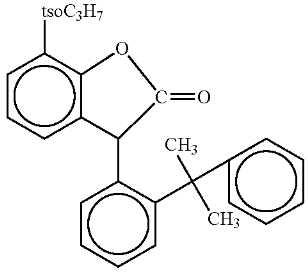
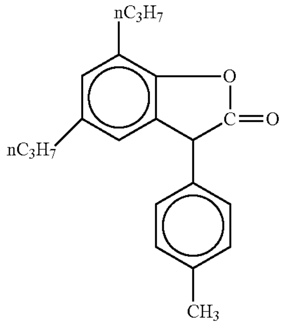
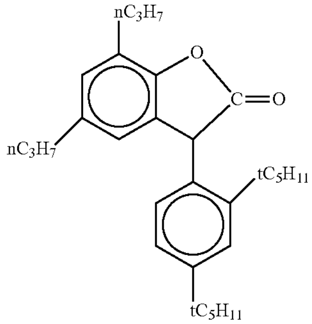
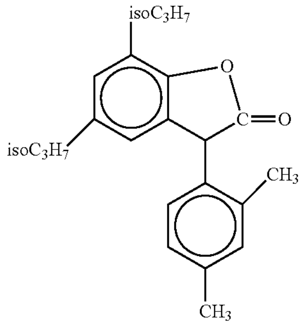
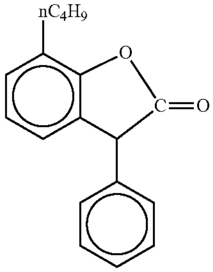

-continued
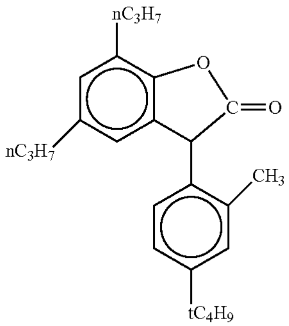
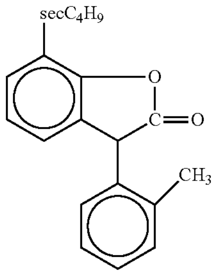
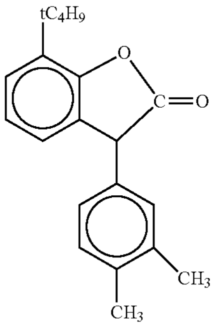
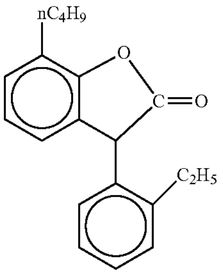
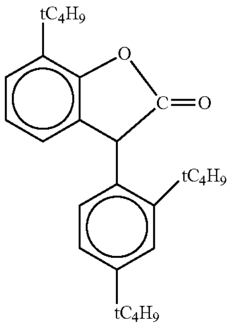
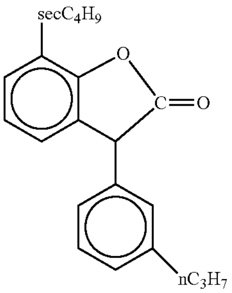
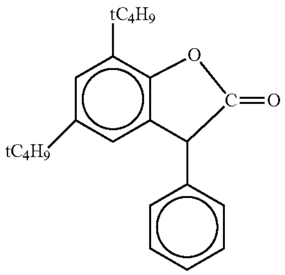
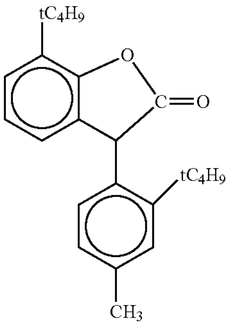
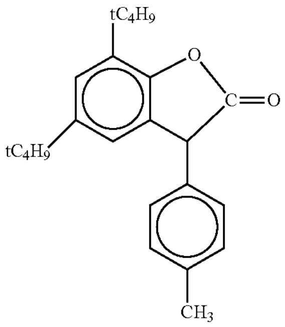
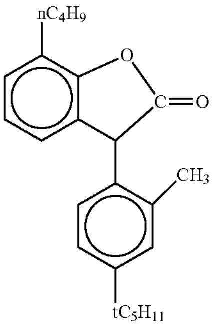
-continued
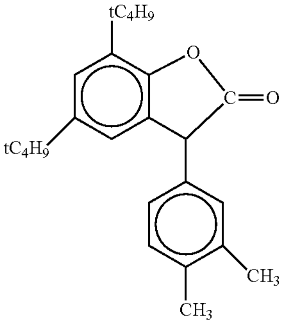
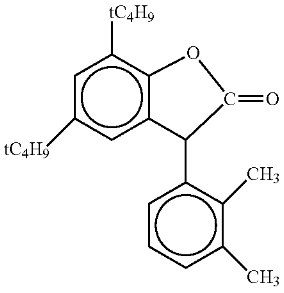
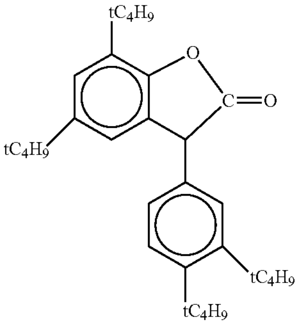
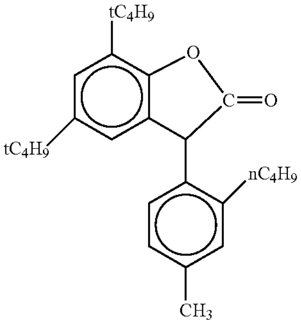
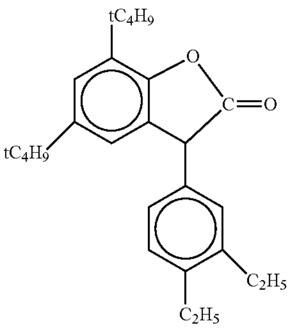

-continued

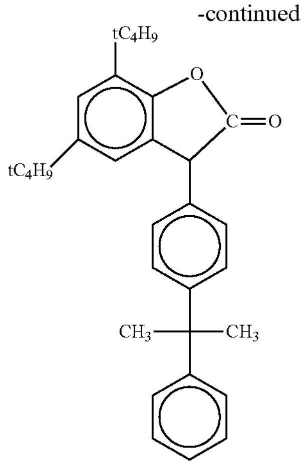

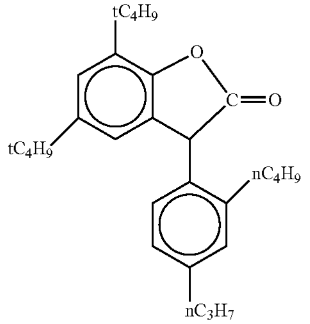

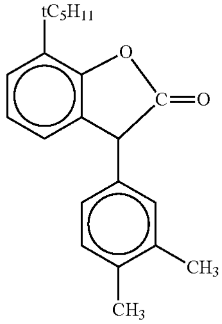

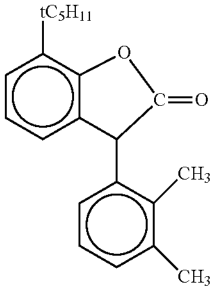

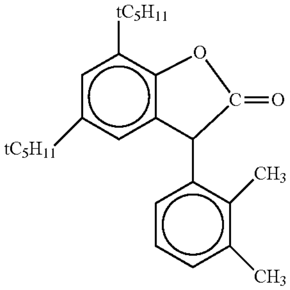

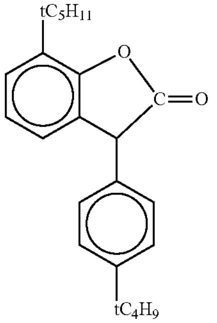

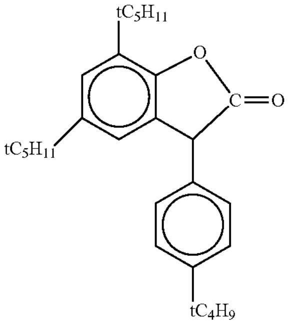

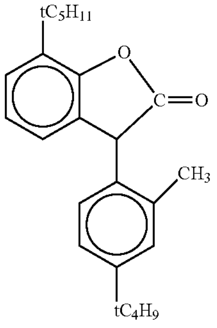

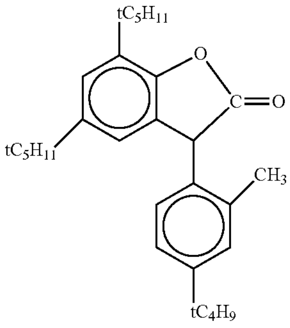

-continued

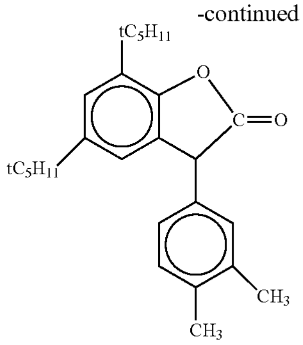

The component (C-3) is a compound represented by formula (C-3) below.

formula (C-3)

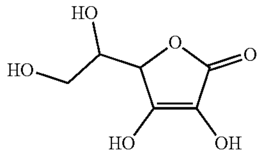

The component (C-4) is a compound represented by general formula (C-4) below.

general formula (C-4)

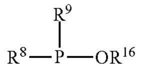

In general formula (C-4), $R^8$ and $R^9$ each represent an alkyl group, an aryl group, an alkoxy group, an aryloxy group, or a halogen atom, and $R^{10}$ represents an alkyl group or an aryl group. At least two of $R^8$, $R^9$, and $R^{10}$ may be linked to each other via a divalent or higher valent group or a single bond.

In the present invention, compounds having a structure represented by general formula (C-4) include, in addition to the compound represented by general formula (C-4), the following compounds (a) and (b).

(a) Compounds having a structure in which a monovalent group derived by removing one hydrogen atom from $R^8$, $R^9$, or $R^{10}$ is linked to at least one of $R^8$, $R^9$, or $R^{10}$ of one or more (preferably an integer of 1 to 3) other compounds represented by general formula (C-4) via a divalent or higher valent group or a single bond, and (b) compounds having a structure in which a divalent or higher valent group derived by removing a total of two or more hydrogen atoms from at least one group selected from the group consisting of $R^8$, $R^9$, and $R^{10}$ (e.g., a divalent group if two hydrogen atoms are removed, or a trivalent group if three hydrogen atoms are removed) is linked to at least one of $R^8$, $R^9$, or $R^{10}$ of one or more (preferably an integer of 1 to 3) other compounds represented by general formula (C-4) via a divalent or higher valent group or a single bond.

That is, in the present invention, compounds having a structure represented by general formula (C-4) are meant to include the compound represented by general formula (C-4) and compounds having a structure in which a plurality of structures represented by general formula (C-4) are present in one molecule.

The alkyl groups represented by $R^8$, $R^9$, and $R^{10}$ in general formula (C-4) are linear, branched, or cyclic substituted or unsubstituted alkyl groups having preferably 1 to 50 carbon atoms, more preferably 1 to 30 carbon atoms, particularly preferably 1 to 20 carbon atoms. Preferred examples include methyl, ethyl, n-propyl, isopropyl, cyclopropyl, butyl, isobutyl, t-butyl, s-butyl, pentyl, isopentyl, neopentyl, t-pentyl, hexyl, cyclohexyl, heptyl, cyclopentyl, octyl, 2-ethylhexyl, nonyl, decyl, dodecyl, tetradecyl, hexadecyl, octadecyl, eicosyl, docosyl, and triacontyl. More preferred are methyl, ethyl, n-propyl, isopropyl, butyl, isobutyl, t-butyl, s-butyl, pentyl, isopentyl, neopentyl, hexyl, cyclohexyl, octyl, 2-ethylhexyl, dodecyl, hexadecyl, and octadecyl, and still more preferred are methyl, ethyl, n-propyl, isopropyl, butyl, t-butyl, pentyl, isopentyl, hexyl, cyclohexyl, octyl, 2-ethylhexyl, dodecyl, hexadecyl, and octadecyl.

The alkyl groups represented by $R^8$, $R^9$, and $R^{10}$ may further have a substituent. Examples of the substituent include halogen atoms, cycloalkyl groups, alkenyl groups, alkynyl groups, aryl groups, a cyano group, a hydroxy group, a nitro group, a carboxy group, alkoxy groups, aryloxy groups, acyloxy groups, a carbamoyloxy group, alkoxycarbonyloxy groups, aryloxycarbonyloxy groups, amino groups (including an anilino group), acylamino groups, an aminocarbonylamino group, alkoxycarbonylamino groups, aryloxycarbonylamino groups, acyl groups, aryloxycarbonyl groups, alkoxycarbonyl groups, and a carbamoyl group.

More particularly, examples of the substituent include halogen atoms (e.g., chlorine, bromine, and iodine atoms), alkyl groups [(which represent linear, branched, or cyclic substituted or unsubstituted alkyl groups, including, for example, alkyl groups (preferably, alkyl groups having 1 to 30 carbon atoms, e.g., methyl, ethyl, n-propyl, isopropyl, t-butyl, n-octyl, eicosyl, 2-chloroethyl, 2-cyanoethyl, and 2-ethylhexyl), cycloalkyl groups (preferably, substituted or unsubstituted cycloalkyl groups having 3 to 30 carbon atoms, e.g., cyclohexyl, cyclopentyl, and 4-n-dodecylcyclohexyl), bicycloalkyl groups (preferably, substituted or unsubstituted bicycloalkyl groups having 5 to 30 carbon atoms, i.e., monovalent groups derived by removing one hydrogen atom from bicycloalkanes having 5 to 30 carbon atoms, e.g., bicyclo[1.2.2]heptan-2-yl and bicyclo[2.2.2]octan-3-yl), and tricyclo structures having more cyclic structures; this definition of alkyl groups also applies to alkyl groups of substituents described below (e.g., alkyl groups of alkylthio groups)), alkenyl groups (preferably, substituted or unsubstituted alkenyl groups having 2 to 30 carbon atoms, e.g., vinyl, allyl, prenyl, geranyl, and oleyl), cycloalkenyl groups (preferably, substituted or unsubstituted cycloalkenyl groups having 3 to 30 carbon atoms, i.e., monovalent groups derived by removing one hydrogen atom from cycloalkenes having 3 to 30 carbon atoms, e.g., 2-cyclopenten-1-yl and 2-cyclohexen-1-yl), bicycloalkenyl groups (substituted or unsubstituted bicycloalkenyl groups, preferably, substituted or unsubstituted bicycloalkenyl groups having 5 to 30 carbon atoms, i.e., monovalent groups derived by removing one hydrogen atom from bicycloalkenes having one double bond, e.g., bicyclo[2.2.1]hept-2-en-1-yl and bicyclo[2.2.2]oct-2-en-4-yl)], alkynyl groups (preferably, substituted or unsubstituted alkynyl groups having 2 to 30 carbon atoms, e.g., ethynyl, propargyl, and trimethylsilylethynyl), aryl groups (preferably, substituted or unsubstituted aryl groups having 6 to 30 carbon atoms, e.g., phenyl, p-tolyl, naphthyl, m-chlorophenyl, and o-hexadecanoylaminophenyl), heterocyclic groups (preferably, monovalent groups derived by removing one hydrogen atom from five- or six-membered, substituted or unsubstituted, aromatic or non-aromatic heterocyclic compounds, more preferably five-membered or six-membered, aromatic heterocyclic groups having 3 to 30 carbon atoms, e.g., 2-furanyl, 2-thienyl, 2-pyrimidinyl, and 2-benzothiazolinyl), a cyano group, a hydroxy group, a nitro group, a carboxy group, alkoxy groups (preferably, substituted or unsubstituted alkoxy groups having 1 to 32 carbon atoms, e.g., methoxy, ethoxy, isopropoxy, t-butoxy, n-octyloxy, and 2-methoxyethoxy), aryloxy groups (preferably, substituted or unsubstituted aryloxy groups having 6 to 30 carbon atoms, e.g., phenoxy, 2-methylphenoxy, 4-t-butylphenoxy, 3-nitrophenoxy, and 2-tetradecanoylaminophenoxy), silyloxy groups (preferably, silyloxy groups having 3 to 20 carbon atoms, e.g., trimethylsilyloxy and t-butyldimethylsilyloxy), heterocyclic oxy groups (preferably, substituted or unsubstituted heterocyclic oxy groups having 2 to 30 carbon atoms, 1-phenyltetrazol-5-oxy and 2-tetrahydropyranyloxy), acyloxy groups (preferably, a formyloxy group, substituted or unsubstituted alkylcarbonyloxy groups having 2 to 30 carbon atoms, and substituted or unsubstituted arylcarbonyloxy groups having 6 to 30 carbon atoms, e.g., formyloxy, acetyloxy, pivaloyloxy, stearoyloxy, benzoyloxy, and p-methoxyphenylcarbonyloxy), carbamoyloxy groups (preferably, substituted or unsubstituted carbamoyloxy groups having 1 to 30 carbon atoms, e.g., N,N-dimethylcarbamoyloxy, N,N-diethylcarbamoyloxy, morpholinocarbonyloxy, N,N-di-n-octylaminocarbonyloxy, and N-n-octylcarbamoyloxy), alkoxycarbonyloxy groups (preferably, substituted or unsubstituted alkoxycarbonyloxy groups having 2 to 30 carbon atoms, e.g., methoxycarbonyloxy, ethoxycarbonyloxy, t-butoxycarbonyloxy, and n-octyloxycarbonyloxy), aryloxycarbonyloxy groups (preferably, substituted or unsubstituted aryloxycarbonyloxy groups having 7 to 30 carbon atoms, e.g., phenoxycarbonyloxy, p-methoxyphenoxycarbonyloxy, and p-n-hexadecyloxyphenoxycarbonyloxy), amino groups (preferably, amino groups, substituted or unsubstituted alkylamino groups having 1 to 30 carbon atoms, and substituted or unsubstituted anilino groups having 6 to 30 carbon atoms, e.g., amino, methylamino, dimethylamino, anilino, N-methyl-anilino, and diphenylamino), acylamino groups (preferably, a formylamino group, substituted or unsubstituted alkylcarbonylamino groups having 1 to 30 carbon atoms, and substituted or unsubstituted arylcarbonylamino groups having 6 to 30 carbon atoms, e.g., formylamino, acetylamino, pivaloylamino, lauroylamino, benzoylamino, and 3,4,5-tri-n-octyloxyphenylcarbonylamino), aminocarbonylamino groups (preferably, substituted or unsubstituted aminocarbonylamino groups having 1 to 30 carbon atoms, e.g., carbamoylamino, N,N-dimethylaminocarbonylamino, N,N-diethylaminocarbonylamino, and morpholinocarbonylamino), alkoxycarbonylamino groups (preferably, substituted or unsubstituted alkoxycarbonylamino groups having 2 to 30 carbon atoms, e.g., methoxycarbonylamino, ethoxycarbonylamino, t-butoxycarbonylamino, n-octadecyloxycarbonylamino, and N-methyl-methoxycarbonylamino), aryloxycarbonylamino groups (preferably, substituted or unsubstituted aryloxycarbonylamino groups having 7 to 30 carbon atoms, e.g., phenoxycarbonylamino, p-chlorophenoxycarbonylamino, and m-n-octyloxyphenoxycarbonylamino), sulfamoylamino groups (preferably, substituted or unsubstituted sulfamoylamino groups having 0 to 30 carbon atoms, e.g., sulfamoylamino, N,N-dimethylaminosulfonylamino, and N-n-octylaminosulfonylamino), alkylsulfonylamino and arylsulfonylamino groups (preferably, substituted or unsubstituted alkylsulfonylamino groups having 1 to 30 carbon atoms and substituted or unsubstituted arylsulfonylamino groups having 6 to 30 carbon atoms, e.g., methylsulfonylamino, butylsulfonylamino, phenylsulfonylamino, 2,3,5-trichlorophenylsulfonylamino, and p-methylphenylsulfonylamino), a sulfanyl group, alkylthio groups (preferably, substituted or unsubstituted alkylthio groups having 1 to 30 carbon atoms, e.g., methylthio, ethylthio, and n-hexadecylthio), arylthio groups (preferably, substituted or unsubstituted arylthio groups having 6 to 30 carbon atoms, e.g., phenylthio, p-chlorophenylthio, and m-methoxyphenylthio), heterocyclic thio groups (preferably, substituted or unsubstituted heterocyclic thio groups having 2 to 30 carbon atoms, e.g., 2-benzothiazolylthio and 1-phenyltetrazol-5-ylthio), sulfamoyl groups (preferably, substituted or unsubstituted sulfamoyl groups having 0 to 30 carbon atoms, e.g., N-ethylsulfamoyl, N-(3-dodecyloxypropyl) sulfamoyl, N,N-dimethylsulfamoyl, N-acetylsulfamoyl, N-benzoylsulfamoyl, and N—(N'-phenylcarbamoyl) sulfamoyl), a sulfo group, alkylsulfinyl and arylsulfinyl groups (preferably, substituted or unsubstituted alkylsulfinyl groups having 1 to 30 carbon atoms and substituted or unsubstituted arylsulfinyl groups having 6 to 30 carbon atoms, e.g., methylsulfinyl, ethylsulfinyl, phenylsulfinyl, and p-methylphenylsulfinyl), alkylsulfonyl and arylsulfonyl groups (preferably, substituted or unsubstituted alkylsulfonyl groups having 1 to 30 carbon atoms and substituted or unsubstituted arylsulfonyl groups having 6 to 30 carbon atoms, e.g., methylsulfonyl, ethylsulfonyl, phenylsulfonyl, and p-methylphenylsulfonyl), acyl groups (preferably, a formyl group, substituted or unsubstituted alkylcarbonyl groups having 2 to 30 carbon atoms, substituted or unsubstituted arylcarbonyl groups having 7 to 30 carbon atoms, and substituted or unsubstituted heterocyclic carbonyl groups having 4 to 30 carbon atoms in which any of the carbon atoms is bonded to the carbonyl group, e.g., acetyl, pivaloyl, 2-chloroacetyl, stearoyl, benzoyl, p-n-octyloxyphenylcarbonyl, 2-pyridylcarbonyl, and 2-furylcarbonyl), aryloxycarbonyl groups (preferably, substituted or unsubstituted aryloxycarbonyl groups having 7 to 30 carbon atoms, e.g., phenoxycarbonyl, o-chlorophenoxycarbonyl, m-nitrophenoxycarbonyl, and p-t-butylphenoxycarbonyl), alkoxycarbonyl groups (preferably, substituted or unsubstituted alkoxycarbonyl groups having 2 to 30 carbon atoms, e.g., methoxycarbonyl, ethoxycarbonyl, t-butoxycarbonyl, and n-octadecyloxycarbonyl), carbamoyl groups (preferably, substituted or unsubstituted carbamoyl groups having 1 to 30 carbon atoms, e.g., carbamoyl, N-methylcarbamoyl, N,N-dimethylcarbamoyl, N,N-di-n-octylcarbamoyl, and N-(methylsulfonyl) carbamoyl), arylazo and heterocyclic azo groups (preferably, substituted or unsubstituted arylazo groups having 6 to 30 carbon atoms and substituted or unsubstituted heterocyclic azo groups having 3 to 30 carbon atoms, e.g., phenylazo, p-chlorophenylazo, 5-ethylthio-1,3,4-thiadiazol-2-ylazo), imide groups (preferably, N-succinimide and N-phthalimide), phosphino groups (preferably, substituted or unsubstituted phosphino groups having 2 to 30 carbon atoms, e.g., dimethylphosphino, diphenylphosphino, and methylphenoxyphosphino), phosphinyl groups (preferably, substituted or unsubstituted phosphinyl groups having 2 to 30 carbon atoms, e.g., phosphinyl, dioctyloxyphosphinyl, and diethoxyphosphinyl), phosphinyloxy groups (preferably, substituted or unsubstituted phosphinyloxy groups having 2 to 30 carbon atoms, e.g., diphenoxyphosphinyloxy and dioctyloxyphosphinyloxy), phosphinylamino groups (preferably, substituted or unsubstituted phosphinylamino groups having 2 to 30 carbon atoms, e.g., dimethoxyphosphinylamino and dimethylaminophosphinylamino), and silyl groups (preferably, substituted or unsubstituted silyl groups having 3 to 30 carbon atoms, e.g., trimethylsilyl, t-butyldimethylsilyl, and phenyldimethylsilyl).

Of the above substituents, for those having a hydrogen atom, the hydrogen atom may further be substituted with any of the above substituents. Examples of such substituents include alkylcarbonylaminosulfonyl groups, arylcarbonylaminosulfonyl groups, alkylsulfonylaminocarbonyl groups, arylsulfonylaminocarbonyl groups, a methylsulfonylaminocarbonyl group, a p-methylphenylsulfonylaminocarbonyl group, an acetylaminosulfonyl group, and a benzoylaminosulfonyl group.

The aryl groups represented by $R^8$, $R^9$, and $R^{10}$ represent substituted or unsubstituted aryl groups having preferably 6 to 50 carbon atoms, more preferably 6 to 30 carbon atoms, particularly preferably 6 to 20 carbon atoms. Preferred examples include phenyl, 2-methylphenyl, 3-methylphenyl, 4-methylphenyl, 2-ethylphenyl, 4-ethylphenyl, 2,4-dimethylphenyl, 2,6-dimethylphenyl, 2,4,6-trimethylphenyl, 1-naphthyl, 2-naphthyl, 2-chlorophenyl, 3-chlorophenyl, 4-chlorophenyl, 2-methoxyphenyl, 3-methoxyphenyl, 4-methoxyphenyl, 2-benzylphenyl, 4-benzylphenyl, 2-methylcarbonylphenyl, and 4-methylcarbonylphenyl.

The aryl groups represented by $R^8$, $R^9$, and $R^{10}$ are more preferably phenyl, 2-methylphenyl, 4-methylphenyl, 2-ethylphenyl, 4-ethylphenyl, 2,4-dimethylphenyl, 2,6-dimethylphenyl, 2,4,6-trimethylphenyl, 1-naphthyl, 2-naphthyl, 2-chlorophenyl, 4-chlorophenyl, 2-methoxyphenyl, 3-methoxyphenyl, 4-methoxyphenyl, 2-benzylphenyl, or 4-benzylphenyl, particularly preferably phenyl.

The above aryl groups represented by $R^8$, $R^9$, and $R^{10}$ may further have a substituent. Examples of the substituent include the above-described substituents that the alkyl groups represented by $R^8$, $R^9$, and $R^{10}$ may have.

The alkoxy groups represented by $R^8$ and $R^9$ are linear, branched, or cyclic substituted or unsubstituted alkoxy groups. The alkoxy groups have preferably 1 to 50 carbon atoms, more preferably 1 to 30 carbon atoms, particularly preferably 1 to 20 carbon atoms. Preferred examples include methoxy, ethoxy, n-propoxy, isopropoxy, cyclopropoxy, butoxy, isobutoxy, t-butoxy, s-butoxy, pentyloxy, isopentyloxy, neopentyloxy, t-pentyloxy, hexyloxy, cyclohexyloxy, heptyloxy, cyclopentyloxy, octyloxy, 2-ethylhexyloxy, nonyloxy, decyloxy, dodecyloxy, tetradecyloxy, hexadecyloxy, octadecyloxy, eicosyloxy, docosyloxy, and triacontyloxy. More preferred are methoxy, ethoxy, n-propoxy, isopropoxy, butoxy, isobutoxy, t-butoxy, s-butoxy, pentyloxy, isopentyloxy, neopentyloxy, hexyloxy, cyclohexyloxy, octyloxy, 2-ethylhexyloxy, dodecyloxy, hexadecyloxy, and octadecyloxy, and particularly preferred are methoxy, ethoxy, n-propoxy, isopropoxy, t-butoxy, pentyloxy, isopentyloxy, hexyloxy, cyclohexyloxy, octyloxy, 2-ethylhexyloxy, dodecyloxy, hexadecyloxy, and octadecyloxy.

The above alkoxy groups represented by $R^8$ and $R^9$ may further have a substituent. Examples of the substituent include the above-described substituents that the alkyl groups represented by $R^8$, $R^9$, and $R^{10}$ may have.

The aryloxy groups represented by $R^8$ and $R^9$ are substituted or unsubstituted aryloxy groups having preferably 6 to 50 carbon atoms, more preferably 6 to 30 carbon atoms, particularly preferably 6 to 20 carbon atoms. Preferred examples include phenoxy, 2-methylphenoxy, 3-methylphenoxy, 4-methylphenoxy, 2-ethylphenoxy, 4-ethylphenoxy, 2,4-dimethylphenoxy, 2,4-di-t-butylphenoxy, 2,6-di-t- butylphenoxy, 2,6-dimethylphenoxy, 2,6-di-t-butyl-4-methylphenoxy, 2,4,6-trimethylphenoxy, 2,4,6-tri-t-butylphenoxy, 1-naphthyloxy, 2-naphthyloxy, 2-chlorophenoxy, 3-chlorophenoxy, 4-chlorophenoxy, 2-methoxyphenoxy, 3-methoxyphenoxy, 4-methoxyphenoxy, 2-benzylphenoxy, 4-benzylphenoxy, 2-methylcarbonylphenoxy, and 4-methylcarbonylphenoxy.

More preferred examples include phenyl, 2,4-di-t-butylphenoxy, and 2,4,6-tri-t-butylphenoxy.

The above aryloxy groups represented by $R^8$ and $R^9$ may further have a substituent. Examples of the substituent include the above-described substituents that the alkyl groups represented by $R^8$, $R^9$, and $R^{10}$ may have.

In general formula (C-4), from the viewpoint of compatibility between polyester having a naphthalene structure and the compound having a structure represented by general formula (C-4), $R^8$ and $R^9$ are preferably alkoxy groups or aryloxy groups, and $R^{10}$ is preferably an alkyl group or an aryl group.

Examples of the above-described divalent or higher valent group serving as a linking group in the compound having a structure represented by general formula (C-4) include divalent or higher valent groups derived by removing one or more hydrogen atoms from the substituents that the above-described alkyl groups represented by $R^8$, $R^9$, and $R^{10}$ may have (divalent groups if one hydrogen atom is removed from the substituents, and trivalent groups if two hydrogen atoms are removed from the substituents) and combinations of two or more of these groups. These divalent or higher valent groups are preferably divalent to hexavalent groups, more preferably divalent to tetravalent groups. The divalent or higher valent groups are preferably organic groups.

The divalent or higher valent groups may further have a substituent. Examples of the substituent include the above-described substituents that the alkyl groups represented by $R^8$, $R^9$, and $R^{10}$ may have.

The divalent or higher valent groups preferably have a molecular weight of 10 to 1,000.

Of the above divalent or higher valent groups and a single bond, a single bond and divalent or higher valent groups derived by removing one or more hydrogen atoms from amino groups, alkyl groups, aryl groups, bis-aryl groups (arylaryl groups), arylalkylaryl groups, aryloxyaryl groups, alkoxyalkyl groups, alkoxyaryl groups, and alkylaryl groups are preferred.

When the compound having a structure represented by general formula (C-4) is a compound in which a plurality of structures represented by general formula (C-4) are present in one molecule, the number of phosphorus atoms in one molecule is preferably 2 or more and 20 or less, more preferably 2 or more and 10 or less, still more preferably 2 or more and 5 or less.

Specific examples of the compound having a structure represented by general formula (C-4) are given below. However, these examples are not intended to limit the present invention.

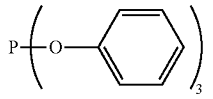
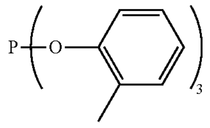
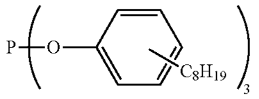
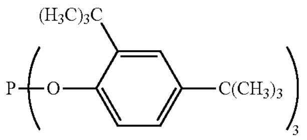
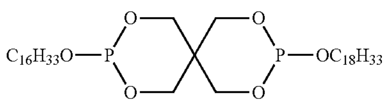
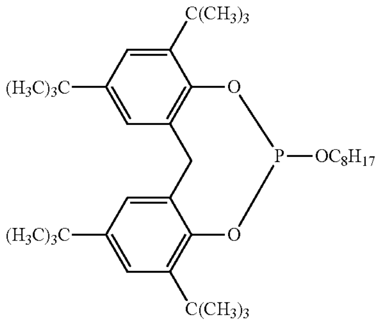
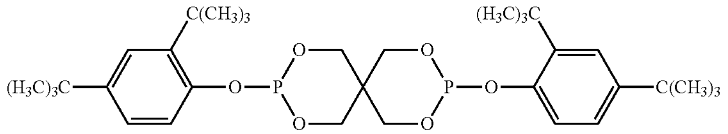
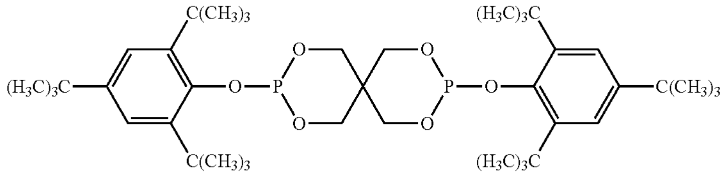
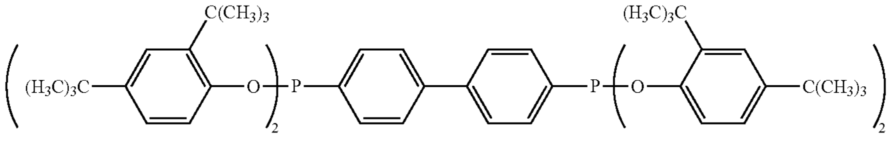

-continued

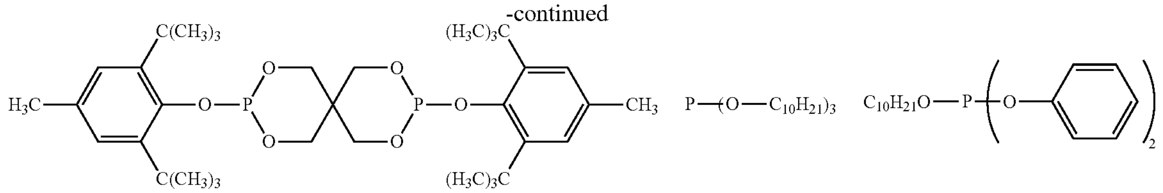

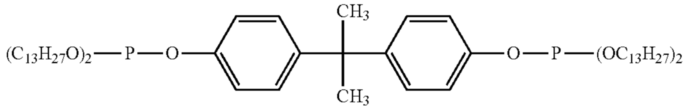

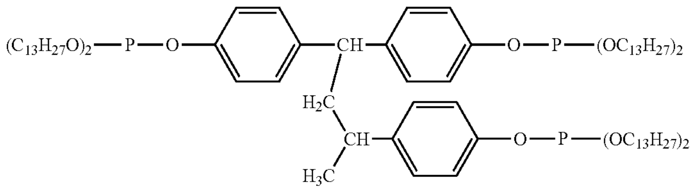

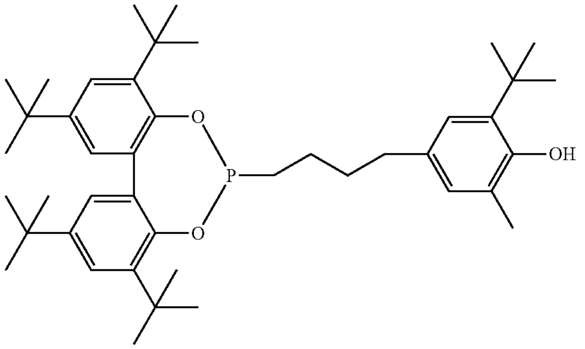

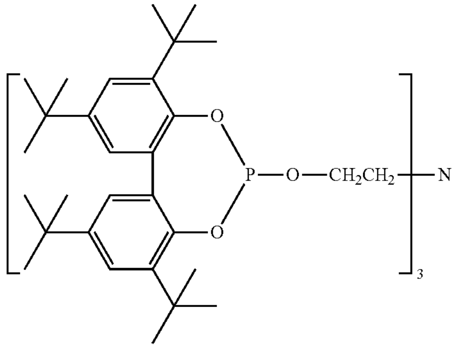

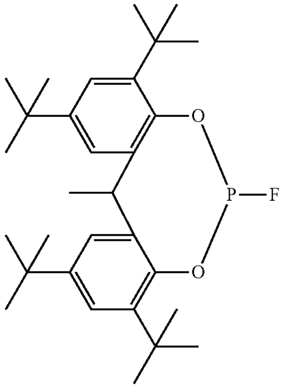

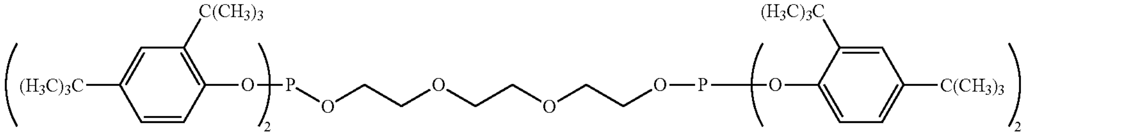

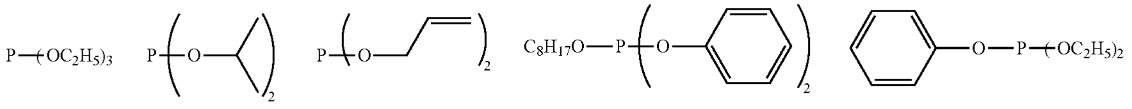

As the compound having a structure represented by general formula (C-4), phosphorous 5 acid ester compounds described in JP2011-527357A are also suitable for use.

The component (C-5) is a compound represented by general formula (C-5) below.

$R^{11}$—S—$R^{12}$ general formula (C-5)

In general formula (C-5), $R^{11}$ and $R^{12}$ each represent an alkyl group. $R^{11}$ and $R^{12}$ may be linked to each other via a divalent or higher valent group or a single bond.

In the present invention, compounds having a structure represented by general formula (C-5) include, in addition to the compound represented by general formula (C-5), the following compounds (c) and (d).

(c) Compounds having a structure in which a monovalent group derived by removing one hydrogen atom from $R^{11}$ or $R^{12}$ is linked to at least one of $R^{11}$ or $R^{12}$ of one or more (preferably an integer of 1 to 3) other compounds represented by general formula (C-5) via a divalent or higher valent group or a single bond, and (d) compounds having a structure in which a divalent or higher valent group derived by removing a total of two or more hydrogen atoms from at least one group selected from the group consisting of $R^{11}$ and $R^{12}$ (e.g., a divalent group if two hydrogen atoms are removed, or a trivalent group if three hydrogen atoms are removed) is linked to at least one of $R^{11}$ or $R^{12}$ of one or more (preferably an integer of 1 to 3) other compounds represented by general formula (C-5) via a divalent or higher valent group or a single bond.

That is, in the present invention, compounds having a structure represented by general formula (C-5) are meant to include the compound represented by general formula (C-5) and compounds having a structure in which a plurality of structures represented by general formula (C-5) are present in one molecule.

The alkyl groups represented by $R^{11}$ and $R^{12}$ are linear, branched, or cyclic substituted or unsubstituted alkyl groups. The alkyl groups have preferably 1 to 50 carbon atoms, more preferably 2 to 30 carbon atoms, particularly preferably 2 to 20 carbon atoms. Preferred examples include methyl, ethyl, n-propyl, isopropyl, cyclopropyl, butyl, isobutyl, t-butyl, s-butyl, pentyl, isopentyl, neopentyl, t-pentyl, hexyl, cyclohexyl, heptyl, cyclopentyl, octyl, 2-ethylhexyl, nonyl, decyl, dodecyl, tetradecyl, hexadecyl, octadecyl, eicosyl, docosyl, and triacontyl. More preferred are methyl, ethyl, n-propyl, isopropyl, butyl, isobutyl, t-butyl, s-butyl, pentyl, isopentyl, neopentyl, hexyl, cyclohexyl, octyl, 2-ethylhexyl, dodecyl, hexadecyl, and octadecyl, and still more preferred are methyl, ethyl, n-propyl, isopropyl, butyl, t-butyl, pentyl, isopentyl, hexyl, cyclohexyl, octyl, 2-ethylhexyl, dodecyl, hexadecyl, and octadecyl.

Examples of substituents of the substituted alkyl groups represented by $R^{11}$ and $R^{12}$ include the above-described substituents that the alkyl groups represented by $R^8$, $R^9$, and $R^{10}$ in general formula (C-4) may have.

Of the substituted alkyl groups represented by $R^{11}$ and $R^{12}$, alkoxycarbonylalkyl groups are preferred. The alkoxycarbonyl groups of the alkoxycarbonylalkyl groups have preferably 2 to 50 carbon atoms, more preferably 5 to 30 carbon atoms, particularly preferably 9 to 20 carbon atoms.

The divalent or higher valent group serving as a linking group in the compound having a structure represented by general formula (C-5) can be the same as the divalent or higher valent group serving as a linking group described in general formula (C-4), and a preferred range is also the same.

Specific examples of the compound having a structure represented by general formula (C-5) are given below. However, these examples are not intended to limit the present invention.

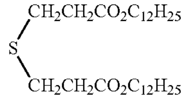

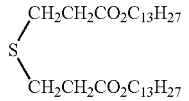

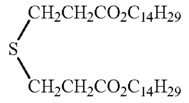

-continued

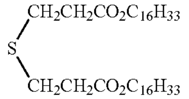

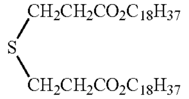

C—$(CH_2OCOCH_2CH_2SC_{12}H_{25})_4$

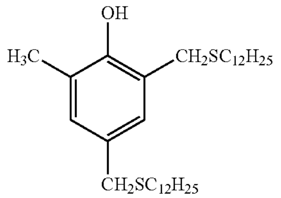

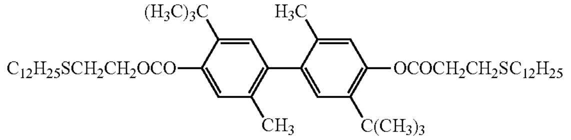

The component (C-6) is a compound having a structure represented by general formula (C-6) below.

general formula (C-6)

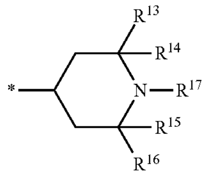

In general formula (C-6), $R^{13}$ to $R^{16}$ each represent a hydrogen atom or an alkyl group having 1 to 12 carbon atoms (preferably 1 to 8 carbon atoms, more preferably 1 to 5 carbon atoms), provided that $R^{13}$ to $R^{16}$ do not simultaneously represent hydrogen atoms.

Specific examples of the alkyl groups represented by $R^{13}$ to $R^{16}$ include methyl, ethyl, n-butyl, isopropyl, s-butyl, t-butyl, t-pentyl, t-hexyl, and t-octyl. Preferably, $R^{13}$ to $R^{16}$ are primary (linear) alkyl groups, and more preferably, all of $R^{13}$ to $R^{16}$ are primary (linear) alkyl groups (particularly preferably methyl groups).

In general formula (C-6), $R^{17}$ represents a hydrogen atom, an alkyl group having 1 to 18 carbon atoms (preferably 1 to 10 carbon atoms, more preferably 1 to 5 carbon atoms, still more preferably 1 to 3 carbon atoms, even more preferably 1 or 2 carbon atoms), or —$OR^{18}$, where $R^{18}$ represents a hydrogen atom or a linear, branched, or cyclic alkyl group having 1 to 20 carbon atoms (preferably 1 to 12 carbon atoms). In particular, when $R^{17}$ is-$OR^{18}$ autopolymerization of the epoxy resin can be suppressed. Due to the piperidine skeleton, the nitrogen atom to which "—$OR^{18}$" is bonded is in a bulky environment. Thus, N-oxyl radical resulting from trapping of a radical is stabilized, and the N—OR structure is readily regenerated. These are preferred in terms of heat resistance and sterilization resistance of an adhesive cured product.

In general formula (C-6), * represents a bonding site in the compound.

From the viewpoint of heat resistance and sterilization resistance of an adhesive cured product, the component (C-6) preferably includes at least one of a compound (component (C-6-1)) represented by general formula (C-6-1) below or a compound (component (C-6-2)) having a constituent (preferably a repeating unit) represented by general formula (C-6-2) below, more preferably includes the component (C-6-2). The component (C-6-1) is preferred because it is readily diffused inside the adhesive cured product and readily traps radicals. The component (C-6-2) is less likely to liquate out of the adhesive cured product.

In the component (C-6), the total content of the component (C-6-1) and the component (C-6-2) is not particularly limited. For example, the total content is preferably 50 mass % or more, more preferably 80 mass % or more, still more preferably 90 mass % or more, and may be 100 mass %.

general formula (C-6-1)

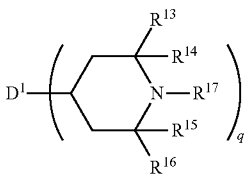

general formula (C-6-2)

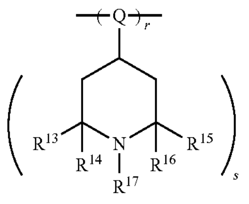

In the formulae, $R^{13}$ to $R^{17}$ respectively have the same definitions as $R^{13}$ to $R^{17}$ in general formula (C-6), and preferred ranges are also the same. q represents an integer of 2 or greater (preferably an integer of 2 to 10), and D1 represents a q-valent linking group. s represents 1 or 2. r represents a positive integer, preferably within the range of degrees of polymerization described later. Q represents a (s+2)-valent linking group, such as a group including an aromatic hydrocarbon group, a group including an imino group ($NR^N$), or a group including a triazine linking group. Specific examples of $R^N$ include a hydrogen atom, alkyl groups having 1 to 20 carbon atoms, and piperidyl-containing groups represented by general formula (C-6).

The molecular weight of the linking group represented by $D^1$ is preferably 100 to 1,000, more preferably 180 to 600. The molecular weight of the linking group represented by Q is preferably 100 to 1,000, more preferably 180 to 600.

The compound having a structure represented by general formula (C-6) is more preferably a compound represented by any of general formulae (CC-1) to (CC-3), (CC-6), (CC-7), and (CC-8) below, a polymer or oligomer having, in its repeating unit, a structure represented by general formula (CC-4) below (preferably a polymer or oligomer having a repeating unit represented by any of general formulae (CC-4-1) to (CC-4-3)), or a polymer or oligomer having a repeating unit represented by general formula (CC-6) below.

(CC-1)

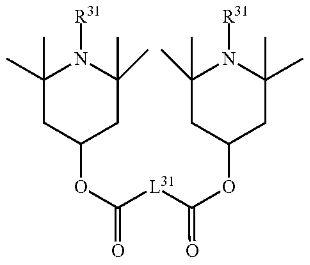

(CC-2)

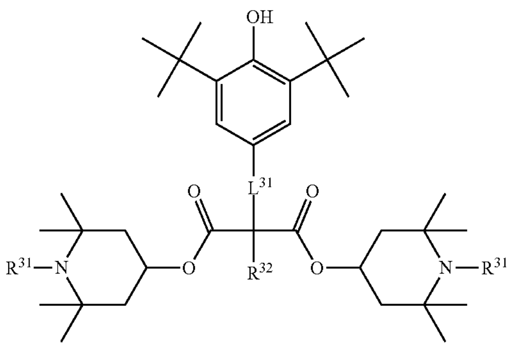

(CC-3)

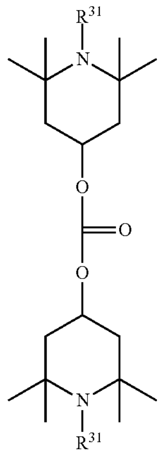

(CC-4)

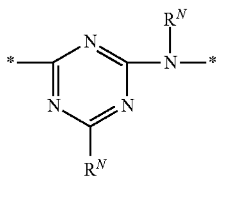

(CC-5)

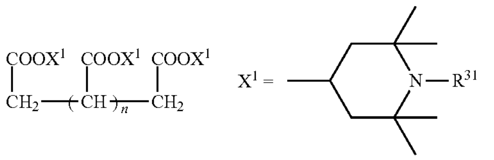

-continued (CC-4-1)

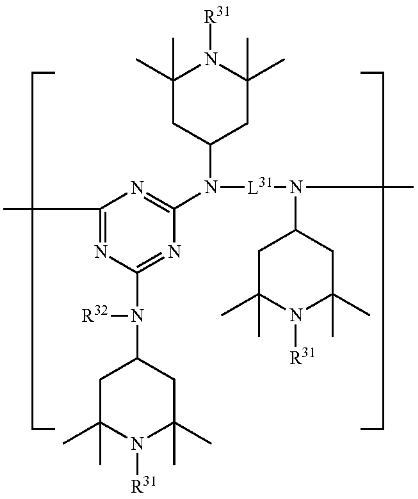

(CC-4-2)

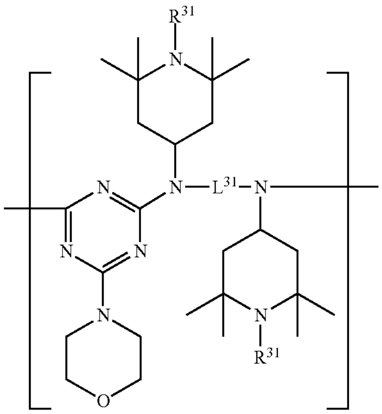

(CC-4-3)

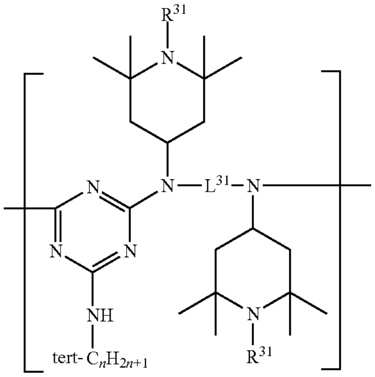

-continued (CC-6)

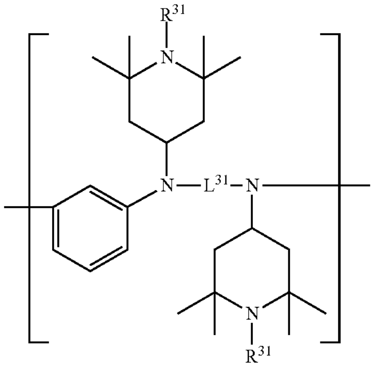

(CC-7)

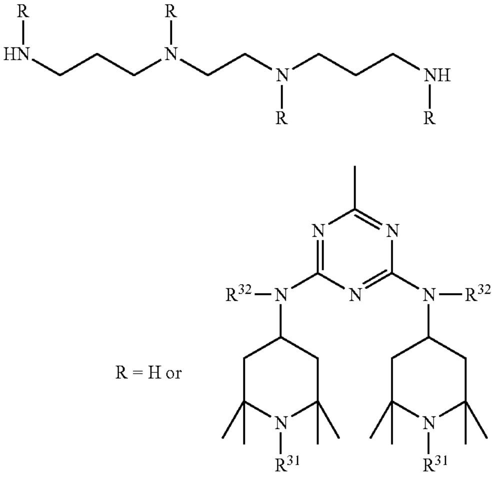

R = H or (CC-8)

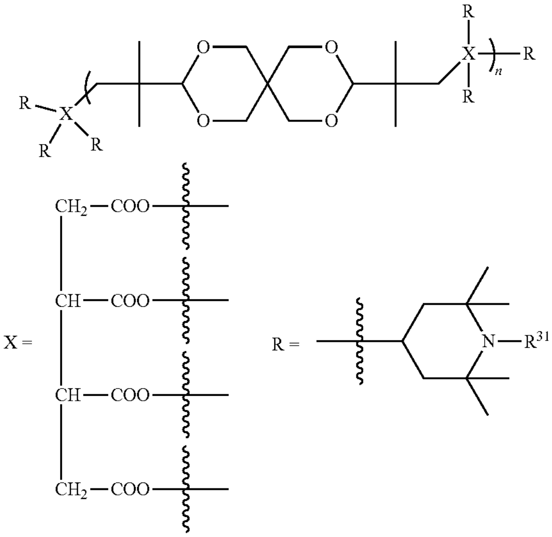

X =

R =

In the above formulae, $R^{31}$ has the same definition as $R^{17}$ in general formula (C-6), and preferred forms are also the same.

$R^{32}$ represents a hydrogen atom or an alkyl group having 1 to 20 carbon atoms (preferably 1 to 12 carbon atoms, more preferably 1 to 8 carbon atoms, still more preferably 1 to 6 carbon atoms). $L^{31}$ represents a single bond or an alkylene group having 1 to 20 carbon atoms (preferably 1 to 10 carbon atoms). RN has the same definition as RN in general formula (C-6). n represents an integer of 1 to 20 (preferably 1 to 10).

(In General Formula (CC-4-3), n Represents an Integer of 4 to 20 (Preferably 4 to 10)).

In general formula (CC-4), * represents a bonding site in the compound. In general formula (CC-7), at least one R is not H, but a group including triazine. In general formula (CC-8), the wavy lines represent a bonding site.

When the compound having a structure represented by general formula (C-6) is a polymer or oligomer, the number of the repeating units (the degree of polymerization) is preferably 2 to 100, more preferably 2 to 50, still more preferably 2 to 10. The terminal structures of the polymer or oligomer are not particularly limited, and may each be, for example, a hydrogen atom, a substituted or unsubstituted amino group, or a substituted or unsubstituted triazyl group.

The component (C-7) is a compound having a structure represented by general formula (C-7) below.

general formula (C-7)

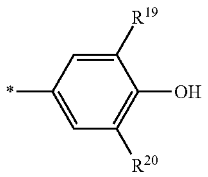

In general formula (C-7), $R^{19}$ and $R^{20}$ each represent a hydrogen atom, an alkyl group having 1 to 12 carbon atoms (preferably an alkyl group having 1 to 8 carbon atoms, e.g., a methyl group, an ethyl group, a n-butyl group, an isopropyl group, a sec-butyl group, a t-butyl group, a t-pentyl group, a t-hexyl group, or a t-octyl group), or an aralkyl group having 7 to 36 (preferably 7 to 30) carbon atoms. At least one of $R^{19}$ or $R^{20}$ is preferably a secondary alkyl group or a tertiary alkyl group, and at least one of $R^{19}$ or $R^{20}$ is more preferably a tertiary alkyl group. It is also preferred that both $R^{19}$ and $R^{20}$ be tertiary alkyl groups (preferably t-butyl groups). * represents a bonding site in the compound.

From the viewpoint of heat resistance and sterilization resistance of an adhesive cured product, the component (C-7) preferably includes at least one of a compound represented by general formula (C-7-1) below (component (C-7-1)) or a compound represented by general formula (C-7-2) below (component (C-7-2)). In the component (C-7), the total content of the component (C-7-1) and the component (C-7-2) is not particularly limited. For example, the total content is preferably 50 mass % or more, more preferably 80 mass % or more, still more preferably 90 mass % or more, and may be 100 mass %.

general formula (C-7-1)

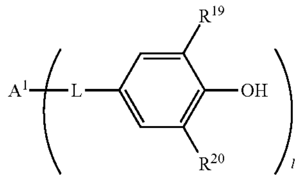

-continued general formula (C-7-2)

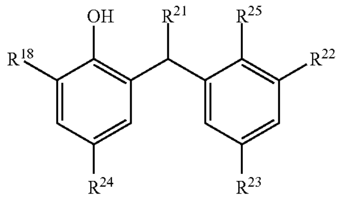

In the general formulae, $R^{19}$ and $R^{20}$ respectively have the same definitions as $R^{19}$ and $R^{20}$ in general formula (C-7).

L represents a single bond or a divalent linking group. Lis preferably an alkylene group having 1 to 10 carbon atoms (preferably 1 to 5 carbon atoms), an alkenylene group having 2 to 10 carbon atoms (preferably 2 to 5 carbon atoms), or a group represented by $-L^1-C(=O)-O-L^2-$. Here, $L^1$ and $L^2$ each represent a single bond, an alkylene group having 1 to 10 carbon atoms (preferably 1 to 5 carbon atoms), a carbonyl group, an oxygen atom, or a combination thereof.

t is an integer of 2 to 4, and $A^1$ represents a divalent to tetravalent linking group. $A^1$ is preferably a divalent to tetravalent organic group, and the number of carbon atoms of the organic group is preferably 1 to 20, more preferably 1 to 15, still more preferably 1 to 12, even more preferably 1 to 10.

When t is 2 and $A^1$ is a divalent organic group, $A^1$ is preferably a divalent aliphatic group (preferably an alkylene group) having 1 to 10 carbon atoms (preferably 1 to 5 carbon atoms) or an arylene group having 6 to 22 carbon atoms (preferably 6 to 14 carbon atoms).

When t is 3 and $A^1$ is trivalent linking group, $A^1$ is preferably a group represented by general formula ($A^1L$) below. In general formula ($A^1L$), * represents a linking site.

general formula ($A^1L$)

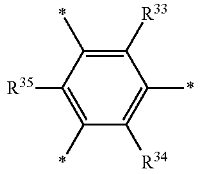

In general formula ($A^1L$), * represents a bonding site. $R^{33}$ to $R^{35}$ each represent a hydrogen atom or an alkyl group having 1 to 10 carbon atoms (preferably 1 to 6 carbon atoms, more preferably 1 to 3 carbon atoms).

When tis 4 and $A^1$ is a tetravalent linking group, $A^1$ is preferably a quaternary carbon atom. In this case, the linking group L is preferably a group represented by $-L^1-C(=O)-O-L^2-$. Here, $L^1$ and L' respectively have the same definitions as $L^1$ and $L^2$ above.

$R^{21}$ to $R^{24}$ each have the same definition as $R^{19}$. $R^{25}$ is a reactive organic substituent, preferably a vinyl-containing group, more preferably a (meth)acryloyl-containing group.

Specific examples of the component (C-7) include compounds used in EXAMPLES described later, but these examples are not intended to limit the present invention.

In the adhesive according to the present invention, the content of the radical scavenger is not particularly limited, and is, for example, preferably 0.1 parts by mass or more and 30 parts by mass or less, more preferably 0.5 parts by mass or more and 25 parts by mass or less, more preferably 3 parts by mass or more and 18 parts by mass or less, still more preferably 2 parts by mass or more and 8 parts by mass or less, relative to 100 parts by mass of the epoxy resin serving as the component (A).

Cured Product

A cured product according to the present invention is formed by curing the adhesive according to the present invention. That is, the cured product according to the present invention is used as a member constituting an adhesive joint of an endoscope. The curing temperature of the adhesive according to the present invention is not particularly limited, and is appropriately adjusted depending on the purpose in consideration of, for example, the heat resistance of an adherend and the curing time. Mixing of the components is preferably performed while removing bubbles, and thus is usually performed under reduced pressure. The curing temperature is preferably 100° C. or lower, more preferably 90° C. or lower, still more preferably 80° C. or lower. For the curing reaction to sufficiently proceed, the curing temperature is preferably 0° C. or higher, more preferably 10° C. or higher. The curing reaction time can be appropriately set depending on the purpose. Typically, the curing reaction is performed for 1.5 to 200 hours to obtain the cured product.

Endoscope

In an endoscope according to the present invention, a constituent member is fixed with the cured product according to the present invention. The phrase "a constituent member is fixed with the cured product according to the present invention" means that at least one member constituting the endoscope is fixed to a supporting member through the cured product according to the present invention.

An example of the endoscope (electronic endoscope) according to the present invention will be described. Electronic endoscopes are incorporated with a flexible tube for an endoscope (hereinafter a flexible tube for an endoscope may be referred to simply as a "flexible tube") and are widely used as medical instruments. In the example illustrated in FIG. 1, an electronic endoscope 2 includes an insertion section 3 to be inserted into a body cavity, a main-body operation section 5 connected to the proximal end portion of the insertion section 3, and a universal cord 6 to be connected to a processor device or a light source device. The insertion section 3 is composed of a flexible tube 3*a* connected to the main-body operation section 5, an angle portion 3*b* connected to the flexible tube 3*a*, and a tip portion 3*c* connected to the distal end of the angle portion 3*b* and mainly formed of a metal (e.g., stainless steel) member. An imaging device (not illustrated) for imaging a body cavity is built in the tip portion 3*c*. The flexible tube 3*a*, which occupies most of the length of the insertion section 3, is flexible over substantially the entire length thereof. In particular, a portion to be inserted into a body cavity or the like has a more flexible structure.

In FIG. 1, a plurality of channels (tubes, not illustrated) are formed that extend from the main-body operation section 5 to the distal end surface of the tip portion 3*c* through the insertion section 3 along the axis direction of the insertion section 3.

Figure 2:
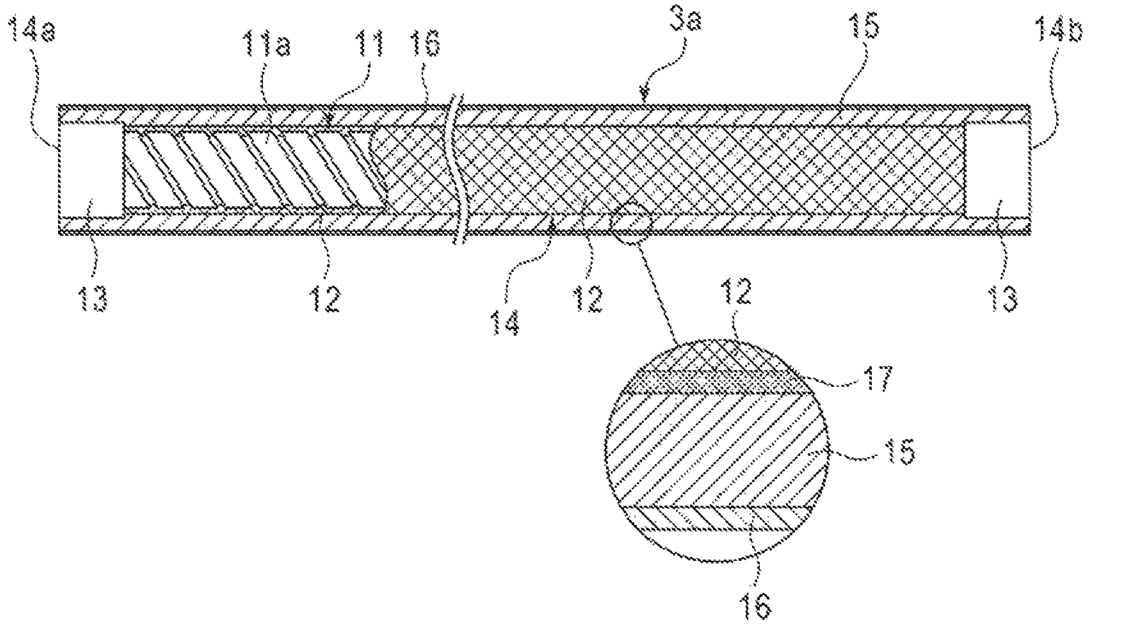
FIG. 2 is a partial sectional view illustrating a configuration of an insertion section of the endoscope illustrated in FIG. 1.

The flexible tube 3*a* in FIG. 1 is configured such that a resin layer 15 covers the outer peripheral surface of a flexible-tube base 14, as illustrated in FIG. 2.

Reference numeral 14*a* denotes the distal side (tip portion 3*c* side), and reference numeral 14*b* denotes the proximal side (main-body operation section 5 side).

The flexible-tube base 14 includes a spiral tube 11, which is disposed on the innermost side and formed by spirally winding a metal strip 11*a*, and a tubular net 12, which covers the spiral tube 11 and is formed by braiding metal wires. Caps 13 are fitted to opposite ends of the flexible-tube base 14. The resin layer 15 is bonded to the flexible-tube base 14 with an adhesive cured product layer 17 interposed therebetween. The adhesive cured product layer 17 can be formed by applying and curing the adhesive according to the present invention. While the adhesive cured product layer (adhesive joint) 17 is illustrated as a layer having a uniform thickness for convenience of illustration, the adhesive cured product layer 17 need not necessarily be in such a form and may be indeterminately interposed between the resin layer 15 and the flexible-tube base 14. The adhesive cured product layer 17 may rather have substantially no thickness such that the resin layer 15 and the flexible-tube base 14 are substantially directly bonded together.

The outer surface of the resin layer 15 is coated with a coat layer 16 having chemical resistance and containing, for example, fluorine. To clearly illustrate the layer structure, the adhesive cured product layer 17, the resin layer 15, and the coat layer 16 are illustrated as being thick relative to the diameter of the flexible-tube base 14.

Figure 3:
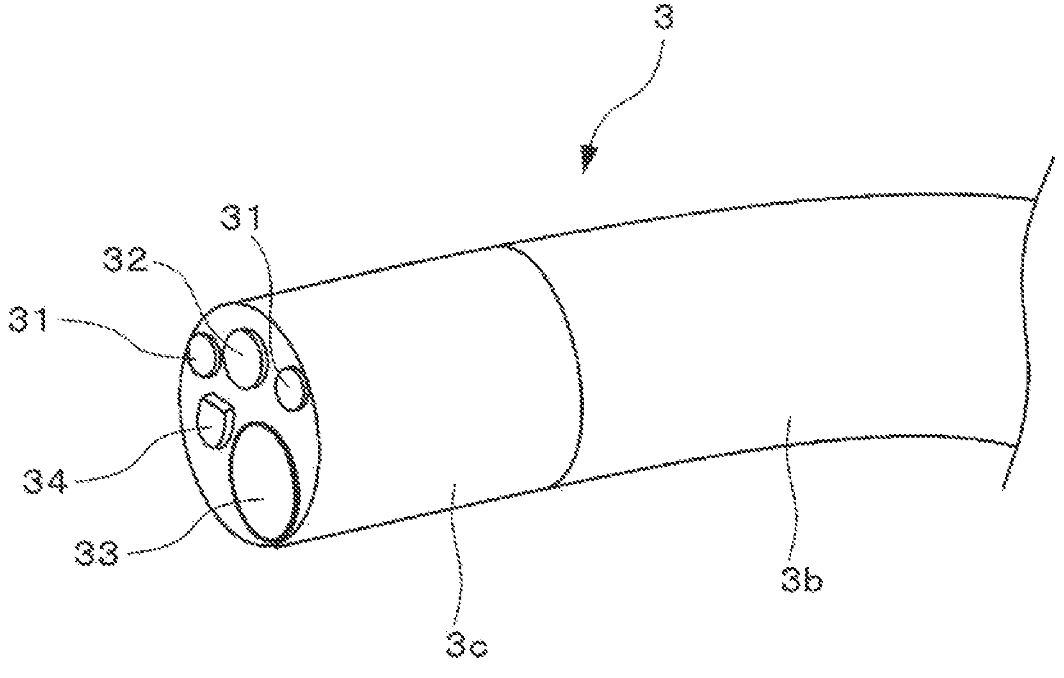
FIG. 3 is an external perspective view of a tip portion of the insertion section.

As illustrated in FIG. 3, an illumination window 31, an observation window 32, and a forceps port 33 are formed in the distal end surface of the tip portion 3*c*. To wash the distal end surface as required, a nozzle 34 for sending water and air is formed. The illumination window 31, the observation window 32, the forceps port 33, and the nozzle 34 communicate with the main-body operation section 5 through the channels.

Figure 4:
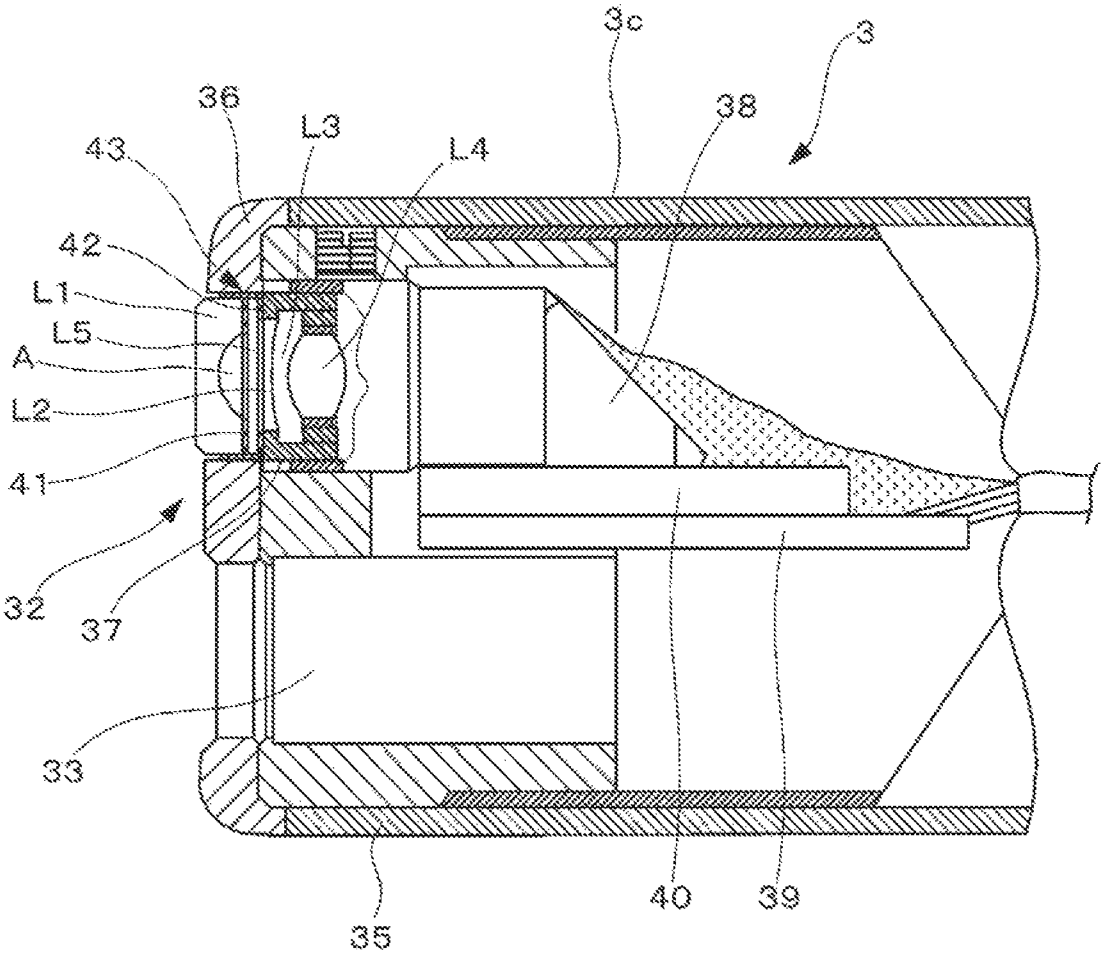
FIG. 4 is a partially cut-away partial sectional view of the tip portion, without hatching that shows sections of lenses and a prism.

As illustrated in FIG. 4, the tip portion 3*c* is composed of a tip-portion main body 35 made of metal and an end cap 36 made of an electrically insulating material.

An observation unit 43, which is an optical device, is disposed in the observation window 32. The observation unit 43 includes a lens holder 37, and in the lens holder 37, an objective optical system composed of lenses L1 to L5 is fixed with adhesive cured products 41 and 42. The adhesive cured products 41 and 42 can be formed by applying and curing the adhesive according to the present invention. In the objective optical system, A is an air layer. A prism 38 is bonded and fixed to an end face of the lens holder 37. The optical axis of the objective optical system can be bent at a right angle by the prism 38. The prism 38 is fixed to a solid-state imaging element 40. The solid-state imaging element 40 is fixed to a substrate 39. Also for the fixing of these components, the adhesive according to the present invention can be applied.

Method for Producing Endoscope

A method for producing an endoscope according to the present invention is not particularly limited as long as the method includes fixing an endoscope-constituting member by using the adhesive according to the present invention. For steps other than fixing of an endoscope-constituting member, usual production steps can be employed to produce the endoscope according to the present invention.

The endoscope-constituting member to be fixed may be made of any material, and may be, for example, a resin member, a metal member, or a glass member. The endoscope-constituting member can be fixed to a supporting member or the like constituting the endoscope, for example, in the following manner. The components included in the adhesive according to the present invention are mixed together preferably under reduced pressure, and the resulting mixture is then injected into or applied to a target portion and heated at −10° C. to 60° C. (preferably 0° C. to 60° C., more preferably 10° C. to 50° C.) for 1.5 to 200 hours.

Specific examples of how the adhesive is used in the method for producing an endoscope according to the present invention will be described below, but these examples are not intended to limit the present invention.

Examples of resin members among endoscope-constituting members fixed with the adhesive according to the present invention include tubes inserted into an insertion section of an endoscope. Examples of resin materials forming the tubes include fluorocarbon resins such as Teflon (registered trademark), polysulfone, polyester, polyolefin, and silicone. The adhesive according to the present invention can be used, for example, to bond a metal member or a glass member constituting an insertion section of an endoscope to any of the above tubes (to fix the metal member or the glass member to any of the above tubes).

As described above, the adhesive according to the present invention can also be used to form the adhesive cured product layer 17 in FIG. 2. The adhesive according to the present invention can also be used to bond together the resin layer 15 and the coat layer 16 in FIG. 2.

The adhesive according to the present invention can be used for outer-surface finishing and fixing of an end of a flexible outer cover tube (the resin layer 15) (the end on the distal side (angle portion 3*b* side) of the flexible tube 3*a*). Specifically, a string is tightly bound around an end of the resin layer 15 of the flexible tube 3*a* to fix the resin layer 15 to the member thereinside, and then the adhesive is applied so as to coat the string and cured. The configuration in which the outermost layer on the distal-side end of the flexible tube 3*a* is formed of the adhesive according to the present invention reduces the likelihood of raveling of the string on the distal-side end and facilitates the insertion of the insertion section into a body cavity.

The adhesive according to the present invention can be used for at least one of bonding of the tip portion 3*c* and the angle portion 3*b* or bonding of the insertion section 3 and the main-body operation section 5. For example, the tip portion 3*c* and the angle portion 3*b* are bonded together using the adhesive according to the present invention, after which a string is tightly wound around the adhesive joint between the tip portion 3*c* and the angle portion 3*b* and a portion near the adhesive joint to reinforce the bonding, and the adhesive is applied so as to coat the string and cured. The bonding of the insertion section 3 and the main-body operation section 5 is performed in the same manner.

The adhesive according to the present invention can also be used to fix various tubes inserted into the insertion section of the endoscope to at least one of the tip portion 3*c* or the main-body operation section 5.

The adhesive according to the present invention is also preferably used, at the tip portion 3*c*, to seal the illumination window 31 and the observation window 32 (to fix the glass members). A thick coating of the adhesive can smoothen the outer corners of the lenses and block the entrance of light from the lateral sides of the lenses.

The adhesive according to the present invention can be used to fix members, for example, to assemble the imaging device built in the tip portion 3*c*, to bond parts together, or to seal the solid-state imaging element 40. The imaging device has an optical system composed of a plurality of optical parts, such as the lenses L1 to L5 and the prism 38, and has the solid-state imaging element 40, such as a charge coupled device (CCD), that photoelectrically converts an optical image formed by the optical system into an imaging signal. The adhesive according to the present invention can be used, for example, for bonding of optical parts including the lenses L1 to L5 and the prism 38 made of materials such as glass and bonding of the lenses L1 to L5, the prism 38, and the like to the substrate 39 made of resin or metal. This bonding can fix the glass members and can fix the metal member.

The adhesive according to the present invention can be used for bond-fixing and sealing of the solid-state imaging element 40 and the substrate 39. This bonding can fix the metal members constituting the solid-state imaging element, the substrate, and the like.

As described above, the method for producing an endoscope according to the present invention includes a step of fixing an endoscope-constituting member by using the adhesive according to the present invention.

EXAMPLES

The present invention will now be described in more detail with reference to Examples, but the Examples should not be construed as limiting the present invention. In the following Examples, "room temperature" means 25° C. The amount of a component means the amount of the component itself. Specifically, when a raw material includes a solvent, the amount of the solvent is excluded.

Preparation Example: Preparation of Adhesive

Components (A) to (C) shown in Table 1 below were mixed together in a ratio (parts by mass) shown in Table 1 below, and using a "THINKY MIXER (AWATORI RENTARO) ARV-310 (trade name, manufactured by THINKY CORPORATION)", the resulting mixture was defoamed for 5 minutes with stirring at 2,000 rpm under a reduced pressure of 1.0 Pa at room temperature to obtain an adhesive. In Production Examples 1 and 2 below, adhesives immediately after being prepared were used.

Production Example 1: Production of Test Sheet (Sheet-Like Adhesive Cured Product)

The adhesive obtained in Preparation Example above was cured at 80° C. for 24 hours with a MINI TEST PRESS (manufactured by Toyo Seiki Seisaku-sho, Ltd.) to obtain a test sheet 100 mm long×100 mm wide×0.4 mm thick. For the test sheet, test sheets for use in Test Examples 1 and 2 below were produced.

Production Example 2: Production of Test Piece (Test Piece of Adhering Stainless Steel (SUS) Substrates)

Using the adhesive obtained in Preparation Example above, a test piece (test piece of adhering SUS substrates) was produced in accordance with JIS K 6850 (1999). The substrates used were SUS304 plates (manufactured by MISUMI Corporation) having a width of 25 mm, a length of 10 cm, and a thickness of 2 mm. The area of adhesion was 25 mm×10 mm. The spacer used was a wire spacer (manufactured by AS ONE Corporation) having a thickness of 0.1 mm. The adhesive was cured at 80° C. for 24 hours to obtain a test piece (test piece of adhering SUS substrates) formed of two SUS304 plates glued together with an adhesive cured product.

Test Example 1: Ozone Water Treatment Resistance Test

Two test sheets were placed in a glass case 20 cm long×20 cm wide×1 cm thick without overlapping each other. The glass case was set in a flow path of an ozone water generator (trade name, "OWM-10L10P" manufactured by EcoDesign, Inc.), and ozone water with an ozone concentration of 3 ppm was flowed at a flow rate of 1 L/min for 3 hours to perform treatment. The test sheets were taken out of the glass case and washed with distilled water.

Appearance Evaluation

One of the test sheets washed with distilled water was wiped clean of surface moisture and dried by being left to stand in an environment at 25° C. for 8 hours. This test sheet was visually observed and evaluated according to the following evaluation criteria. In this test, S, A, and B are acceptable.

Evaluation Criteria

S: The sheet surface had no roughness and no haze.

A: The sheet surface had slight roughness but no haze.

B: The sheet surface had slight roughness and such a slight haze that is translucent.

C: The sheet surface had roughness and lost transparency because of haze.

Tensile Strength Retention Evaluation

The other one of the test sheets washed with distilled water was dried at 23° C.×50% RH (relative humidity) for 24 hours. The tensile strength (I) (MPa) of the test sheet before being subjected to ozone water treatment and the tensile strength (II) (MPa) of the test sheet after being subjected to ozone water treatment were measured at room temperature using a Tensilon universal material testing instrument (trade name: RTF-1210, manufactured by A & D Company, Limited).

The tensile strength retention X (%) was calculated by the following formula and evaluated according to the following evaluation criteria. In this test, S, A, and B are acceptable. Tensile strength retention X (%)=100×tensile strength (II)/tensile strength (I)

Evaluation Criteria

S: The tensile strength retention X is 90% or more.

A: The tensile strength retention X is 80% or more and less than 90%.

B: The tensile strength retention X is 70% or more and less than 80%.

C: The tensile strength retention X is 60% or more and less than 70%.

D: The tensile strength retention X is less than 60%.

Test Example 2: Heat Resistance

Using a Tensilon universal material testing instrument (trade name: RTF-1210, manufactured by A & D Company, Limited), the adhesive strength (A) (MPa) of a test piece (not subjected to ozone water treatment) was measured at room temperature by gripping the ends of the two SUS304 plates and pulling them in opposite directions parallel to each other in the longitudinal direction.

Separately, the adhesive strength (MPa) of a test piece after being left to stand at a glass transition temperature (Tg)+10° C. for 24 hours and then further left to stand at 23° C. for 24 hours was measured in the same manner as described above to determine the adhesive strength (B) (MPa).

The glass transition temperature was determined by performing a dynamic viscoelastic measurement on a test sheet (test sheet produced using an adhesive having the same composition as that of the adhesive used to produce the test piece) by using DMS6100 (trade name, manufactured by SII Technology).

The adhesive strength retention Y (%) was calculated by the following formula and evaluated according to the following evaluation criteria. In this test, S, A, and B are acceptable. Adhesive strength retention Y (%)=100×adhesive strength (B)/adhesive strength (A)

Evaluation Criteria

S: The adhesive strength retention Y is 90% or more.

A: The adhesive strength retention Y is 80% or more and less than 90%.

B: The adhesive strength retention Y is 70% or more and less than 80%.

C: The adhesive strength retention Y is 60% or more and less than 70%.

D: The adhesive strength retention Y is less than 60%.

TABLE 1

| | Component (A) | | Component (B) | | Component (C) | | Test Example 1 Ozone water treatment resistance | | Test Example 2 Heat resistance | |
|---|---|---|---|---|---|---|---|---|---|---|
| | Type | Parts by mass | Type | Parts by mass | Type | Parts by mass | Appearance | Tensile strength evaluation | Tg (° C.) | Adhesive strength evaluation |
| Ex. 1 | A-1 | 100 | B-1 | 40 | C61 | 5 | A | B | 95 | A |
| Ex. 2 | A-2 | 100 | B-1 | 40 | C61 | 5 | A | B | 95 | A |
| Ex. 3 | A-3 | 100 | B-1 | 40 | C61 | 5 | A | B | 95 | A |
| Ex. 4 | A-1 | 100 | B-1 | 40 | C63 | 5 | A | A | 95 | A |
| Ex. 5 | A-2 | 100 | B-1 | 40 | C63 | 5 | A | A | 95 | A |
| Ex. 6 | A-3 | 100 | B-1 | 40 | C63 | 5 | A | A | 95 | A |
| Ex. 7 | A-1 | 100 | B-2 | 70 | C61 | 5 | A | B | 85 | A |
| Ex. 8 | A-1 | 100 | B-2 | 70 | C63 | 5 | A | A | 85 | A |
| Ex. 9 | A-2 | 100 | B-3 | 3 | C61 | 5 | A | B | 95 | A |
| Ex. 10 | A-2 | 100 | B-3 | 3 | C63 | 5 | A | A | 95 | A |
| Ex. 11 | A-2 | 100 | B-4 | 50 | C61 | 5 | A | A | 89 | S |
| Ex. 12 | A-2 | 100 | B-4 | 50 | C63 | 5 | S | S | 89 | S |
| Ex. 13 | A-2 | 100 | B-4 | 50 | C61 | 1 | A | B | 89 | A |
| Ex. 14 | A-2 | 100 | B-4 | 50 | C63 | 1 | S | A | 89 | A |
| Ex. 15 | A-2 | 100 | B-4 | 50 | C61 | 10 | A | A | 84 | A |
| Ex. 16 | A-2 | 100 | B-4 | 50 | C63 | 10 | S | S | 89 | A |
| Ex. 17 | A-2 | 100 | B-4 | 50 | C61 | 20 | B | A | 80 | A |
| Ex. 18 | A-2 | 100 | B-4 | 50 | C63 | 20 | A | S | 89 | A |
| Ex. 19 | A-2 | 100 | B-5 | 20 | C61 | 5 | A | B | 99 | A |
| Ex. 20 | A-2 | 100 | B-5 | 20 | C63 | 5 | A | A | 99 | A |

TABLE 1-continued

| | Component (A) | | Component (B) | | Component (C) | | Test Example 1 Ozone water treatment resistance | | Test Example 2 Heat resistance | |
|---|---|---|---|---|---|---|---|---|---|---|
| | Type | Parts by mass | Type | Parts by mass | Type | Parts by mass | Appearance | Tensile strength evaluation | Tg (° C.) | Adhesive strength evaluation |
| Ex. 21 | A-2 | 100 | B-6 | 50 | C63 | 5 | S | S | 88 | S |
| Ex. 22 | A-2 | 100 | B-7 | 50 | C63 | 5 | S | S | 95 | S |
| Ex. 23 | A-2 | 100 | B-8 | 50 | C63 | 5 | S | S | 90 | S |
| Ex. 24 | A-2 | 100 | B-9 | 20 | C61 | 5 | A | B | 95 | A |
| Ex. 25 | A-2 | 100 | B-10 | 20 | C61 | 5 | A | B | 99 | A |
| Ex. 26 | A-2 | 100 | B-11 | 40 | C61 | 5 | A | B | 90 | A |
| Ex. 27 | A-2 | 100 | B-4 | 50 | C62 | 5 | A | A | 89 | S |
| Ex. 28 | A-2 | 100 | B-4 | 50 | C64 | 5 | A | A | 89 | S |
| Ex. 29 | A-2 | 100 | B-4 | 50 | C65 | 5 | A | A | 89 | S |
| Ex. 30 | A-2 | 100 | B-4 | 50 | C71 | 5 | B | A | 89 | A |
| Ex. 31 | A-2 | 100 | B-4 | 50 | C72 | 5 | B | A | 89 | A |
| Ex. 32 | A-2 | 100 | B-4 | 50 | C11 | 5 | B | B | 89 | B |
| Ex. 33 | A-2 | 100 | B-4 | 50 | C21 | 5 | B | B | 89 | B |
| Ex. 34 | A-2 | 100 | B-4 | 50 | C31 | 5 | B | B | 89 | B |
| Ex. 35 | A-2 | 100 | B-4 | 50 | C41 | 5 | B | B | 89 | B |
| Ex. 36 | A-2 | 100 | B-4 | 50 | C51 | 5 | B | B | 89 | B |
| CE. 1 | A-2 | 100 | B-1 | 40 | none | 0 | C | D | 95 | C |
| CE. 2 | A-2 | 100 | B-4 | 50 | none | 0 | C | D | 89 | C |
| CE. 3 | A-2 | 100 | X-1 | 50 | C63 | 5 | C | D | 95 | D |

Notes of Table

Ex: Example, CE: Comparative Example

Component (A): Epoxy Resin

A-1:

Bisphenol A diglycidyl ether (trade name "jER828", manufactured by Mitsubishi Chemical Corporation, epoxy equivalent: 190)

A-2:

Bisphenol F diglycidyl ether (trade name "EPICLON830", manufactured by DIC Corporation, epoxy equivalent: 170)

A-3:

Epoxy novolac resin (product number 406775, manufactured by Sigma-Aldrich, epoxy equivalent: 170)

Component (B): Epoxy Resin Curing Component

B-1:

Dicyandiamide (manufactured by Tokyo Chemical Industry Co., Ltd.)

B-2:

Pentaerythritol tetrakis(3-mercaptobutyrate) (trade name "Karenz MT (registered trademark) PE1", manufactured by Showa Denko K.K.)

B-3:

Triphenylphosphine (manufactured by Tokyo Chemical Industry Co., Ltd.)

B-4:

Polyether amine D230 (trade name, manufactured by Mitsui Fine Chemicals, Inc., number-average molecular weight: 230)

B-5:

Phenol resin (trade name "HF-1M", manufactured by Meiwa Plastic Industries, Ltd.)

B-6:

Polyether amine D400 (trade name, manufactured by Mitsui Fine Chemicals, Inc., number-average molecular weight: 400)

B-7:

Polyether amine T403 (trade name, manufactured by Mitsui Fine Chemicals, Inc., number-average molecular weight: 440)

B-8:

JEFFAMIN ED-600 (trade name, manufactured by Huntsman Corporation, number-average molecular weight: 600)

B-9:

1,6-Hexanediamine (manufactured by Tokyo Chemical Industry Co., Ltd.)

B-10:

m-Xylylenediamine (manufactured by Tokyo Chemical Industry Co., Ltd.)

B-11:

HV953U (trade name, manufactured by Nagase ChemteX Corporation, polyamidoamine, number-average molecular weight: 1,100)

X-1:

Boron trifluoride monoamine complex (manufactured by Aldrich)

Component (C): Radical Scavenger

C11: Component (C-1), trade name: Irgastab FS042, manufactured by Aldrich

C21: Component (C-2), trade name: Irganox HP-136, manufactured by ADEKA Corporation C31: Component (C-3), ascorbic acid C41: Component (C-4), trade name: ADK STAB HP-10, manufactured by ADEKA Corporation C51: Component (C-5), trade name: ADK STAB AO-412S, manufactured by ADEKA Corporation C61: Component (C-6-2), trade name: ADK STAB LA-63P, manufactured by ADEKA Corporation ($NR^{17}$ is N—$CH_3$)

C62: Component (C-6-1), trade name: Tinuvin 765, manufactured by BASF ($NR^{17}$ is N—$CH_3$)

C63: Component (C-6-2), trade name: Flamestab NOR 116, manufactured by BASF ($NR^{17}$ is N—O-cyclohexane)

C64: Component (C-6-2), trade name: Chimassorb 2020FDL, manufactured by BASF ($NR^{17}$ is N—H)

C65: Component (C-6-2), trade name: Chimassorb 944FDL, manufactured by BASF ($NR^{17}$ is N—H)

C71: Component (C-7-1), trade name: Irganox 1010, manufactured by BASF

C72: Component (C-7-2), trade name: Sumilizer GS, manufactured by Sumitomo Chemical Co., Ltd.

The results in Table 1 show the following.

The adhesives of Comparative Examples 1 and 2, each containing no component (C), were poor in both "appearance" evaluation and "tensile strength evaluation" of ozone water treatment resistance and were also poor in heat resistance. The adhesive of Comparative Example 3, in which a boron trifluoride monoamine complex was used instead of the component (B) specified in the present invention, was poor in both "appearance" evaluation and "tensile strength" evaluation of ozone water treatment resistance and was also poor in heat resistance.

By contrast, the adhesives of Examples 1 to 36 (adhesives according to the present invention) were at acceptable levels in all of ozone water treatment resistance ("appearance" evaluation and "tensile strength" evaluation) and heat resistance evaluation.

REFERENCE SIGNS LIST

2 electronic endoscope (endoscope)
3 insertion section
3*a* flexible tube
3*b* angle portion
3*c* tip portion
5 main-body operation section
6 universal cord
11 spiral tube
11*a* metal strip
12 tubular net
13 cap
14 flexible-tube base
14*a* distal side
14*b* proximal side
15 resin layer
16 coat layer
17 adhesive cured product layer
31 illumination window
32 observation window
33 forceps port
34 nozzle
35 tip-portion main body
36 end cap
37 lens holder
38 prism
39 substrate
40 solid-state imaging element
41 adhesive cured product
42 adhesive cured product
43 observation unit
L1 to L5 lens

What is claimed is:

1. An adhesive for an endoscope, comprising components (A) to (C) below,

Component (A): an epoxy resin

Component (B): an epoxy resin curing component

Component (C): a radical scavenger wherein the component (A) includes at least one of a bisphenol A epoxy resin, a bisphenol F epoxy resin, or a phenol novolac epoxy resin, the component (B) includes at least one of a phosphorus-containing compound, a polythiol compound, a dicyandiamide compound, a phenol compound, a polyamine compound having an unsubstituted amino group, an acid anhydride compound, or an imidazole compound, and the component (C) includes at least one of components (C-1) to (C-7) below, Component (C-1): a compound represented by general formula (C-1) below Component (C-2): a compound represented by general formula (C-2) below Component (C-3): a compound represented by formula (C-3) below Component (C-4): a compound represented by general formula (C-4) below Component (C-5): a compound represented by general formula (C-5) below Component (C-6): a compound having a structure represented by general formula (C-6) below Component (C-7): a compound having a structure represented by general formula (C-7) below general formula (C-1)

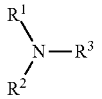

where $R^1$ and $R^2$ each represent a hydrogen atom, an aliphatic group, an acyl group, an aliphatic oxycarbonyl group, an aromatic oxycarbonyl group, an aliphatic sulfonyl group, or an aromatic sulfonyl group, $R^3$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group, $R^1$ and $R^2$, $R^2$ and $R^3$, or $R^1$ and $R^3$ may be bonded to each other to form a five- to seven-membered ring but do not form a piperidine skeleton, provided that $R^1$ and $R^2$ are not simultaneously hydrogen atoms and have a total of 7 or more carbon atoms, and $R^1$, $R^2$, and $R^3$ include no unsubstituted amino groups, general formula (C-2)

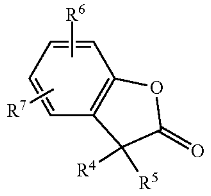

where $R^4$ to $R^7$ each represent a hydrogen atom, an alkyl group having 1 to 20 carbon atoms, or an aryl group having 6 to 15 carbon atoms, formula (C-3)

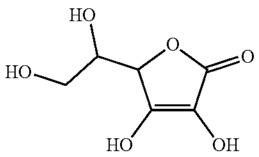

general formula (C-4)

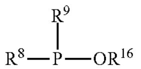

where $R^8$ and $R^9$ each represent an alkyl group, an aryl group, an alkoxy group, an aryloxy group, or a halogen atom, $R^{10}$ represents an alkyl group or an aryl group, and at least two of $R^8$, $R^9$, and $R^{10}$ may be linked to each other via a divalent or higher valent group or a single bond, $R^{11}—S—R^{12}$ general formula (C-5)

where $R^{11}$ and $R^{12}$ each represent an alkyl group, general formula (C-6)

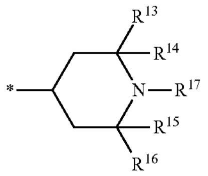

where $R^{13}$ to $R^{16}$ each represent a hydrogen atom or an alkyl group having 1 to 12 carbon atoms, $R^{17}$ represents a hydrogen atom, an alkyl group having 1 to 18 carbon atoms, or $OR^{18}$, where $R^{18}$ represents a hydrogen atom or an alkyl group having 1 to 20 carbon atoms, and * represents a bonding site, provided that $R^{13}$ to $R^{16}$ are not simultaneously hydrogen atoms, general formula (C-7)

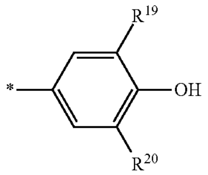

where $R^{19}$ and $R^{20}$ each represent a hydrogen atom, an alkyl group having 1 to 12 carbon atoms, or an aralkyl group having 7 to 36 carbon atoms, and * represents a bonding site.

2. The adhesive for an endoscope according to claim 1, wherein the component (C) includes at least one of the component (C-6) or the component (C-7).

3. The adhesive for an endoscope according to claim 1, wherein the component (C) includes the component (C-6).

4. The adhesive for an endoscope according to claim 1, wherein the component (C-6) includes at least one of a component (C-6-1) below or a component (C-6-2) below, Component (C-6-1): a compound represented by general formula (C-6-1) below Component (C-6-2): a compound having a constituent represented by general formula (C-6-2) below general formula (C-6-1)

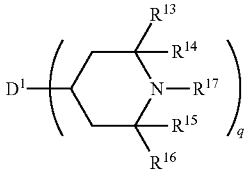

-continued general formula (C-6-2)

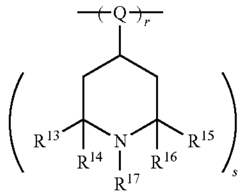

where $R^{13}$ to $R^{17}$ respectively have the same definitions as $R^{13}$ to $R^{17}$ in general formula (C-6), q represents an integer of 2 or greater, D1 represents a q-valent linking group, r represents an integer, Q represents an (s+2)-valent linking group, and s represents 1 or 2.

5. The adhesive for an endoscope according to claim 1, wherein the component (C-7) includes at least one of a component (C-7-1) below or a component (C-7-2) below, Component (C-7-1): a compound represented by general formula (C-7-1) below Component (C-7-2): a compound represented by general formula (C-7-2) below general formula (C-7-1)

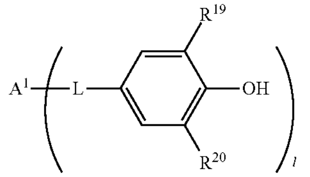

general formula (C-7-2)

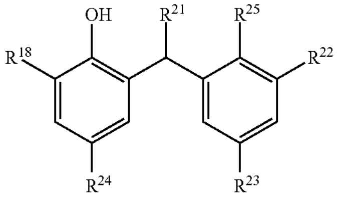

where $R^{19}$ and $R^{20}$ respectively have the same definitions as $R^{19}$ and $R^{20}$ in general formula (C-7), L represents a single bond or a divalent linking group, t represents an integer of 2 to 4, $A^1$ represents a divalent to tetravalent linking group, $R^{21}$ to $R^{24}$ each have the same definition as $R^{19}$, and $R^{25}$ represents a reactive organic substituent.

6. A cured product obtained by curing the adhesive for an endoscope according to claim 1.

7. An endoscope comprising a member fixed with the cured product according to claim 6.

8. A method for producing an endoscope, comprising fixing a member by using the adhesive for an endoscope according to claim 1.

* * * * *